US008313422B2

(12) United States Patent
Creighton

(10) Patent No.: US 8,313,422 B2
(45) Date of Patent: *Nov. 20, 2012

(54) MAGNETIC-BASED METHODS FOR TREATING VESSEL OBSTRUCTIONS

(75) Inventor: Francis M. Creighton, Richmond Heights, MO (US)

(73) Assignee: Pulse Therapeutics, Inc., St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 13/471,908

(22) Filed: May 15, 2012

(65) Prior Publication Data

US 2012/0232329 A1 Sep. 13, 2012

Related U.S. Application Data

(63) Continuation-in-part of application No. 13/505,447, filed as application No. PCT/US2010/055133 on Nov. 2, 2010.

(60) Provisional application No. 61/280,321, filed on Nov. 2, 2009.

(51) Int. Cl.
*A61M 37/00* (2006.01)
*A61N 2/00* (2006.01)

(52) U.S. Cl. .......... 600/12; 977/909; 977/908; 977/905; 977/773; 977/700; 607/1; 424/489; 128/899; 128/898; 128/897; 335/300; 600/407; 600/427; 600/9; 600/13

(58) Field of Classification Search .................. 977/700, 977/737, 745, 773, 786, 833, 838, 839, 900–902, 977/904–906, 908, 915, 959, 963; 128/897, 128/898, 899; 335/300; 600/407, 427, 9, 600/12, 13, 114, 117, 118, 424; 607/1; 424/489; 606/159

See application file for complete search history.

(56) References Cited

U.S. PATENT DOCUMENTS 4,359,453 A 11/1982 Gordon
(Continued)

FOREIGN PATENT DOCUMENTS

WO WO 03/022360 3/2003
(Continued)

OTHER PUBLICATIONS

K.W. Peasley, "Destruction of Human Immunodeficiency-Infected Cells by Ferrofluid Particles Manipulated by an External Magnetic Field: Mechanical Disruption and Selective Introduction of Cytotoxic or Antiretroviral Substances into Target Cells," Medical Hypthesis, Jan. 1996, pp. 5-12, vol. 46, Issue 1.

(Continued)

*Primary Examiner* — Samuel G. Gilbert
*Assistant Examiner* — Sunita Reddy
(74) *Attorney, Agent, or Firm* — Knobbe, Martens, Olson & Bear LLP

(57) ABSTRACT

Some embodiments provide a system for external manipulation of magnetic nanoparticles in vasculature using a remotely placed magnetic field-generating stator. In one aspect, the systems and methods relate to the control of magnetic nanoparticles in a fluid medium using permanent magnet-based or electromagnetic field-generating stator sources. Such a system can be useful for increasing the diffusion of therapeutic agents in a fluid medium, such as a human circulatory system, which can result in substantial clearance of fluid obstructions, such as vascular occlusions, in a circulatory system resulting in increased blood flow.

21 Claims, 53 Drawing Sheets

U.S. PATENT DOCUMENTS

| | | | |
|---|---|---|---|
| 5,543,158 A | 8/1996 | Gref et al. | |
| 5,654,864 A | 8/1997 | Ritter et al. | |
| 5,665,277 A | 9/1997 | Johnson et al. | |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,231,496 B1 | 5/2001 | Wilk et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,304,768 B1 | 10/2001 | Blume et al. | |
| 6,311,082 B1 | 10/2001 | Creighton, IV et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,459,924 B1 | 10/2002 | Creighton, IV et al. | |
| 6,475,223 B1 | 11/2002 | Werp et al. | |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,527,782 B2 | 3/2003 | Hogg et al. | |
| 6,529,761 B2 | 3/2003 | Creighton, IV et al. | |
| 6,537,196 B1 | 3/2003 | Creighton, IV et al. | |
| 6,542,766 B2 | 4/2003 | Hall et al. | |
| 6,562,019 B1 | 5/2003 | Sell | |
| 6,630,879 B1 | 10/2003 | Creighton, IV et al. | |
| 6,662,034 B2 | 12/2003 | Segner et al. | |
| 6,677,752 B1 | 1/2004 | Creighton, IV et al. | |
| 6,702,804 B1 | 3/2004 | Ritter et al. | |
| 6,733,511 B2 | 5/2004 | Hall et al. | |
| 6,740,103 B2 | 5/2004 | Hall et al. | |
| 6,755,816 B2 | 6/2004 | Ritter et al. | |
| 6,786,219 B2 | 9/2004 | Garibaldi et al. | |
| 6,817,364 B2 | 11/2004 | Garibaldi et al. | |
| 6,834,201 B2 | 12/2004 | Gillies et al. | |
| 6,902,528 B1 | 6/2005 | Garibaldi et al. | |
| 6,911,026 B1 | 6/2005 | Hall et al. | |
| 6,940,379 B2 | 9/2005 | Creighton | |
| 6,968,846 B2 | 11/2005 | Viswanathan | |
| 6,975,197 B2 | 12/2005 | Creighton, IV | |
| 6,980,843 B2 | 12/2005 | Eng et al. | |
| 7,008,418 B2 | 3/2006 | Hall et al. | |
| 7,010,338 B2 | 3/2006 | Ritter et al. | |
| 7,017,584 B2 | 3/2006 | Garibaldi et al. | |
| 7,019,610 B2 | 3/2006 | Creighton, IV et al. | |
| 7,020,512 B2 | 3/2006 | Ritter et al. | |
| 7,052,777 B2 | 5/2006 | Brotzman, Jr. et al. | |
| 7,066,924 B1 | 6/2006 | Garibaldi et al. | |
| 7,137,976 B2 | 11/2006 | Ritter et al. | |
| 7,161,453 B2 | 1/2007 | Creighton, IV | |
| 7,189,198 B2 | 3/2007 | Harburn et al. | |
| 7,190,819 B2 | 3/2007 | Viswanathan | |
| 7,211,082 B2 | 5/2007 | Hall et al | |
| 7,248,914 B2 | 7/2007 | Hastings et al. | |
| 7,264,584 B2 | 9/2007 | Ritter et al. | |
| 7,276,044 B2 | 10/2007 | Ferry et al. | |
| 7,286,034 B2 | 10/2007 | Creighton | |
| 7,305,263 B2 | 12/2007 | Creighton, IV | |
| 7,313,429 B2 | 12/2007 | Creighton, IV et al. | |
| 7,329,638 B2 | 2/2008 | Yang et al. | |
| 7,341,063 B2 | 3/2008 | Garbibaldi et al. | |
| 7,346,379 B2 | 3/2008 | Eng et al. | |
| 7,389,778 B2 | 6/2008 | Sabo et al. | |
| 7,416,335 B2 | 8/2008 | Munger | |
| 7,459,145 B2 | 12/2008 | Bao et al. | |
| 7,495,537 B2 | 2/2009 | Tunay | |
| 7,505,615 B2 | 3/2009 | Viswanathan | |
| 7,516,416 B2 | 4/2009 | Viswanathan et al. | |
| 7,524,630 B2 | 4/2009 | Tan et al. | |
| 7,537,570 B2 | 5/2009 | Kastelein | |
| 7,540,288 B2 | 6/2009 | Viswanathan et al. | |
| 7,540,866 B2 | 6/2009 | Viswanathan et al. | |
| 7,543,239 B2 | 6/2009 | Viswanathan et al. | |
| 7,555,331 B2 | 6/2009 | Viswanathan | |
| 7,567,233 B2 | 7/2009 | Garibaldi et al. | |
| 7,603,905 B2 | 10/2009 | Creighton, IV | |
| 7,623,736 B2 | 11/2009 | Viswanathan | |
| 7,625,382 B2 | 12/2009 | Werp et al. | |
| 7,627,361 B2 | 12/2009 | Viswanathan | |
| 7,630,752 B2 | 12/2009 | Viswanathan | |
| 7,635,342 B2 | 12/2009 | Ferry et al. | |
| 7,657,075 B2 | 2/2010 | Viswanathan | |
| 7,662,126 B2 | 2/2010 | Creighton, IV | |
| 7,690,619 B2 | 4/2010 | Wolfersberger | |
| 7,708,696 B2 | 5/2010 | Ritter et al. | |
| 7,742,803 B2 | 6/2010 | Viswanathan et al. | |
| 7,747,960 B2 | 6/2010 | Garibaldi et al. | |
| 7,751,867 B2 | 7/2010 | Viswanathan | |
| 7,756,308 B2 | 7/2010 | Viswanathan | |
| 7,757,694 B2 | 7/2010 | Ritter et al. | |
| 7,761,133 B2 | 7/2010 | Viswanathan et al. | |
| 7,766,856 B2 | 8/2010 | Ferry et al. | |
| 7,769,428 B2 | 8/2010 | Viswanathan et al. | |
| 7,769,444 B2 | 8/2010 | Pappone | |
| 7,771,415 B2 | 8/2010 | Ritter et al. | |
| 7,771,437 B2 | 8/2010 | Hogg et al. | |
| 7,772,950 B2 | 8/2010 | Tunay | |
| 7,774,046 B2 | 8/2010 | Werp et al. | |
| 7,815,580 B2 | 10/2010 | Viswanathan | |
| 7,818,076 B2 | 10/2010 | Viswanathan | |
| 7,831,294 B2 | 11/2010 | Viswanathan | |
| 7,853,306 B2 | 12/2010 | Viswanathan et al. | |
| 7,892,233 B2 | 2/2011 | Hall et al. | |
| 7,961,924 B2 | 6/2011 | Viswanathan | |
| 7,961,926 B2 | 6/2011 | Viswanathan | |
| 7,966,059 B2 | 6/2011 | Creighton, Iv et al. | |
| 7,983,733 B2 | 7/2011 | Viswanathan | |
| 7,998,020 B2 | 8/2011 | Kidd et al. | |
| 8,024,024 B2 | 9/2011 | Viswanathan et al. | |
| 8,060,184 B2 | 11/2011 | Hastings et al. | |
| 8,088,129 B2 | 1/2012 | Werp et al. | |
| 8,092,450 B2 | 1/2012 | Davies et al. | |
| 8,114,032 B2 | 2/2012 | Ferry et al. | |
| 8,135,185 B2 | 3/2012 | Blume et al. | |
| 8,162,920 B2 | 4/2012 | Ritter et al. | |
| 8,192,374 B2 | 6/2012 | Viswanathan | |
| 8,196,590 B2 | 6/2012 | Sabo et al. | |
| 2001/0038683 A1 | 11/2001 | Ritter et al. | |
| 2002/0019644 A1 | 2/2002 | Hastings et al. | |
| 2002/0072662 A1 | 6/2002 | Hall et al. | |
| 2002/0100486 A1 | 8/2002 | Creighton et al. | |
| 2002/0103426 A1 | 8/2002 | Segner et al. | |
| 2002/0103430 A1 | 8/2002 | Hastings et al. | |
| 2002/0115904 A1 | 8/2002 | Ren | |
| 2003/0009094 A1 | 1/2003 | Segner et al. | |
| 2003/0181809 A1 | 9/2003 | Hall et al. | |
| 2004/0006301 A1 | 1/2004 | Sell et al. | |
| 2004/0006350 A1 | 1/2004 | Hogg et al. | |
| 2004/0064153 A1 | 4/2004 | Creighton et al. | |
| 2004/0077942 A1 | 4/2004 | Hall et al. | |
| 2004/0096511 A1 * | 5/2004 | Harburn et al. | 424/489 |
| 2004/0133130 A1 | 7/2004 | Ferry et al. | |
| 2004/0147829 A1 | 7/2004 | Segner et al. | |
| 2004/0157082 A1 | 8/2004 | Ritter et al. | |
| 2004/0186376 A1 | 9/2004 | Hogg et al. | |
| 2004/0260172 A1 | 12/2004 | Ritter et al. | |
| 2004/0267106 A1 | 12/2004 | Segner et al. | |
| 2005/0004585 A1 | 1/2005 | Hall et al. | |
| 2005/0020911 A1 | 1/2005 | Viswanathan et al. | |
| 2005/0021063 A1 | 1/2005 | Hall et al. | |
| 2005/0033162 A1 | 2/2005 | Garibaldi et al. | |
| 2005/0065435 A1 | 3/2005 | Rauch et al. | |
| 2005/0113628 A1 * | 5/2005 | Creighton et al. | 600/1 |
| 2005/0113812 A1 | 5/2005 | Viswanathan et al. | |
| 2005/0119556 A1 | 6/2005 | Gillies et al. | |
| 2005/0119687 A1 | 6/2005 | Dacey et al. | |

| | | |
|---|---|---|
| 2005/0182315 A1 | 8/2005 | Ritter et al. |
| 2005/0256398 A1 | 11/2005 | Hastings et al. |
| 2005/0273130 A1 | 12/2005 | Sell |
| 2005/0281858 A1* | 12/2005 | Kloke et al. ............... 424/423 |
| 2006/0025675 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036163 A1 | 2/2006 | Viswanathan |
| 2006/0041181 A1 | 2/2006 | Viswanathan et al. |
| 2006/0094956 A1 | 5/2006 | Viswanathan |
| 2006/0142630 A1 | 6/2006 | Meretei |
| 2006/0142632 A1* | 6/2006 | Meretei ........................ 600/12 |
| 2006/0144407 A1 | 7/2006 | Aliberto et al. |
| 2006/0144408 A1 | 7/2006 | Ferry |
| 2006/0165805 A1* | 7/2006 | Steinhoff et al. ............. 424/489 |
| 2006/0270948 A1 | 11/2006 | Viswanathan et al. |
| 2006/0276867 A1 | 12/2006 | Viswanathan |
| 2006/0278248 A1 | 12/2006 | Viswanathan |
| 2006/0281990 A1 | 12/2006 | Viswanathan et al. |
| 2007/0016010 A1 | 1/2007 | Creighton et al. |
| 2007/0016131 A1 | 1/2007 | Munger et al. |
| 2007/0021731 A1 | 1/2007 | Garibaldi et al. |
| 2007/0021744 A1 | 1/2007 | Creighton |
| 2007/0032746 A1 | 2/2007 | Sell |
| 2007/0038065 A1 | 2/2007 | Creighton et al. |
| 2007/0038074 A1 | 2/2007 | Ritter et al. |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0062546 A1 | 3/2007 | Viswanathan et al. |
| 2007/0149946 A1 | 6/2007 | Viswanathan et al. |
| 2007/0167720 A1 | 7/2007 | Viswanathan et al. |
| 2007/0197899 A1 | 8/2007 | Ritter et al. |
| 2007/0197906 A1 | 8/2007 | Ritter |
| 2007/0225589 A1 | 9/2007 | Viswanathan |
| 2007/0250041 A1 | 10/2007 | Werp |
| 2007/0270686 A1 | 11/2007 | Ritter et al. |
| 2007/0287909 A1 | 12/2007 | Garibaldi et al. |
| 2008/0004595 A1 | 1/2008 | Viswanathan et al. |
| 2008/0006280 A1 | 1/2008 | Aliberto et al. |
| 2008/0015427 A1 | 1/2008 | Kastelein et al. |
| 2008/0016677 A1 | 1/2008 | Creighton |
| 2008/0039705 A1 | 2/2008 | Viswanathan |
| 2008/0039830 A1 | 2/2008 | Munger et al. |
| 2008/0047568 A1* | 2/2008 | Ritter et al. ................... 128/898 |
| 2008/0058608 A1 | 3/2008 | Garibaldi et al. |
| 2008/0058609 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0065061 A1 | 3/2008 | Viswanathan |
| 2008/0092993 A1 | 4/2008 | Creighton |
| 2008/0097200 A1 | 4/2008 | Blume et al. |
| 2008/0114335 A1 | 5/2008 | Flickinger et al. |
| 2008/0200913 A1 | 8/2008 | Viswanathan |
| 2008/0208912 A1 | 8/2008 | Garibaldi |
| 2008/0228065 A1 | 9/2008 | Viswanathan et al. |
| 2008/0228068 A1 | 9/2008 | Viswanathan et al. |
| 2008/0287909 A1 | 11/2008 | Viswanathan et al. |
| 2008/0294232 A1 | 11/2008 | Viswanathan |
| 2008/0312673 A1 | 12/2008 | Viswanathan et al. |
| 2009/0012821 A1 | 1/2009 | Besson et al. |
| 2009/0062646 A1 | 3/2009 | Creighton, IV et al. |
| 2009/0062828 A1* | 3/2009 | Marr ............................ 606/159 |
| 2009/0082722 A1 | 3/2009 | Munger et al. |
| 2009/0105579 A1 | 4/2009 | Garibaldi |
| 2009/0131798 A1 | 5/2009 | Minar et al. |
| 2009/0131927 A1 | 5/2009 | Kastelein et al. |
| 2009/0138009 A1 | 5/2009 | Viswanathan et al. |
| 2009/0177032 A1 | 7/2009 | Garibaldi et al. |
| 2009/0287036 A1 | 11/2009 | Shapiro et al. |
| 2009/0306643 A1 | 12/2009 | Pappone et al. |
| 2010/0063385 A1 | 3/2010 | Garibaldi et al. |
| 2010/0069733 A1 | 3/2010 | Kastelein et al. |
| 2010/0097315 A1 | 4/2010 | Garibaldi et al. |
| 2010/0137706 A1 | 6/2010 | Viswanathan |
| 2010/0163061 A1 | 7/2010 | Creighton |
| 2010/0222669 A1 | 9/2010 | Flickinger et al. |
| 2010/0269838 A1 | 10/2010 | Flanagan et al. |
| 2010/0298845 A1 | 11/2010 | Kidd et al. |
| 2011/0022029 A1 | 1/2011 | Viswanathan |
| 2011/0028989 A1 | 2/2011 | Ritter et al. |
| 2011/0046618 A1 | 2/2011 | Minar et al. |
| 2011/0087237 A1 | 4/2011 | Viswanathan |
| 2011/0130718 A1 | 6/2011 | Kidd et al. |
| 2011/0152712 A1 | 6/2011 | Cao et al. |

FOREIGN PATENT DOCUMENTS

| | | |
|---|---|---|
| WO | WO 2005/011810 | 2/2005 |
| WO | WO 2005/072169 | 8/2005 |

OTHER PUBLICATIONS

Tadao Sugimoto, Egon Matijevic, "Formation of Uniform Spherical Magnetite Particles by Crystallization from Ferrous Hydroxide Gels," Journal of Colloid and Interface Science, Mar. 1980, pp. 227-243, vol. 74, Issue 1.

D. Pouliquen, et. al., "Iron oxide nanoparticles for use as an MRI contrast agent: pharmacokinetics and metabolism," Magnetic Resonance Imaging, 1991, pp. 275-283, vol. 9, Issue 3.

Robert J. Leadley Jr., et al., "Contribution of in vivo models of thrombosis to the discovery and development of novel antithrombotic agents," Journal of Pharmacological and Toxicological Methods, Mar.-Apr. 2000, pp. 101-116, vol. 43, Issue 2.

Robert M. Califf, et al., "Hemorrhagic complications associated with the use of intravenous tissue plasminogen activator in treatment of acute myocardial infarction," The American Journal of Medicine, Sep. 1988, pp. 353-359, vol. 85, Issue 3.

* cited by examiner

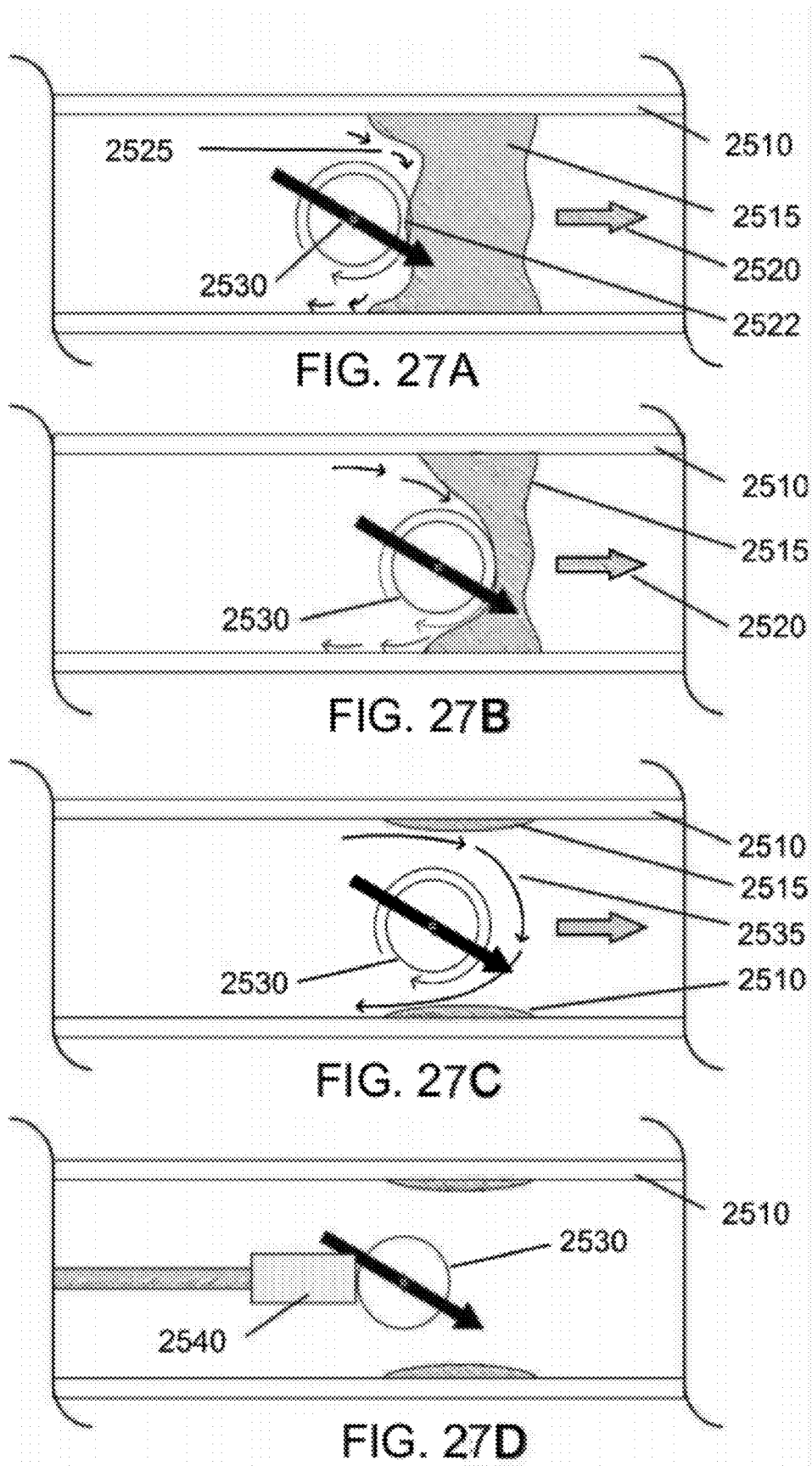

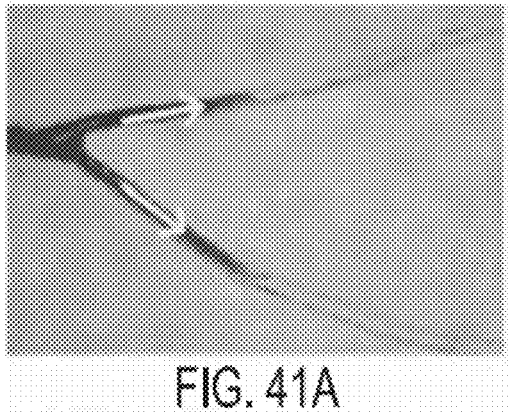
FIG. 41A
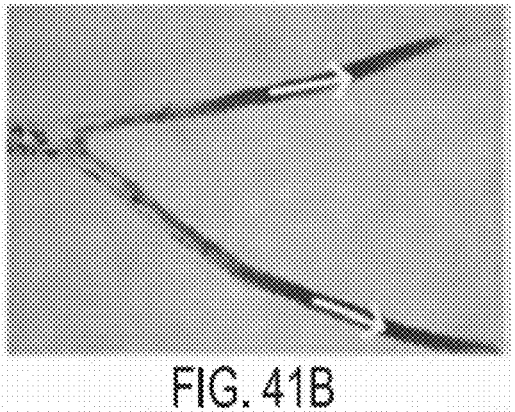
FIG. 41B
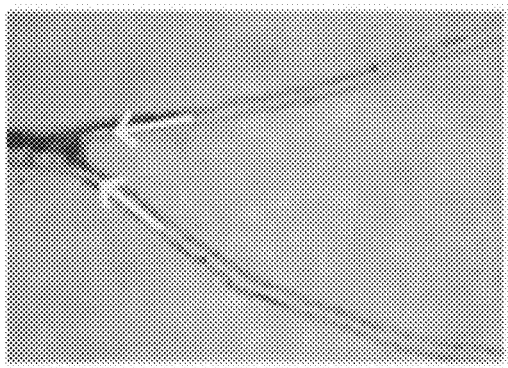
FIG. 41C
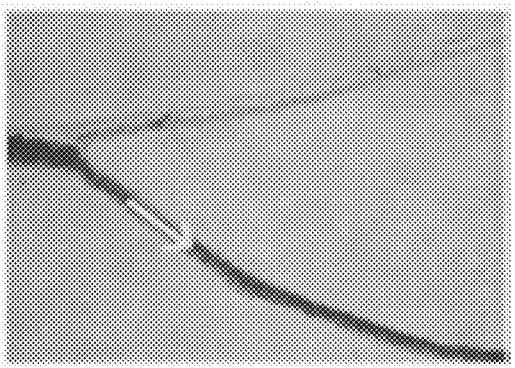
FIG. 41D
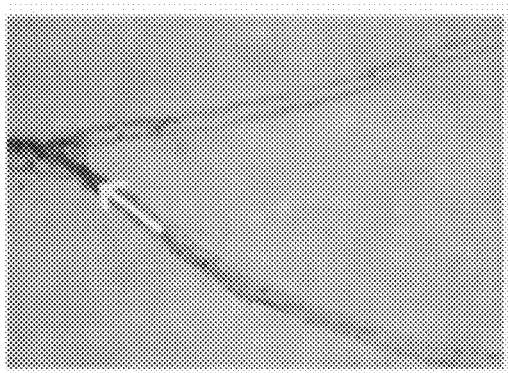
FIG. 41E
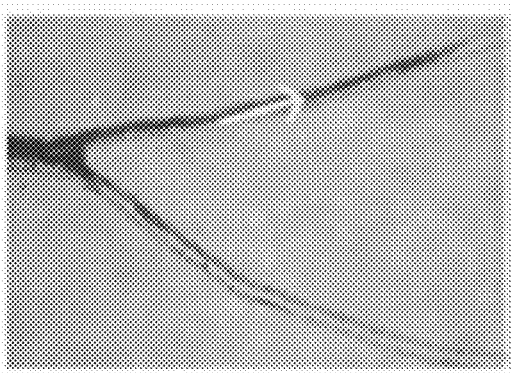
FIG. 41F
FIG. 41

MAGNETIC-BASED METHODS FOR TREATING VESSEL OBSTRUCTIONS

CROSS-REFERENCE TO RELATED APPLICATIONS

This application is a continuation-in-part of U.S. patent application Ser. No. 13/505,447, hag a 371(c) date of Aug. 21, 2012, which is a National Phase Application of International Application Number PCT/US2010/055133, filed Nov. 2, 2010, published as International Publication Number WO 2011/053984 on May 5, 2011, which claims the benefit of U.S. Provisional Application Ser. No. 61/280,321 filed on Nov. 2, 2009. This application hereby expressly incorporates by reference each of the above-identified applications in their entirety.

FIELD

This disclosure relates to systems and methods for facilitating introduction and external manipulation of magnetic nanoparticles within a circulatory system.

DESCRIPTION OF THE RELATED ART

The treatment of fluid obstructions in the circulatory system, including vascular occlusions in vessels of the brain and vessels of the extremities, has included the use of drugs that can dissolve the obstructions and obstruction removal devices, e.g., thrombectomy devices. However, side-effects of such drugs are difficult to control and such obstruction removal devices often involve invasive procedures that cause unintended or secondary tissue damage. Both the use of drugs at normal dosages and the use of invasive thrombectomy devices can cause death.

SUMMARY

In several embodiments, a therapeutic system is provided comprising (a) a magnet having a magnetic field and a gradient for controlling magnetic rotors in a circulatory system, and (b) a controller for positioning and rotating the field and the gradient in a manner to agglomerate and move the magnetic rotors with respect to a therapeutic target in the circulatory system. Using the therapeutic system, contact of the therapeutic target with a pharmaceutical composition in the circulatory system is increased according to one embodiment. In various aspects, the pharmaceutical composition can be attached to the magnetic rotor, and in other aspects can be administered to the circulatory system separate from the magnetic rotors. In certain instances, the pharmaceutical composition can be a thrombolytic drug.

Therapeutic targets of the system can include fluid obstructions such as, but not limited to, atherosclerotic plaques, fibrous caps, fatty buildup, coronary occlusions, arterial stenosis, arterial restenosis, vein thrombi, arterial thrombi, cerebral thrombi, embolism, hemorrhage, very small vessels, other fluid obstructions, or any combination of these. Therapeutic targets of the system can also include any organ or tissue (e.g., tumor) of the body. For example, therapeutic targets can be targets identified for stem cell and/or gene therapy. In various aspects, the circulatory system is vasculature of a patient, in particular, a human patient.

In various embodiments, the therapeutic system comprises a permanent magnet coupled to a motor, and the controller controls a motor to position the magnet at an effective distance and an effective plane with respect to the therapeutic target, and rotates the magnet at an effective frequency with respect to the therapeutic target. In various embodiments, the therapeutic system comprises an electromagnet having a magnetic field strength and magnetic field polarization driven by electrical current, and the controller positions the electromagnet at an effective distance and an effective plane with respect to the therapeutic target, and rotates the magnetic field of the electromagnet by adjusting the electrical current.

The therapeutic system can further include a display for viewing the magnetic rotors and therapeutic target, and a user interface for controlling the magnetic rotors, such that a user can control the magnetic rotors to clear, remove, or reduce in size a therapeutic target by adjusting a frequency of the rotating magnetic field, an orientation plane of the rotating magnetic field with respect to the therapeutic target, and/or a distance of the rotating magnetic field with respect to the therapeutic target. In various aspects, the therapeutic target can be a thrombosis or clot in a human blood vessel. In various aspects, the magnetic rotors can be magnetic nanoparticles injected into the circulatory system. The magnetic nanoparticles can be coated or uncoated.

In several embodiments, the magnetic rotors move through the fluid in the circular motion by repeatedly (a) walking end over end along the blood vessel away from the magnetic field in response to the rotation of the rotors caused by torque exerted on the rotors by a rotating magnetic field and an attractive force (e.g., a directed gradient) of the magnetic field, and (b) flowing back through the fluid towards the magnetic field in response to the rotation of the rotors and the attractive force (e.g., directed gradient) of the magnetic field.

In some embodiments, a therapeutic system is provided for increasing fluid flow in a circulatory system comprising a magnet having a magnetic field for controlling a magnetic tool in the fluid, and a controller configured to position and rotate the magnetic field with respect to the therapeutic target to rotate an abrasive surface of the magnetic tool and maneuver the rotating abrasive surface to contact and increase fluid flow through or around the therapeutic target. In various aspects, the circulatory system can be vasculature of a patient, particularly a human patient. In various aspects, the magnetic tool can be coupled to a stabilizing rod, and the magnetic tool rotates about the stabilizing rod in response to the rotating magnetic field. In some aspects, the magnetic tool can include an abrasive cap affixed to a magnet which engages and cuts through the therapeutic target. In certain aspects, the controller positions the magnetic tool at a target point on the therapeutic target, and rotates the magnetic tool at a frequency sufficient to cut through the therapeutic target. The magnet can be positioned so that poles of the magnet periodically attract the opposing poles of the magnetic tool during rotation, and the magnetic tool is pushed towards the therapeutic target by a stabilizing rod upon which the magnetic tool rotates. In some aspects, the magnet can be positioned so that the poles of the magnet continuously attract the opposing poles of the magnetic tool during rotation, and the magnetic tool is pulled towards the therapeutic target by an attractive force (e.g., a directed gradient) of the magnet.

In some embodiments, a system is provided for increasing fluid flow in a circulatory system comprising a magnet having a magnetic field for controlling magnetic rotors in the fluid, a display for displaying, to a user, the magnetic rotors and the therapeutic target in the fluid, and a controller that, in response to instructions from the user, controls the magnetic field to: (a) position the magnetic rotors adjacent to the therapeutic target, (b) adjust an angular orientation of the magnetic rotors with respect to the therapeutic target, and (c) rotate and move the magnetic rotors through the fluid in a generally circular motion to mix the fluid and substantially clear the therapeutic target.

In various embodiments, the display can display real time (e.g., streaming) video of the magnetic rotors and the therapeutic target, and the display can superimpose a graphic representative of a rotation plane of the magnetic field and another graphic representative of the attractive force (e.g., directed gradient) of the magnetic field on the real time video on the display. In some aspects, the magnet can be a permanent magnet coupled to a motor and a movable arm, and the controller can include a remote control device for a user to manipulate the position, rotation plane and/or rotation frequency of the magnetic field with respect to the therapeutic target. The remote control device can be used to manipulate the position and rotation plane in one, two, or three dimensions. In some aspects, the real time video can correspond to images received from an imaging system, such as a transcranial Doppler imaging system, a PET imaging system, an x-ray imaging system, an MRI imaging system, a CT imaging system, an ultrasound imaging system, and/or the like. In some embodiments, the imaging system is relatively immune from the magnetic fields present when the control system is in operation. The control system can receive images from the imaging system, register the images, and present them to the user to provide real-time feedback as to the position of the magnetic nanoparticles, vasculature of the patient, and/or the location of the target object. In some embodiments, imaging the magnetic nanoparticles can provide information about drug infusion and/or dose concentration. Using this information, the control of the magnetic nanoparticles can be altered between a mode where nanoparticles are collected, and a mode where nanoparticles are vortexed, or made to follow a substantially circular path to better mix the chemical agent within the vasculature, thereby enhancing diffusion of the chemical agent to the location of the therapeutic target and/or to enhance interaction of the chemical agent with the therapeutic target. In some embodiments, the magnetic nanoparticles can include a contrast agent or tracer and can be correlated to a drug or chemical agent. In some embodiments, the magnetic nanoparticles are used as an indication of the amount of diffusion within the vasculature in a region of the therapeutic target.

In some embodiments, the display can adjust the graphics in response to instructions received from the user through the remote control device. In various aspects, the magnet can be an electro-magnet coupled to a motor and a movable arm, and the controller can perform image processing to identify the location, shape, thickness and density of the therapeutic target, and can automatically manipulate the movable arm to control the position, rotation plane and/or rotation frequency of the magnetic field to clear the therapeutic target. In some aspects, the automatic manipulation can control the nanoparticles according to a navigation route designated or programmed by a user. The user can determine and input the navigation route and make adjustments during particle infusion or at any other time during a therapeutic procedure. In some aspects, the navigation route can be automatically calculated and/or adjusted by a controller of the therapeutic system.

In some embodiments, the automatic manipulation allows the magnetic system to be stowed in a substantially shielded enclosure, thereby substantially reducing or preventing magnetic fields of one or more magnets of the system from having an effect on persons or items outside the system. For example, the system can include an enclosure made out of a suitable shielding material (e.g., iron). The automatic manipulation provided by the controller can move the one or more magnets of the system into the shielded enclosure when not in use.

In some embodiments, the therapeutic system provides real-time information for the improved control of movement of the magnetic nanoparticles. The magnetic nanoparticles can be configured to be detectable with an imaging modality. For example, the magnetic nanoparticles may be attached to a contrast or nuclear agent to be visible using an x-ray-based system or PET scanner, respectively. Other imaging modalities can include Doppler imaging (e.g., transcranial Doppler), which may detect the fluidic current through vasculature created by the magnetic nanoparticles, or ultrasound-based diagnostic imaging systems, which may provide direct two-dimension or three-dimensional imaging. Combining the control system with an imaging system can provide the ability to track the infusion of the chemical adjunct in real-time into low-blood-flow lumens. By manipulating the magnetic system, three-degrees of control of the infused magnetic nanoparticles can be achieved, thereby improving the ability to direct the therapy.

The imaging modality can be any modality, including imaging modalities capable of resolving a device or chemical agent which is affected by the fluidic current generated by the magnetic nanoparticles. The imaging modality, in one embodiment, images an area of interest and provides metric information. The therapeutic system can include a communication module for communicating imaging data to an external device (such as a display device or a storage device). The therapeutic system can include a registering module for registering the reference frame of the image to the reference frame of the magnetic system. The system can then receive the image, register the image, track the magnetic nanoparticles, and provide a means of directing the nanoparticles to be navigated along a desired path, either by an operator or automatically by a controller of a computing device. The imaging data can be two- or three-dimensional data. Three-dimensional information could be advantageous where navigational control occurs in three dimensions. In some embodiments, the control of the magnetic nanoparticles can occur remotely using the systems described herein.

In certain embodiments, the magnetic rotors can be formed by magnetic nanoparticles which combine in the presence of the magnetic field (e.g., to form a chain of nanoparticles). In some aspects, the fluid can be a mixture of blood and a therapeutic agent (e.g., a thrombolytic drug), the blood and therapeutic agent being mixed by the generally circular motion of the magnetic rotors to erode and clear a therapeutic target. In some aspects, the generally circular motion of the magnetic rotors can redirect the therapeutic agent from a high flow blood vessel to a low flow blood vessel which contains the therapeutic target.

In one embodiment, a method is also provided for increasing fluid flow in a circulatory system comprising: (a) administering a therapeutically effective amount of magnetic rotors to the circulatory system of a patient having a fluid obstruction, and (b) applying a magnet to the patient, the magnet having a magnetic field and a gradient for controlling the magnetic rotors in a circulatory system, and (c) using a controller for positioning and rotating the field and the gradient in a manner to agglomerate and move the magnetic rotors with respect to a therapeutic target in the circulatory system of the patient, wherein contact of the therapeutic target with a therapeutic agent (e.g., a pharmaceutical composition) in the circulatory system is increased and fluid flow is increased.

The therapeutic agent (e.g., pharmaceutical composition, chemical adjunct), according to several embodiments, can be attached to the magnetic rotor or to the individual magnetic nanoparticles comprising the magnetic rotor. For example, the magnetic nanoparticles can include a coating to facilitate attachment of therapeutic agents. The therapeutic agent can be administered to the circulatory system of the patient separate from the magnetic rotors. In various embodiments, the therapeutic agent is a thrombolytic drug.

In some embodiments, the magnet can be a permanent magnet rotatably coupled to a motor, and the controller can control the motor to position the magnet at an effective distance and an effective orientation plane with respect to the therapeutic target, and can rotate the magnet at an effective frequency to cause the magnetic rotors to travel within the vasculature toward the therapeutic target. In some embodiments, the magnet can be an electromagnet having a magnetic field strength and magnetic field polarization driven by electrical current, and the controller can position the electromagnet at an effective distance and an effective orientation plane with respect to the therapeutic target, and can rotate the magnetic field of the electro-magnet by adjusting the electrical current.

The system of the method, according to several embodiments, can further include a display for viewing the magnetic rotors and therapeutic target, and a user interface for controlling the magnetic rotors, wherein a user controls the magnetic rotors to increase contact of the therapeutic target with a therapeutic agent (e.g., a pharmaceutical composition, chemical adjunct, stem cell, anti-cancer agent, anti-angiogenesis agent) in the circulatory system by adjusting a frequency of the rotating magnetic field, a plane of the rotating magnetic field with respect to the therapeutic target, and/or a distance of the rotating magnetic field with respect to the therapeutic target.

The therapeutic target, according to several embodiments, can be a thrombosis (e.g., a clot) in a human blood vessel (e.g., a blood vessel of the brain or leading to the brain or a blood vessel in a leg). In some aspects, the magnetic rotors can be formed from magnetic nanoparticles injected into the circulatory system. The therapeutic target, in one embodiment, is a full or partial blockage of a vein bivalve. In certain aspects, the magnetic rotors move through the fluid in a generally circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

The rotor, according to several embodiments, is a magnetic nanoparticle of a diameter greater than or equal to about 10 nm and/or less than or equal to about 200 nm, including but not limited to from about 10 nm to about 150 nm, from about 15 nm to about 100 nm, from about 20 nm to about 60 nm, from about 20 nm to about 100 nm, from about 30 nm to about 50 nm, overlapping ranges thereof, less than 200 nm, less than 150 nm, less than 100 nm, less than 60 nm. In some aspects, the therapeutic target is a vascular occlusion in the patient's head or a vascular occlusion in the patient's leg.

In some embodiments, a method is provided for increasing drug diffusion in a circulatory system comprising (a) administering a therapeutically effective amount of magnetic rotors to the circulatory system of a patient, (b) applying a magnet to the patient, the magnet having a magnetic field and a gradient for controlling the magnetic rotors in a circulatory system, and (c) using a controller configured to position and rotate the field and the gradient in a manner to agglomerate and move the magnetic rotors with respect to a therapeutic target in the circulatory system of the patient, wherein diffusion of a therapeutic agent (e.g., a pharmaceutical composition) in the circulatory system at the therapeutic target is increased.

In accordance with several embodiments, a method of treating a thrombus within a blood vessel of the brain through external magnetomotive manipulation of magnetic nanoparticles is provided. The method can comprise introducing a thrombolytic drug within vasculature of a subject, the thrombolytic drug configured to have a therapeutic effect on a thrombus within a blood vessel of the brain. In some embodiments, the method comprises introducing a plurality of coated magnetic nanoparticles within the vasculature of the subject. The magnetic nanoparticles may have a diameter between about 15 nm and 150 nm, between about 20 nm and 200 nm, between about 10 nm and about 170 nm, or overlapping ranges thereof.

In some embodiments, the method comprises orienting a permanent magnet external to the blood vessel and having a magnetic field and a directed magnetic gradient to establish a magnetic rotation plane of the permanent magnet. The method may comprise programming a controller to cause the permanent magnet to be positioned and to rotate in a manner sufficient to cause the magnetic nanoparticles to agglomerate to form a plurality of magnetic nanoparticle rods having a length between 0.1 and 2 millimeters within the vasculature to travel toward the thrombus in an end over end motion in response to torque exerted by the rotating magnetic field and to an attractive force of the directed magnetic gradient.

In some embodiments, the rotational frequency of the rotating magnetic field is between 0.1 Hz and 30 Hz, between 1 Hz and 20 Hz, between 2 Hz and 10 Hz or overlapping ranges thereof. In some embodiments, the rotating magnetic field has a magnitude of between 0.01 Tesla and 0.1 Tesla, between 0.1 Tesla and 0.5 Tesla, between 0.05 Tesla and 1 Tesla, or overlapping ranges thereof. In some embodiments, the directed magnetic gradient has a strength of between 0.01 Tesla/meter and 5 Tesla/meter, between 0.05 Tesla/meter and 3 Tesla/meter, between 0.1 Tesla/meter and 2 Tesla/meter, or overlapping ranges thereof.

In some embodiments, the rotation of the magnet causes the magnetic nanoparticle rods to generate a circulating fluid motion within the vasculature proximal to the thrombus. The circulating fluid motion can facilitate (e.g., increase) contact of the thrombolytic drug with the thrombus by enhancing diffusion of the thrombolytic drug to the region of the blood vessel proximal to the thrombus and by refreshing contact of the thrombus with the thrombolytic drug (e.g., with drug that has not yet interacted with the thrombus), thereby providing more effective interaction of the thrombolytic drug with the thrombus.

In some embodiments, the thrombolytic drug is attached to the magnetic nanoparticles prior to introduction. In some embodiments, the thrombolytic drug is introduced within the vasculature separate from the magnetic nanoparticles. The permanent magnet can be coupled (e.g., rotatably) to a motor by a movable arm. In some embodiments, introducing a thrombolytic drug within vasculature of a subject comprises introducing a reduced dose of the thrombolytic drug than would be introduced if the magnetic nanoparticles were not introduced. In some embodiments, causing the magnetic nanoparticle rods to generate a circulating fluid motion within the vasculature proximal to the thrombus comprises adjusting the rotational frequency of the rotating magnetic field, a plane of the rotating magnetic field with respect to the thrombus, and/or a distance of the rotating magnetic field with respect to the thrombus.

In some embodiments, the method comprises adjusting one or more of the position, the rotation plane and the rotation frequency of the magnetic field in response to at least one characteristic of the thrombus. The characteristic of the thrombus can be a location, a shape, a thickness, a density, or other characteristic of the thrombus. In some embodiments, the characteristic is determined from one or more images of the region of the blood vessel in which the thrombus is located. In some embodiments, orienting a permanent magnet having a magnetic field and a directed magnetic gradient to establish a magnetic rotation plane of the permanent magnet is performed based on preoperative images of the blood vessel.

In accordance with several embodiments, a system for treating a fluid obstruction through external magnetomotive manipulation of magnetic nanoparticles introduced within vasculature of a subject is provided. In some embodiments, the system comprises a plurality of coated magnetic nanoparticles configured to be introduced within vasculature of a subject. The system can comprise a magnetomotive device configured to provide external manipulation of the magnetic nanoparticles within the vasculature.

In some embodiments, the magnetomotive device comprises a platform and a drive motor coupled to the platform by a motor support structure. In some embodiments, the magnetomotive device comprises a rotatable flange coupled to the drive motor. The rotatable flange can be coupled to the drive motor in a manner such that, in use, the drive motor rotates the rotatable flange about a central drive axis of the device or system. In some embodiments, a distal end of the rotatable flange comprises a mounting portion and a mounting plate coupled to the mounting portion. In some embodiments, a permanent magnet is coupled to the mounting plate such that, in use, the magnet rotates about the central drive axis of the magnetomotive device to provide a rotating, time-varying magnetic field and a directed magnetic gradient that controls movement of the magnetic nanoparticles introduced within vasculature of a subject. In some embodiments, the system comprises a controller that, in use, causes the drive motor to manipulate the movable arm (a) to control the position, rotation plane and rotation frequency of the magnetic field of the magnet and (b) to control the direction of the magnetic gradient of the magnet. In some embodiments, the controller positions and rotates the magnetic field and directs the magnetic gradient in a manner sufficient to cause the magnetic nanoparticles to agglomerate into a plurality of magnetic nanoparticle rods. The time-varying magnetic field and the directed magnetic gradient can cause the magnetic nanoparticle rods to generate a circulating fluid motion within a blood vessel proximal to a fluid obstruction that facilitates contact of a therapeutic agent introduced within the blood vessel with the fluid obstruction.

In some embodiments, the permanent magnet is a rectangular solid. The face of the magnet in which the North and South poles reside can be fastened to the mounting plate. The magnet can be coupled to the mounting portion at the distal end of the rotatable flange such that, in use, the magnetic field rotates parallel to a front face of the magnet. In some embodiments, the magnetic nanoparticle rods travel through the blood vessel by repeatedly a) walking end over end along the blood vessel away from the magnetic field in response to rotation of the magnetic nanoparticle rods caused by torque of the time-varying magnetic field and the directed magnetic gradient; and b) flowing back through fluid in the blood vessel towards the magnetic field in response to the rotation of the magnetic nanoparticle rods caused by torque of the time-varying magnetic field and the directed magnetic gradient. In some embodiments, a portable magnetomotive system for increasing fluid flow through an obstructed blood vessel by wireless manipulation of magnetic nanoparticles is provided that comprises a magnet pod and a headrest rotatably coupled to the magnet pod. The headrest, in use, can define a position and attitude of a subject's head in relation to the magnet pod. A rail attachment can be attached to the magnet pod that, in use, substantially secures the magnet pod to a rail or other support structure of a bed or other patient transport or occupancy unit. The portable magnetomotive system can comprise a magnet coupled to the magnet pod, the magnet having a magnetic field and a directed magnetic gradient that, in use, provides external magnetomotive control of magnetic nanoparticles introduced within vasculature of a subject.

In some embodiments, the magnetic nanoparticles comprise superparamagnetic iron oxide nanoparticles. In some embodiments, the movable arm is composed of nonmagnetic material and the movable arm passes through a first bearing and a second bearing adapted to facilitate smooth rotation of the movable arm, the first bearing and the second bearing being affixed to a platform by a bearing mounting structure. In some embodiments, the platform is suspended by a suspension arm that is coupled to an arm positioner of a portable base by a suspension arm attachment joint. In use, the suspension arm attachment joint is configured to allow rotation of the magnetomotive device about the end of the arm positioner coupled to the suspension arm attachment joint.

In some embodiments, the magnetomotive device comprises two motors, with a first motor adapted to rotate around a first axis to cause rotation of the magnet and a second motor adapted to rotate around a second axis to set the orientation of the rotation plane. In some embodiments, the therapeutic agent comprises a thrombolytic agent such as tissue plasminogen activator (tPA). The fluid obstruction can be an arterial thrombus in a cerebral blood vessel.

These and other features, aspects and advantages of the disclosure will become better understood with reference to the following description, examples and appended claims.

BRIEF DESCRIPTION OF THE DRAWINGS

Those of skill in the art will understand that the drawings, described below, are for illustrative purposes only. The drawings are not intended to limit the scope of the disclosure in any way.

FIGS. 27A-27D illustrate the use of a rotating magnetically-enabled thrombectomy sphere to address an occluded vessel, in accordance with an embodiment of the invention. FIG. 27A is a cross section view of a rotating magnetically-enabled thrombectomy sphere in circular motion against a total occlusion in a vessel. FIG. 27B is a cross section view of the magnetically-enabled thrombectomy sphere wearing away the surface of the occlusion. FIG. 27C is a cross section view of the magnetically-enabled thrombectomy sphere having opened the obstructed vessel. FIG. 27D is a cross section view of the magnetically-enabled thrombectomy sphere being removed by a small magnet on a guide wire.

FIG. 41 illustrates an example of bifurcated nanoparticle control using a parent vessel.

DETAILED DESCRIPTION

Abbreviations and Definitions

Figure 1A:
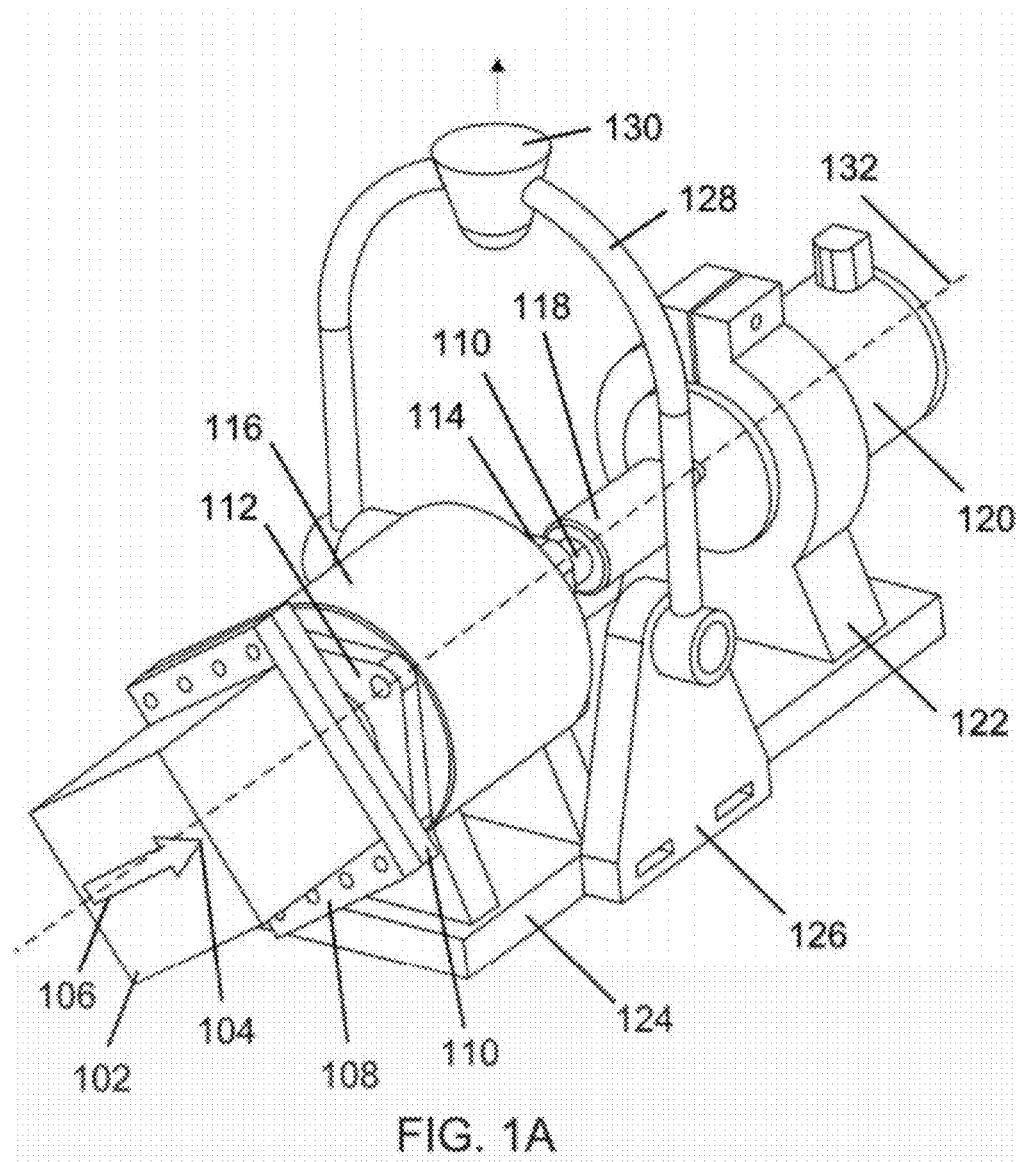
FIGS. 1A and 1B illustrate an example of a permanent-magnet stator system whose magnet's North-South pole rotates in a plane parallel to the system's front face, which is driven by a single motor.

The scientific and technical terms used in connection with the disclosure shall have their ordinary meanings (e.g., as commonly understood by those of ordinary skill in the art) in addition to any definitions included herein. Further, unless otherwise required by context, singular terms shall include pluralities and plural terms shall include the singular. The disclosures of The McGraw-Hill Dictionary of Chemical Terms (Parker, S., Ed., McGraw-Hill, San Francisco (1985)) and Ferrohydro-Dynamics (R. E. Rosensweig, Dover Publications, New York, (1985)) are hereby expressly incorporated by reference herein.

"Patient" shall be given its ordinary meaning and shall include, without limitation, human and veterinary subjects.

"Thrombolytic drug" shall be given its ordinary meaning and shall include without limitation drugs capable of degrading a blood clot or arteriosclerotic plaque. For example, a thrombolytic drug can include tissue plasminogen activator (tPA), plasminogen, streptokinase, urokinase, recombinant tissue plasminogen activators (rtPA), alteplase, reteplase, tenecteplase, and other drugs, and can include these drugs administered alone or co-administered with warfarin and/or heparin.

"Magnetic nanoparticle" shall be given its ordinary meaning and shall include without limitation a coated or uncoated metal particle having a diameter greater than or equal to about 1 nm and/or less than or equal to about 1000 nm, greater than or equal to about 10 nm and/or less than or equal to about 200 nm, greater than or equal to about 15 nm and/or less than or equal to about 150 nm, greater than or equal to about 20 nm and/or less than or equal to about 60 nm, 80 nm, 100 nm, and all integer values between 1 nm and 1000 nm, e.g., 1, 2, 3, 4, 5, . . . 997, 998, 999, and 1000. The appropriate sizes of magnetic nanoparticles can depend on the therapeutic target of the system (e.g., very small vessels can accept smaller nanoparticles and larger parts of a circulatory system can accept larger nanoparticles). Examples of such magnetic nanoparticles include superparamagnetic iron oxide nanoparticles. The nanoparticles may be made of magnetite or other ferromagnetic mineral or iron oxide and, in some embodiments, can be coated with any one or a combination of the following materials: (1) coatings which enhance the behavior of the nanoparticles in blood by making them either hydrophilic or hydrophobic; (2) coatings which buffer the nanoparticles and which optimize the magnetic interaction and behavior of the magnetic nanoparticles; (3) contrast agent or agents which allow visualization with magnetic resonance imaging, X-ray, Positron Emission Tomography (PET), ultrasound, or other imaging technologies; (4) therapeutic agents which accelerate destruction of a circulatory system blockage; (5) stem cells, anti-cancer drugs, and/or anti-angiogenesis drugs; and (6) thrombolytic drugs. Examples of both coated and uncoated magnetic nanoparticles and methods of making such magnetic nanoparticles can include, for example, those described in U.S. Pat. Nos. 5,543,158, 5,665,277, 7,052,777, 7,329,638, 7,459,145, and 7,524,630, the entire disclosure of each of which is hereby expressly incorporated by reference herein. See also Gupta et al., Biomaterials, Volume 26, Issue 18, June 2005, Pages 3995-4021, the disclosure of which is hereby expressly incorporated by reference herein.

"Fluid obstruction" shall be given its ordinary meaning and shall include without limitation a blockage, either partial or complete, that impedes the normal flow of fluid through a circulatory system, including the venous system, arterial system, central nervous system, and lymphatic system. "Vascular occlusions" are fluid obstructions that include, but are not limited to, atherosclerotic plaques, fatty buildup, arterial stenosis, restenosis, vein thrombi, cerebral thrombi, embolisms, hemorrhages, other blood clots, and very small vessels. Sometimes, fluid obstructions are generally referred to herein as "clots."

"Substantially clear" shall be given its ordinary meaning and shall include without limitation removal of all or part of a fluid obstruction that results in increased flow of fluid through the circulatory system. For example, substantially clearing the vein includes creating a pathway through or around a thrombus that blocks a blood vessel so that blood can flow through or around the thrombus.

"Very small vessel" shall be given its ordinary meaning and shall include without limitation a circulatory system fluid pathway having a diameter from about 1 μm to about 10 μm.

"Increased fluid flow" shall be given its ordinary meaning and shall include without limitation increasing the throughput of a blocked circulatory system from zero to something greater than zero. For example, in flowing circulatory systems, the term increased fluid flow can mean increasing the throughput from a level prior to administration of one or more magnetic nanoparticles in a patient to a level greater than the original fluid flow level.

"Agglomerate" shall be given its ordinary meaning and shall include without limitation rotational clustering and chaining of a group of individual magnetic rotors in a manner to develop "rods" from the magnetic nanoparticles (for example, as described herein with respect to FIG. 17). Such a group of rotating rotors forms an ensemble in which individual rotors generally rotate simultaneously and travel in the same direction as a group. The application of the combined magnetic field and gradient over time is the manner of assembling the rods. Such a group comprises characteristics that can different than what can be expected of individual rotors acting alone and can create hydrodynamic forces in a fluid stream or still fluid to create turbulence or enhance the diffusion of a composition or liquid in the fluid stream or still fluid.

"Treatment" shall be given its ordinary meaning and shall include without limitation an approach for obtaining beneficial or desired clinical results. For purposes of this disclosure, beneficial or desired clinical results include, but are not limited to, one or more of the following: improvement or alleviation of any aspect of fluid obstruction in the circulatory system including, but not limited to, fluid obstructions (e.g., stroke, deep vein thrombosis), coronary artery disease, ischemic heart disease, atherosclerosis, and high blood pressure.

"Drug, compound, or pharmaceutical composition" shall be given their ordinary meanings and shall include without limitation a chemical compound or composition capable of inducing a desired therapeutic effect when properly administered to a patient, for example enzymatic degradation of a thrombus or atherosclerotic plaque.

"Effective amount" shall be given its ordinary meaning and shall include without limitation an amount of a therapeutic agent (e.g., drug, chemical adjunct, compound or pharmaceutical composition) sufficient to effect beneficial or desired results including clinical results such as alleviation or reduction in circulatory system fluid blockage. An effective amount can be administered in one or more administrations. For example, an effective amount of drug, compound, or pharmaceutical composition can be an amount sufficient to treat (which includes to ameliorate, reduce incidence of, delay and/or prevent) fluid blockage in the circulatory system, including vascular occlusions in the head and extremities. The effective amount of a therapeutic agent can include coated or uncoated magnetic nanoparticles formulated to be administered to a patient. The effective amount may be considered in the context of administering one or more therapeutic agents, and a single agent may be considered to be given in an effective amount if, in conjunction with one or more other agents, a desirable result may be or is achieved.

"Reducing incidence" shall be given its ordinary meaning and shall include without limitation any of reducing severity (which can include reducing need for and/or amount of (e.g., exposure to) drugs and/or therapies generally used for these conditions, including, for example, tPA), duration, and/or frequency (including, for example, delaying or increasing time to displaying symptoms of circulatory system blockage). For example, individuals may vary in terms of their response to treatment, and, as such, for example, a method of reducing incidence of fluid blockage in a patient reflects administering the effective amount of the magnetic nanoparticles, whether or not in combination with a therapeutic agent, based on a reasonable expectation that such administration may likely cause such a reduction in incidence in that particular individual.

"Ameliorating" one or more symptoms of circulatory system blockage shall be given its ordinary meaning and shall include without limitation a lessening or improvement of one or more symptoms of circulatory system blockage as compared to not administering a magnetic nanoparticle, whether or not in combination with a therapeutic agent, using the system described herein. Ameliorating can also include shortening or reducing in duration a symptom.

"Delaying" the development of a symptom related to circulatory system blockage shall be given its ordinary meaning and shall include without limitation to defer, hinder, slow, retard, stabilize, and/or postpone progression of the related symptoms. This delay can be of varying lengths of time, depending on the history of the disease and/or individuals being treated. For example, a sufficient or significant delay can, in effect, encompass prevention in that the individual does not develop symptoms associated with circulatory system blockage. A method that delays development of the symptom is a method that reduces probability of developing the symptom in a given time frame and/or reduces extent of the symptoms in a given time frame, when compared to not using the method. Such comparisons may be based on clinical studies, using a statistically significant number of subjects.

"Pharmaceutically acceptable carrier" shall be given its ordinary meaning and shall include without limitation any material which, when combined with a magnetic nanoparticle and/or an active ingredient, is non-reactive with the subject's immune system and allows the active ingredient to retain biological activity. For example, pharmaceutically acceptable carriers include pharmaceutical carriers such as a phosphate buffered saline solution, water, emulsions such as oil/water emulsion, and various types of wetting agents. Examples of diluents for parenteral administration are phosphate buffered saline or normal (0.9%) saline.

"Pharmaceutically acceptable" shall be given its ordinary meaning and shall include without limitation being approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Overview of Magnetomotive Stator System and Methods for Wireless Control of Magnetic Rotors Systems and methods are described for the physical manipulation of free magnetic rotors using a remotely placed magnetic field-generating stator according to several embodiments. Some embodiments of the invention relate to the control of magnetic nanoparticles to increase contact of a therapeutic target in a circulatory system with a therapeutic agent (e.g., a pharmaceutical compound, a thrombolytic drug), which can result in increased fluid flow and the substantial clearance of fluid blockages of the circulatory system. In various aspects, the system enhances diffusion of the therapeutic agent and uses permanent magnet-based or electromagnetic field-generating stator sources. Magnetic fields and gradients can be used to act on magnetic nanoparticle agglomerates and/or magnetic thrombectomy devices to reduce circulatory system blockages, including vascular occlusions, in a patient. In various aspects, the system and methods described herein can be used to treat fluid blockages of the circulatory system in the head (in particular, the brain) and in the extremities of the body, such as the vasculature of arms and legs.

Some embodiments of the invention provide for a magnetically produced scouring process generated by magnetic nanoparticles and/or magnetically-enabled thrombectomy devices acting on fluid blockage in combination with the mechanically-enhanced dissolving or lytic process of the therapeutic agent (e.g., thrombolytic agent) that is used. In accordance with several embodiments, the magnetic actions are derived from a rotating magnetic field from an external magnet source which also provides a pulling magnetic gradient that is not rotating. This external control advantageously provides forces and actions on circulatory system blockages generally without mechanical invasion of the location. In accordance with several embodiments, the systems and methods described herein can greatly increase interaction of the therapeutic agent with the target circulatory system blockage. The interaction may leave residue that can be collected magnetically in such a way as to leave venous walls or valves undamaged in the process. Another feature of the systems and methods described herein is the ability to use drug and stirring conditions so that substantially all of the residue that is removed forms a small soft clump with the magnetic nanoparticles that can be captured by a tiny magnet on the tip of a guide wire. To achieve these features, the system can use a rotating magnetic field in combination with a directed magnetic gradient to act on magnetic nanoparticles or magnetically-enabled fluid blockage clearing devices.

In some embodiments, the rotating magnetic field is generated by mechanically rotating a strong permanent magnet having an orientation that rotates the field at the target site, and at the same time presents a steady magnetic gradient in a desired direction. In some embodiments, two or more magnetic coils can be used with appropriate phasing to provide rotating fields with a gradient. When three or more coils are used, at least two coils can have axes having some perpendicular component to each other to provide additional magnetic spatial and timing features. For instance, two coils can have perpendicular axes and one can employ current lagging the other by 90 degrees to create a rotating field at the target position. A third coil can be located and oriented to provide appropriate gradients at the target site, as well as independent functions such as modulation.

With electronic control of the currents, a wide array of fields and gradients can be applied with a large number of time-related events. The application of a rotating field with a gradient to a slurry of magnetic nanoparticles can provide a defined type of arrangement of the grouping: that is the "agglomeration" of magnetic nanoparticles that cause them to form aligned rods of approximately 2 mm in length or less.

For example, a field of about 0.02 Tesla at the target site, in combination with a gradient of about 0.4 Tesla/meter, can create an agglomeration of magnetic nanoparticles (e.g., separated nanoparticle rods of length varying approximately from one to two millimeters in length). These agglomerates can remain largely intact in vitro and in vivo, but can be sufficiently flexible to provide "soft brushing" when rotated. It has been observed that on rotation the nanoparticle rods can "walk" along a surface in a vessel, and when in contact with a fluid blockage, such as a blood clot, can remove minute particles of the clot material with the aid of the thrombolytic drug. The nanoparticle rods can softly "scrub" off fractions of the clot material continuously, in some cases without residue components of significant size. In other cases, depending on the type and location of obstruction, the delivery of therapeutic agents (e.g., thrombolytic drugs) can be timed so that the residue ends up in a soft small magnetic ball, which can be captured magnetically and removed. Ultrasound and other imaging technologies (e.g., radiography, magnetic resonance, nuclear medicine, photo acoustic, thermography, tomography) can be used to visualize the progress of such scrubbing. For example, transcranial ultrasound imaging could be used to confirm clot destruction visually in a cranial embolism or stroke. Contrast agents and other agents that enhance visualization of the magnetic nanoparticles can also be used (e.g., iodine, barium, gadolinium). The imaging technologies can transmit images to a display device to provide an operator real-time feedback so that the operator can navigate or otherwise control movement of the magnetic nanoparticles.

Using a rotating magnetic field and gradient apparatus, it has been observed that fields of 0.02 Tesla with gradients of 0.4 Tesla/meter at the target site facilitate more precise control over the rotation of a small magnetic ball approximately 1.5 mm in diameter. It has been found that with proper alignment of the magnetic gradient, the ball-like structure can be made to navigate the vessels and increase drug mixing at the blockage. In a similar manner, coatings that comprise thrombolytic agents and/or surface features can be added to enhance destruction of a blockage.

The numerical parameters used can vary, depending on the particular nature of the circulatory system blockage, the thrombolytic drug, and/or the design of the magnetically-enabled thrombectomy devices. Rotational frequencies (e.g., greater than or equal to 0.1 Hz and/or less than or equal to 100 Hz, including but not limited to from about 1 Hz to about 30 Hz, from about 3 Hz to about 10 Hz, from about 0.5 Hz to about 50 Hz, from about 1 Hz to about 6 Hz, from about 0.1 Hz to about 10 Hz, from about 5 Hz to about 20 Hz, from about 10 Hz to about 30 Hz, from about 20 Hz to about 50 Hz, from about 40 Hz to about 70 Hz, from about 50 Hz to about 100 Hz, overlapping ranges thereof, less than 5 Hz, less than 10 Hz, less than 20 Hz, less than 30 Hz, less than 40 Hz, less than 50 Hz) can be effective with a range of magnetic field magnitudes that can be generated by magnets (e.g., greater than or equal to 0.01 Tesla and/or less than 1 Tesla, including but not limited to from about 0.01 Tesla to about 0.1 Tesla, from about 0.05 Tesla to about 0.5 Tesla, from about 0.1 Tesla to about 0.6 Tesla, from about 0.3 Tesla to about 0.9 Tesla, from about 0.5 Tesla to about 1 Tesla, overlapping ranges thereof, less than 1 Tesla, less than 0.5 Tesla, less than 0.25 Tesla, less than 0.1 Tesla), all in a volume of about one cubic foot, or by coils with somewhat larger volume. Gradient strength can be greater than or equal to 0.01 Tesla/m and/or less than or equal to 10 Tesla/m, including but not limited to from about 0.01 Tesla/m to about 1 Tesla/m, from about 0.01 Tesla/m to about 3 Tesla/m, from about 0.05 Tesla/m to about 5 Tesla/m, from about 1 Tesla/m to about 4 Tesla/m, overlapping ranges thereof, less than 5 Tesla/m, less than 3 Tesla/m, less than 2 Tesla/m, less than 1 Tesla/m). The gradient direction generally centers on the center of mass for a permanent magnet, and using an electromagnet can center on one of the coils, and in combination, can center between one or more coils.

Fluid Blockages of the Circulatory System

Parts of the body where fluid blockages of the circulatory system occur include the blood vessels associated with the legs and the brain. Two major hydrodynamic properties of such blockage are observed in the vasculature: low blood flow or total blockage. In either case, existing modes of delivery of drugs for dissolving occlusions at surfaces or mechanical removal of, for example, thrombus material cannot effectively clear a degraded and impeding layer on a clot surface to be removed to allow fresh drug interaction with an underlayer. This can result in dangerous components moving downstream which can result in a more dangerous blockage or death. In a typical flow situation, there are locations where the flow does not effectively penetrate or target the intended site. In other situations, it is not possible to navigate a thrombectomy device to the target due to smallness (e.g., a very small vessel) or complexity of the three-dimensional shape of the occluded vessel.

Different thrombolytic drugs can be used in the thrombolytic process. For example, streptokinase can be used in some cases of myocardial infarction and pulmonary embolism. Urokinase can be used in treating severe or massive deep venous thrombosis, pulmonary embolism, myocardial infarction and occluded intravenous or dialysis cannulas. Tissue Plasminogen Activator ("tPA" or "PLAT") can be used clinically to treat stroke. Reteplase can be used to treat heart attacks by breaking up the occlusions that cause them.

In the case of stroke, tPA is used successfully in many cases, but in many cases the effect of the drug is to leave downstream residue in clumps large enough to cause further blockage and sometimes death. In addition, the normal thrombolytic dosage administered to patients is related to increased bleeding in the brain. In many cases, the effectiveness of chemical interaction of the thrombolytic agent with the blockage is slow and inefficient, leaving incomplete removal of the blockage. In blockages in the extremities, mechanical means of stirring and guiding the drug are limited, often difficult, and can be dangerous. In many cases, venous valves in the region of the procedure are damaged or not made blockage-free in procedures currently used. Some embodiments described herein advantageously provide new systems and methods for significant improvements in dealing with these major obstacles in treating occlusions of the blood flow.

Magnetomotive Stator System

In accordance with several embodiments, a therapeutic system is provided comprising (a) a magnet having a magnetic field and a gradient for controlling magnetic rotors in a circulatory system, and (b) a controller for positioning and rotating the field and the gradient in a manner to agglomerate and/or traverse the magnetic rotors with respect to a therapeutic target in the circulatory system. Using the therapeutic system, contact of the therapeutic target with a pharmaceutical composition in the circulatory system can be increased. In various aspects, the pharmaceutical composition can be attached to the magnetic rotor, and in other aspects can be administered to the circulatory system separate from the magnetic rotors. In certain instances, the pharmaceutical composition can be a thrombolytic drug.

Therapeutic targets of the system can include fluid obstructions such as, but not limited to, atherosclerotic plaques, fibrous caps, fatty buildup, coronary occlusions, arterial stenosis, arterial restenosis, vein thrombi, arterial thrombi, cerebral thrombi, embolism, hemorrhage, very small vessels, other fluid obstructions, or any combination of these. Therapeutic targets of the system can also include any organ or tissue of the body. For example, therapeutic targets can be targets identified for stem cell or gene therapy. In various aspects, the circulatory system is vasculature of a patient, in particular a human patient.

In various embodiments, the therapeutic system comprises a permanent magnet coupled to a motor, and the controller controls a motor to position the magnet at an effective distance and an effective plane with respect to the therapeutic target, and rotates the magnet at an effective frequency with respect to the therapeutic target. In various embodiments, the therapeutic system comprises an electromagnet having a magnetic field strength and magnetic field polarization driven by electrical current, and the controller positions the electromagnet at an effective distance and an effective plane with respect to the therapeutic target, and rotates the magnetic field of the electro-magnet by adjusting the electrical current.

The therapeutic system can further include a display for viewing the magnetic rotors and therapeutic target, and a user interface for controlling the magnetic rotors, such that a user can control the magnetic rotors to clear the therapeutic target at least in part by adjusting a frequency of the rotating magnetic field, a plane of the rotating magnetic field with respect to the therapeutic target, and/or a distance of the rotating magnetic field with respect to the therapeutic target. In various aspects, the therapeutic target can be a thrombosis in a human blood vessel. In various aspects, the magnetic rotors can be magnetic nanoparticles injected into the circulatory system.

In various aspects, the obstruction to be treated using the system is a thrombosis in a human blood vessel, and the magnetic rotors are formed by magnetic nanoparticles injected into the circulatory system. In the system, the magnetic rotors can traverse through the fluid in a generally circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

In some embodiments, a system is provided for increasing fluid flow in a circulatory system comprising a magnet having a magnetic field for controlling magnetic rotors in the fluid, a display for displaying, to a user, the magnetic rotors and the therapeutic target in the fluid, and a controller, in response to instructions from the user, controlling the magnetic field to: (a) position the magnetic rotors adjacent to the therapeutic target, (b) adjust an angular orientation of the magnetic rotors with respect to the therapeutic target, and/or (c) rotate and traverse the magnetic rotors through the fluid in a circular motion to mix the fluid and substantially clear the therapeutic target.

In various aspects, the display can display real time video of the magnetic rotors and the therapeutic target, and the display can superimpose a graphic representative of a rotation plane of the magnetic field and another graphic representative of the attractive force of the magnetic field on the real time video. In some aspects, the magnet can be a permanent magnet coupled to a motor and a movable arm, and the controller can include a remote control device for a user to manipulate the position, rotation plane and/or rotation frequency of the magnetic field with respect to the therapeutic target.

In some embodiments, the display can adjust the graphics in response to instructions received from the user through the remote control device. In various aspects, the magnet can be an electromagnet coupled to a motor and a movable arm, and the controller can perform image processing to identify the location, shape, thickness and/or density of the therapeutic target, and can automatically manipulate the movable arm to control the position, rotation plane and/or rotation frequency of the magnetic field to clear the therapeutic target.

In some embodiments, the magnetic rotors are formed by magnetic nanoparticles which combine in the presence of a rotating magnetic field. In some aspects, the fluid can be a mixture of blood and a therapeutic agent (e.g., a thrombolytic drug), the blood and therapeutic agent being mixed by the generally circular motion of the magnetic rotors to erode and clear the therapeutic target. In some aspects, the generally circular motion of the magnetic rotors can redirect the therapeutic agent from a high flow blood vessel to a low flow blood vessel which contains the therapeutic target.

Figure 1B:
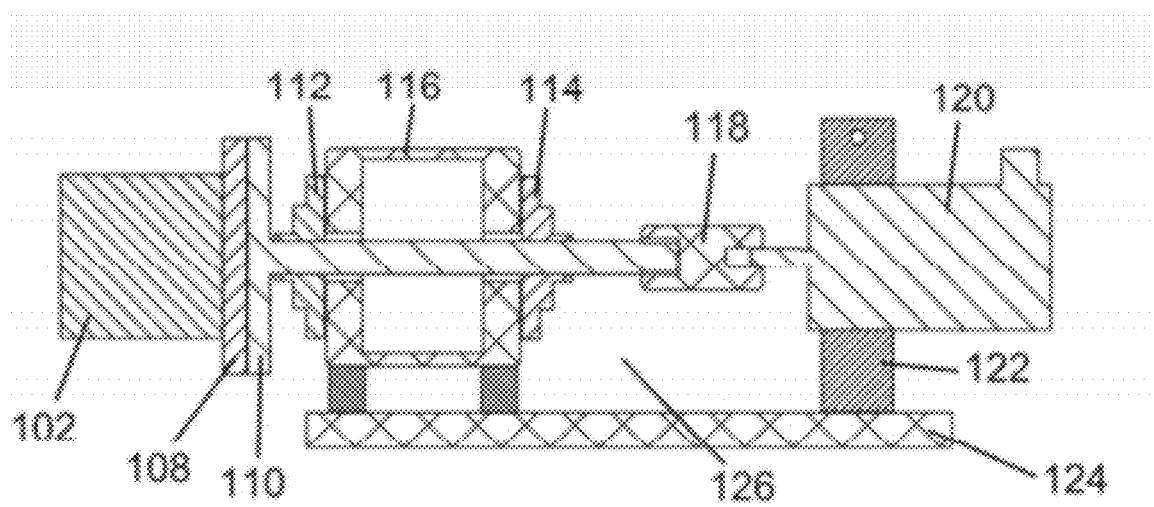

An example embodiment of a magnetomotive stator system is illustrated in FIG. 1A (isometric view) and FIG. 1B (cross-section view). The operation of components is shown for this system involving rotation about a single axis 132. The permanent magnet cube 102 possesses a North 104 and a South 106 magnetic pole. In one embodiment, the permanent magnet 102 measures 3.5 inches on each side. The permanent magnet 102 may comprise a number of permanent magnet materials, including Neodymium-Boron-Iron and Samarium-Cobalt magnetic materials, and may be made much bigger or smaller. For example, the permanent magnet 102 can be greater than or equal to 1 inch on each side and/or less than 10 inches on each side including but not limited to between about 1 inch and about 5 inches, between about 2 inches and about 6 inches, between about 3 inches and about 8 inches, between about 3 inches and about 4 inches, between about 4 inches and about 10 inches, overlapping ranges thereof, less than 6 inches, less than 5 inches, less than 4 inches. The shape of the permanent magnet 102 can be a shape other than a cube, such as, for example, a sphere, a cylinder, a rectangular solid, an ellipsoid, or some other shape. Other configurations of the permanent magnetic material may improve performance in shaping the field so that aspects of the magnetic field and gradient are improved or optimized in terms of strength and direction. In some embodiments, the permanent magnetic material may be configured in a way to make the system more compact. A cylinder comprising permanent magnetic material is one such example. Cylindrical magnets may reduce the mass of the magnet and allow the mass of the magnet to be positioned closer to the patient. However, simple rectangular and cubical geometries may be cheaper to purchase or manufacture.

The face of the permanent magnet 102 in which the North 104 and South 106 poles reside is glued, attached, bonded, affixed, welded, or otherwise fastened or coupled to a mounting plate 108. The mounting plate 108 can comprise magnetic or nonmagnetic material. Optionally, magnetic materials can be used to strengthen the magnetic field for some configurations of the permanent magnetic material. In some embodiments, nonmagnetic mounting plates can be desirable as they may be easier to affix or couple to the permanent magnet 102.

This mounting plate 108 is attached to a flange 110 that passes through a first bearing 112 and a second bearing 114, both of which are supported by the bearing mounting structure 116. Many standard bearings are at least partially magnetic. Accordingly, in some embodiments, the flange 110 is constructed from a nonmagnetic material to ensure the magnetic field does not travel efficiently from the flange 110 into the bearings 112 and 114. If this were to happen, the bearings could encounter more friction due to the magnetic attraction of the flange 110 to the bearings 112 and 114.

The end of the flange 110 is connected to a coupling 118, which connects to a drive motor 120. The motor 120 may be a DC motor or an AC motor. A high degree of precision is capable with a servo motor. In some embodiments, a step-down gearbox may be advantageously used to spin the permanent magnet 102 at the desired rotation frequency, given that many motors typically spin faster than is desired for the wireless control of magnetic rotors as described herein.

The drive motor 120 is attached to a motor support structure 122, which affixes the drive motor 120 to a platform 124. Attached to the platform 124 is a suspension mounting bracket 126 (located but not shown in FIG. 1B), which is connected to a suspension arm 128. The suspension arm 128 possesses an attachment joint 130. The suspension arm 128 may be suspended from overhead, from the side, from the bottom, or from some other location depending on a desirable placement of the magnetomotive stator system.

Operation of the Magnetomotive Stator System

Figure 2:
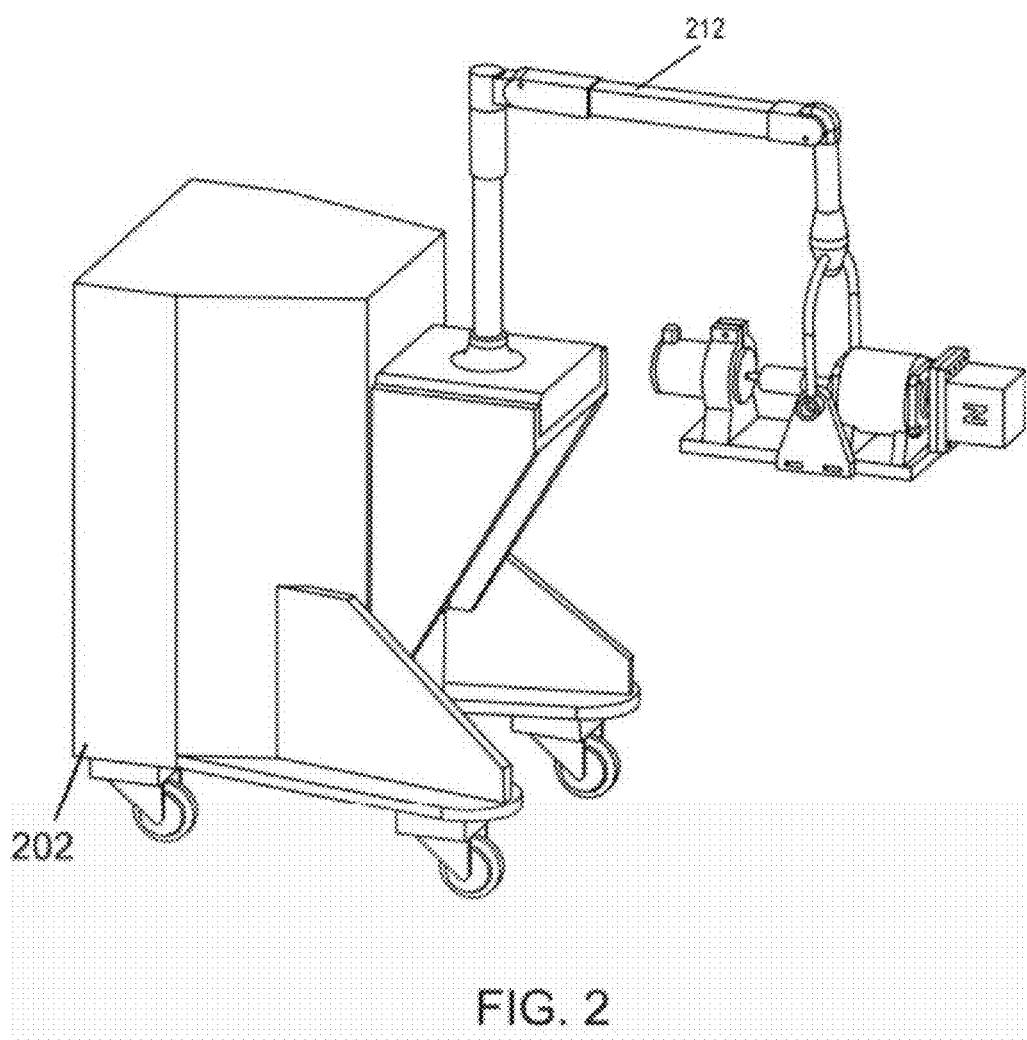
FIG. 2 illustrates a portable positioner cart to which the magnet system of FIGS. 1A and 1B can be attached.
Figure 7A:
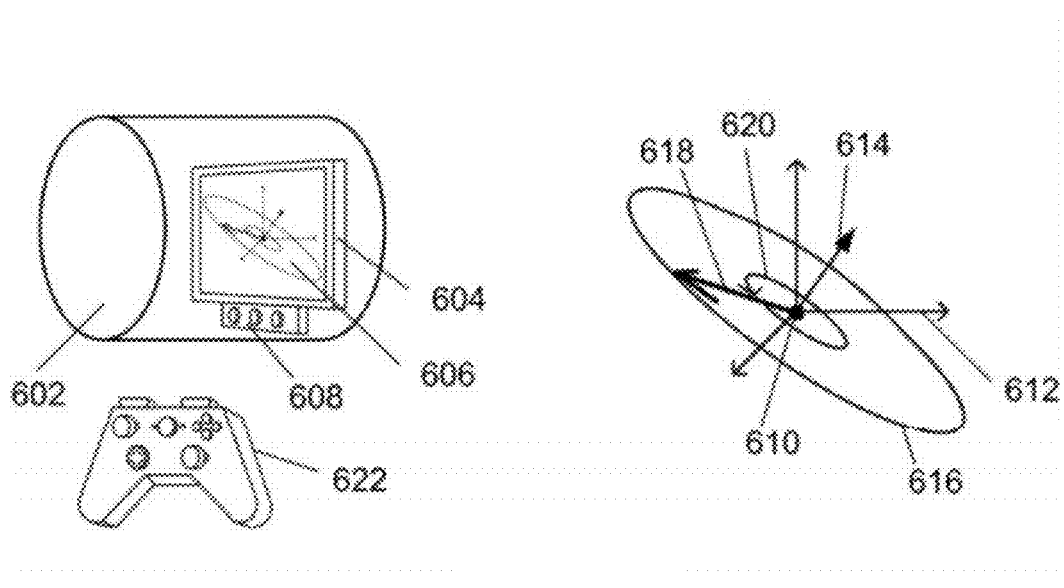
FIGS. 7A to 7C illustrate various embodiments of a user control interface for a magnetomotive stator system.
Figure 7B:
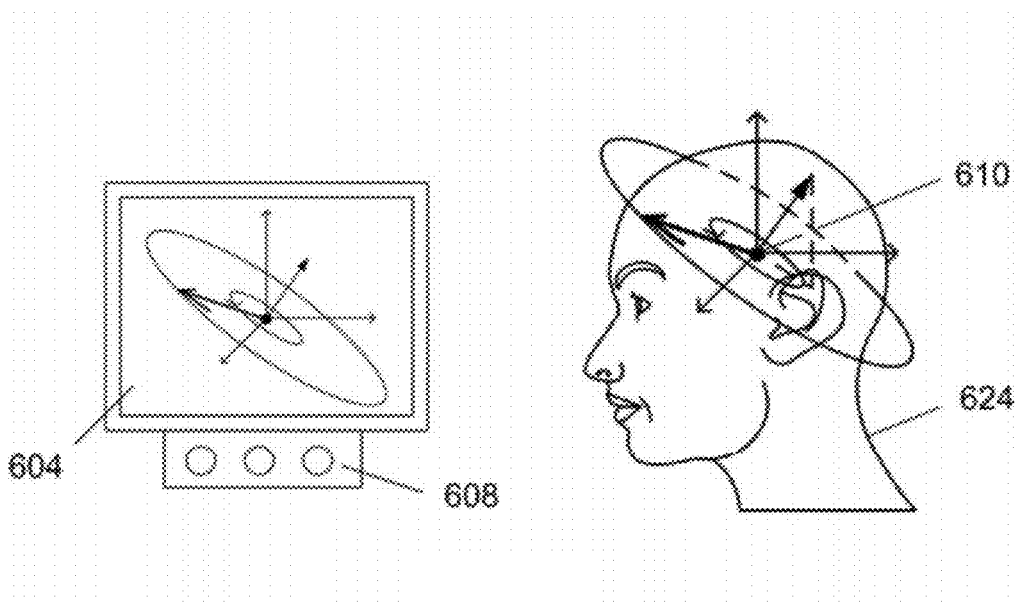
Figure 7C:
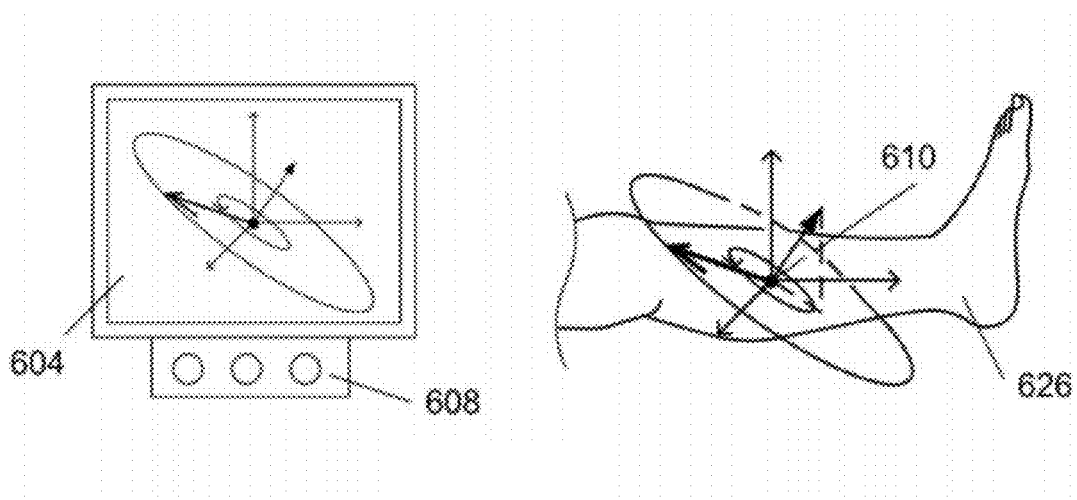

The magnetomotive stator system (e.g., magnetomotive stator system 602 of FIG. 7A) can be positioned by the use of a portable support base 202 as shown in FIG. 2. Once in place, and as shown in FIG. 7A, a computer control panel 604 with a display (e.g., computer display) 606 and user control buttons 608 are used to specify the orientation of the magnetic rotation plane 616 at the user-defined point in space 610. In some embodiments, the display 606 is a touchscreen display. The field and gradient are manipulated in the physical space 610. The rotation plane's normal vector 614 can be specified by the user in the global coordinate system 612 at the point in space 610, using the control button 608 or a handheld controller 622. Within the magnetic rotation plane 616 is the initial orientation of the magnetic field 618, which may be set automatically by the computer or manually by a user or operator. The user can specify the direction of the magnetic field rotation 620 in the magnetic rotation plane 616.

Figure 8:
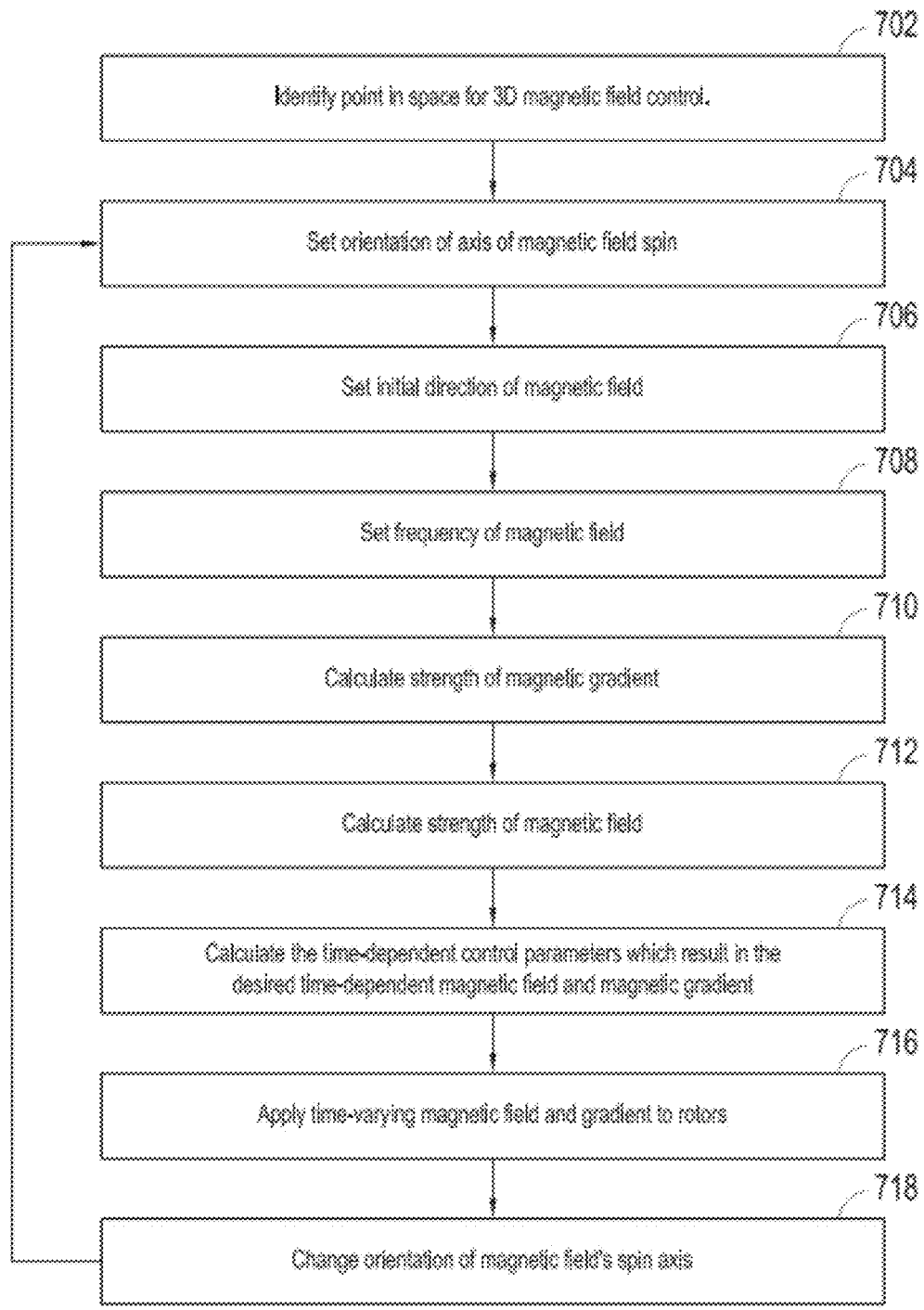
FIG. 8 illustrates an embodiment of a control process.

An embodiment of a control process is illustrated in FIG. 8. One, more, or all of the steps in the control process can be automatically performed by a computing device. One or more of the steps can be performed by an operator. At block 702, a point in space for three-dimensional control is identified. At block 704, an orientation of the axis of the magnetic field spin, which is perpendicular to the magnetic field, is set. This step can include the specification of the rotation plane's normal vector 614. Using a right-handed coordinate system, the magnetic field can rotate clockwise around the normal vector 614. At block 706, the initial direction of the magnetic field 618 is set. In some embodiments, a computer (e.g., the controller 604) can automatically set the initial direction of the magnetic field 618. At block 708, the frequency of field rotation within the magnetic rotation plane 616 is set by the user or automatically by the computer. The strength of the magnetic gradient is calculated at block 710 and the strength of the magnetic field is calculated at block 712. At block 714, control parameters are calculated for the magnetomotive system. The control parameters can determine the desired rotating magnetic field and magnetic gradient. For a permanent magnet system, the control parameters can correspond to the rotation speed of the drive motor(s) 120. For an electromagnet system, the control parameters can describe the change in current in time. Once the control parameters are calculated, the magnetomotive stator system can be turned on at block 716 and the magnetic field and gradient are applied to a target area. If it is desired or calculated that the magnetic rotation plane 616 should be changed at block 718, the control process loops back to block 704.

Assuming the magnetomotive stator system of FIG. 1A is attached to the portable support base 202, the platform 124 may be oriented by the user through the suspension mounting brackets 126 attached to the suspension arm 128, which is itself attached to the suspension arm attachment joint 130. The suspension arm attachment joint 130 connects to an arm positioner 212 connected to the portable support base 202. The suspension arm attachment joint 130 allows rotation of the magnetomotive system about the end of the arm positioner 212. The suspension arm attachment joint 130 also allows the platform base 124 to be rotated in the plane perpendicular to that allowed by the suspension arm attachment joint 130. The motor 120, which is attached to the platform base 124 via the motor support structure 122, spins at a desired frequency. This spinning, or rotating, motion is coupled to the mounting flange 110 via the drive coupling 118. The first bearing 112 and the second bearing 114 allow for the mounting flange 110 to rotate smoothly. These bearings are affixed to the platform 124 via the bearing mounting structure 116. The spinning, or rotating, flange 110 is rigidly attached to the magnet mounting plate 108, which is attached to the permanent magnet 102. Thus, the motor 120 spin is transmitted to the permanent magnet 102. The location of the North magnetic pole 104 and the South magnetic pole 106 at the ends of the permanent magnet 106 results in the desired magnetic field rotation plane 616. In this magnetic field rotation plane 616, the magnetic field rotates parallel to the front face of the magnet for all points located on the central drive axis 132.

As an example, for the manipulation of magnetic nanoparticles within the body, the user-defined point in space 610 may be inside the head 624 for ischemic stroke therapies in which magnetite nanoparticles are manipulated to rapidly and safely destroy clots. Likewise, the user-defined point in space 610 may be inside the leg 626 for deep-vein thrombosis therapies in which magnetite nanoparticles are manipulated to rapidly and safely destroy clots.

Figure 9A:
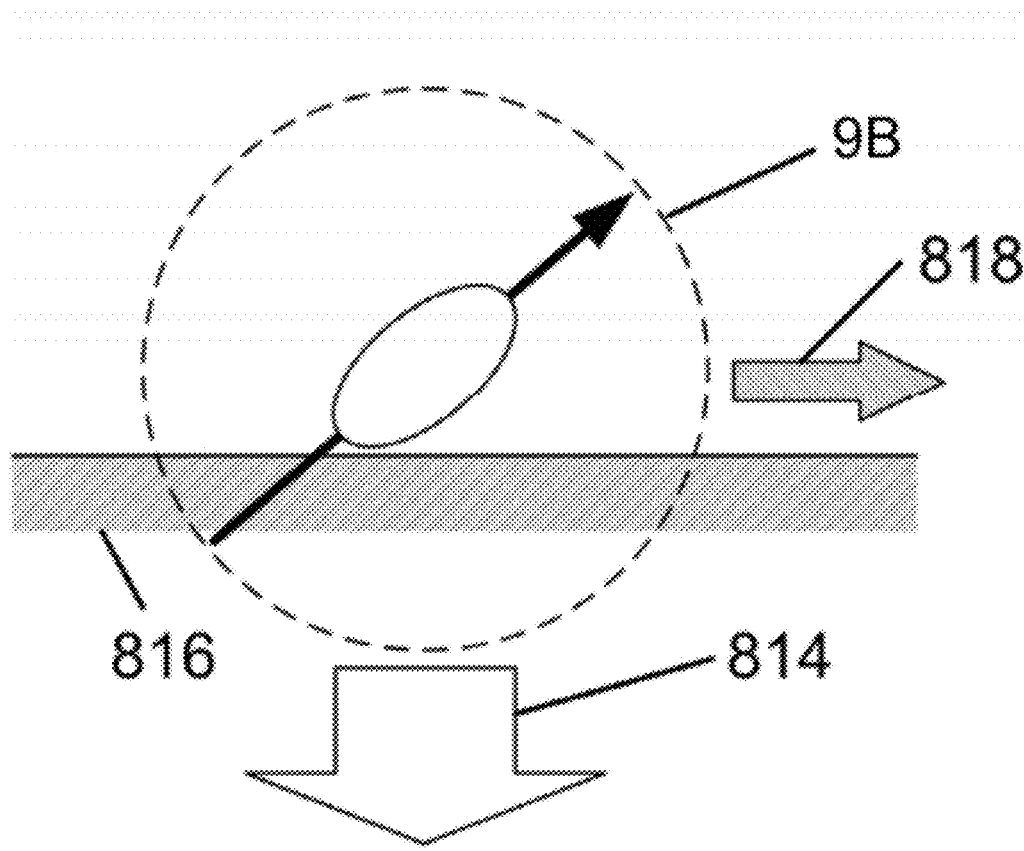
FIG. 9A illustrates the manipulation of magnetic nanoparticles to create motion within a blood vessel, in accordance with an embodiment of the invention.
Figure 9B:
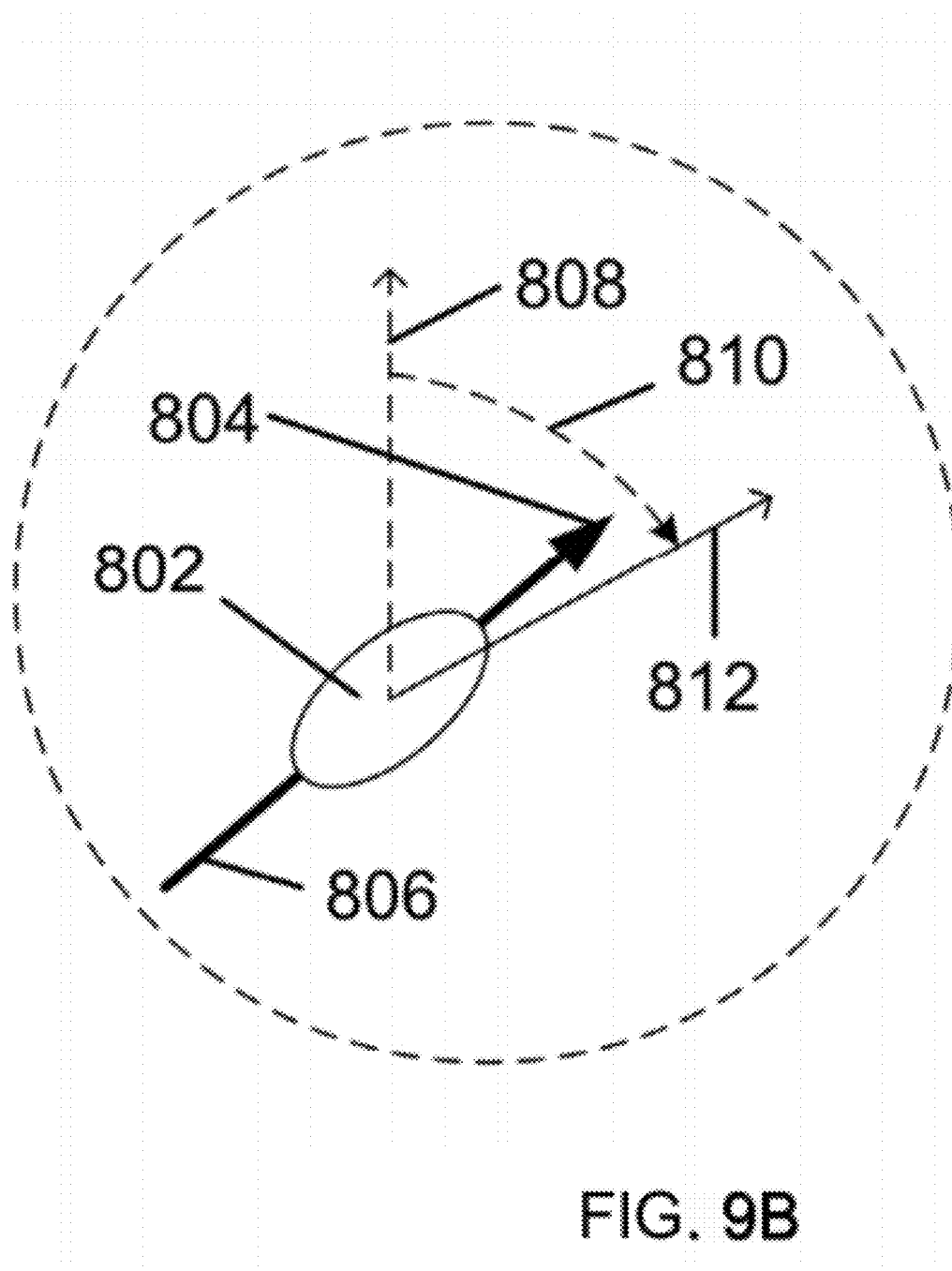
FIG. 9B illustrates the action of the magnetic field on a magnetic nanoparticle to create rotation, in accordance with an embodiment of the invention.

As an example of magnetic nanoparticle manipulation in accordance with several embodiments, FIG. 9B illustrates a magnetic nanoparticle 802, which possesses a particle North magnetic pole 804 and a particle South magnetic pole 806, that is rotated by the clockwise rotating magnetomotive-generated magnetic field 812 relative to the particle reference coordinate system 808. The rotating magnetic field 812 causes the magnetic nanoparticle to spin in the direction of the clockwise rotation angle 810. When a magnetic gradient 814 is applied and a surface 816 is present (e.g., a vessel wall), as illustrated in FIG. 9A, the clockwise rotating magnetomotive-generated magnetic field 812 results in traction against the surface 816, resulting in translation 818 parallel to the surface (e.g., to the right as shown in FIG. 9A).

Figure 9C:
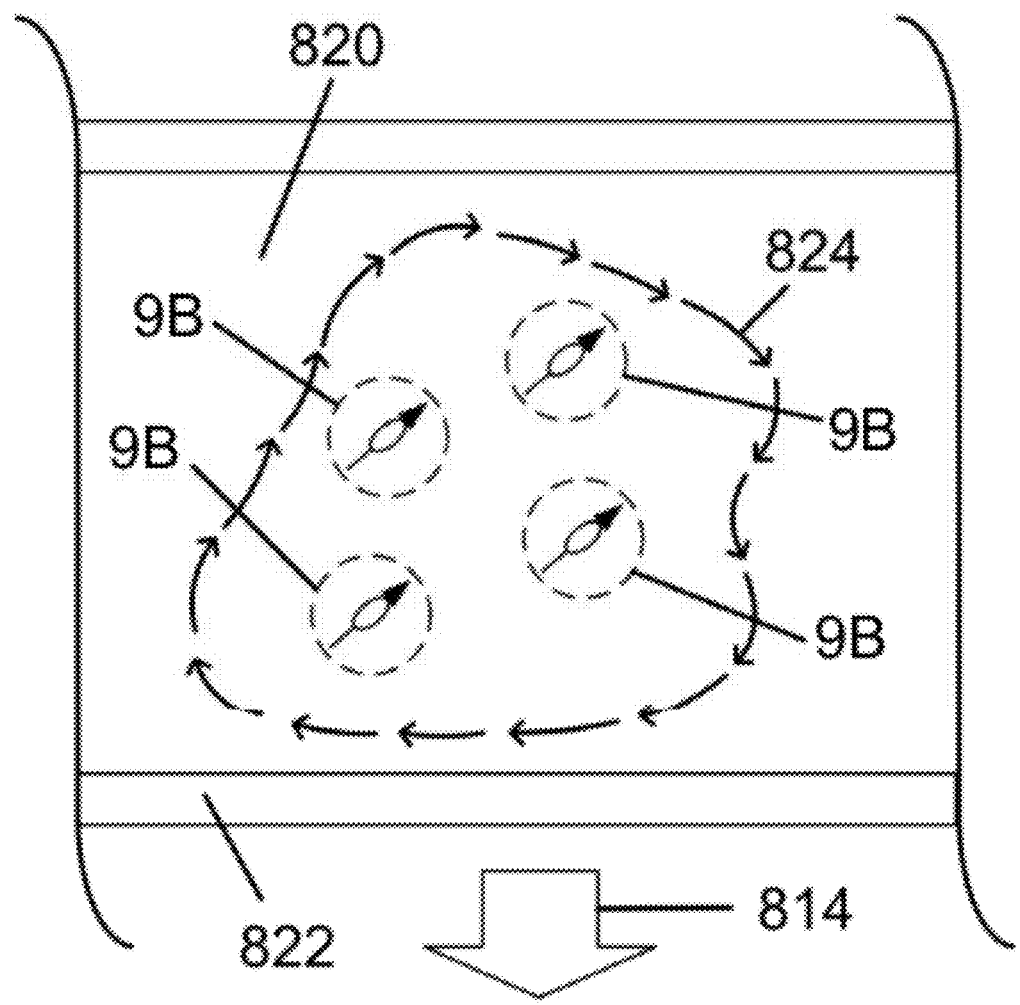
FIG. 9C illustrates the magnetic manipulation of a magnetic nanoparticle distribution inside a fluid-filled enclosure to create flow patterns, in accordance with an embodiment of the invention.
Figure 9D:
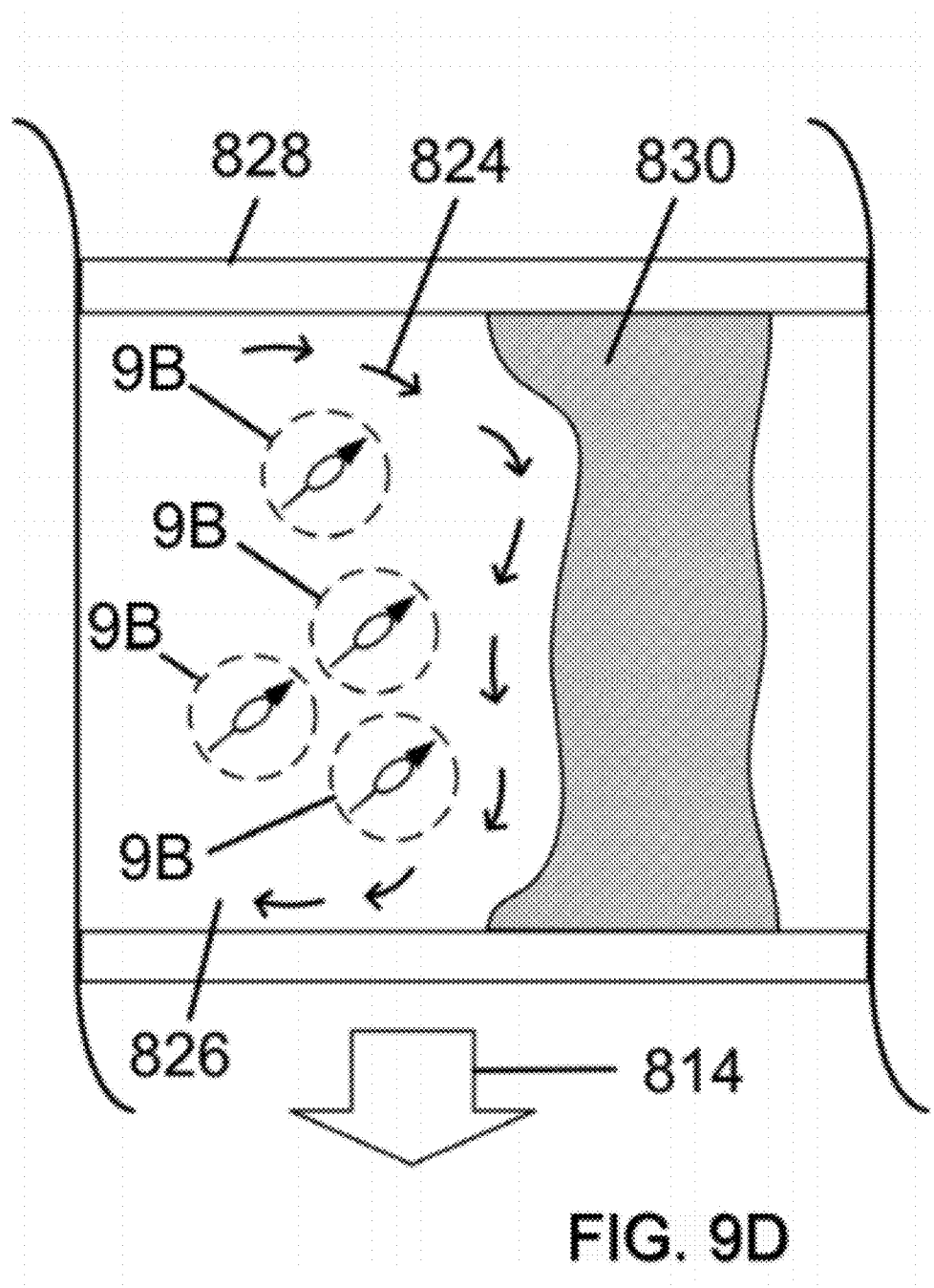
FIG. 9D illustrates the magnetic manipulation of a magnetic nanoparticle distribution to amplify the effects of therapeutic agents on a clot, in accordance with an embodiment of the invention.

In the presence of a fluid 820 contained within an enclosing region 822, as illustrated in FIG. 9C, the manipulation of the magnetic nanoparticles when combined with the magnetic gradient 814 results in circulating fluid motion 824. When used to destroy vessel obstructions 830 within a blood vessel 828, which contains blood 826 as illustrated in FIG. 9D, the magnetomotive-generated mixing can result in improved mixing of a clot-busting (thrombolytic) drug within the blood 826. The improved mixing facilitates increased contact and interaction of the therapeutic agent with the vessel obstructions 830 than would occur if the fluid was stagnant and not mixed, which advantageously allows for the dose of the thrombolytic drug to be lowered from standard prescribed doses which, by reducing the bleeding associated with higher doses of thrombolytic drugs, results in a safer procedure. It also speeds the thrombolytic process. For example, the magnetic nanoparticles can be manipulated to form a vortex, e.g. predictably circulate, in a region of stagnant flow so that the thrombolytic drug is better mixed, resulting in a more efficient chemical interaction. Creating a vortex can also draw in more of the thrombolytic drug near the region of turbulent flow.

Methods are also provided for increasing fluid flow in a circulatory system comprising: (a) administering a therapeutically effective amount of magnetic rotors to the circulatory system of a patient in need thereof, and (b) applying a magnet to the patient, the magnet having a magnetic field and a gradient for controlling the magnetic rotors in a circulatory system, and (c) using a controller for positioning and rotating the field and the gradient in a manner to agglomerate and move the magnetic rotors with respect to a therapeutic target in the circulatory system of the patient, wherein contact of the therapeutic target with a pharmaceutical composition in the circulatory system is increased and fluid flow is increased.

The pharmaceutical composition, according to some embodiments, can be attached to the magnetic rotor. In some aspects, the pharmaceutical composition can be administered to the circulatory system of the patient separate from the magnetic rotors. In various embodiments, the pharmaceutical composition is a thrombolytic drug.

In various embodiments, a therapeutic target can be a fluid obstruction such as atherosclerotic plaques, fibrous caps, fatty buildup, coronary occlusions, arterial stenosis, arterial restenosis, vein thrombi, arterial thrombi, cerebral thrombi, embolism, hemorrhage and very small vessel. In some aspects, the circulatory system is vasculature of a patient, particularly a human patient.

In certain embodiments, the magnet can be a permanent magnet coupled to a motor, and the controller can control a motor to position the magnet at an effective distance, an effective plane with respect to the therapeutic target, and can rotate the magnet at an effective frequency. In some aspects, the magnet can be an electromagnet having a magnetic field strength and magnetic field polarization driven by electrical current, and the controller can position the electromagnet at an effective distance, an effective plane with respect to the therapeutic target, and can rotate the magnetic field of the electro-magnet by adjusting the electrical current.

The system of the method can further include a display for viewing the magnetic rotors and therapeutic target, and a user interface for controlling the magnetic rotors, wherein a user controls the magnetic rotors to increase contact of the therapeutic target with a pharmaceutical composition in the circulatory system by adjusting a frequency of the rotating magnetic field, a plane of the rotating magnetic field with respect to the therapeutic target, and/or a distance of the rotating magnetic field with respect to the therapeutic target.

In various aspects, the therapeutic target can be a thrombosis in a human blood vessel. In some aspects, the magnetic rotors can be magnetic nanoparticles injected into the circulatory system. In particular, the therapeutic target can be a full or partial blockage of a vein bivalve. In certain aspects, the magnetic rotors move through the fluid in the circular motion by repeatedly (a) walking end over end along the blood vessel away from the magnetic field in response to the rotation of the rotors and an attractive force of the magnetic field, and (b) flowing back through the fluid towards the magnetic field in response to the rotation of the rotors and the attractive force of the magnetic field.

In various aspects, the rotor is a magnetic nanoparticle of a diameter from about 20 nm to about 60 nm. In some aspects, the therapeutic target is a vascular occlusion in the patient's head or a vascular occlusion in the patient's leg.

In some embodiments, a method is provided for increasing drug diffusion in a circulatory system comprising (a) administering a therapeutically effective amount of magnetic rotors to the circulatory system of a patient, and (b) applying a magnet to the patient, the magnet having a magnetic field and a gradient for controlling the magnetic rotors in a circulatory system, and (c) using a controller for positioning and rotating the field and the gradient in a manner to agglomerate and move the magnetic rotors with respect to a therapeutic target in the circulatory system of the patient, wherein diffusion of a pharmaceutical composition in the circulatory system at the therapeutic target is increased.

Real-Time Control with Imaging

In some embodiments, the system provides real-time information for improved control of the magnetic nanoparticles. The magnetic nanoparticles can be configured to be detectable with an imaging modality. For example, the magnetic nanoparticles may be attached to a contrast or nuclear agent to be visible using an x-ray-based system or PET scanner, respectively. Other imaging modalities can include nuclear magnetic resonance spectroscopy, magnetic resonance imaging, computed tomography, and/or Doppler (e.g., transcranial Doppler) which may detect the fluidic current created by the magnetic nanoparticles. Ultrasound-based diagnostic imaging modalities may also be used.

Combining the control system with an imaging system can advantageously provide the ability to improve directed therapy. In some implementations, the imaging system can provide information suitable for tracking the infusion of a therapeutic agent (e.g., chemical adjunct) in real-time toward therapeutic targets (e.g., low-blood-flow lumens having one or more partial or complete obstructions or blockages). For example, magnetic nanoparticles can be configured to act as contrast agents in applications where magnetic nanoparticles are associated with one or more drugs or therapeutic agents. Using magnetic nanoparticles in such applications allows the nanoparticles to be used as a measure of drug diffusion. Based on imaging data, the control system can correlate a concentration of the contrast agent with an amount of magnetic nanoparticles at a location. As a result, parameters of the therapy can be adjusted to alter diffusion of the drug or therapeutic agent (e.g., by altering the manipulation of the magnetic nanoparticles by adjusting the control parameters of the magnetic-based control system).

In certain embodiments, the imaging system can provide information to the system and/or a user suitable for switching the system between operational modes. For example, the imaging system can provide images to the control system indicating the location and concentration of magnetic nanoparticles within a subject. Based on this information, the system or a user can cause the magnetic system to provide magnetic fields configured to collect magnetic nanoparticles in a defined location or cause the magnetic system to provide magnetic fields configured to mix or vortex magnetic nanoparticles in a location. By manipulating the magnetic system according to received image information, the control system can control the infusion of magnetic nanoparticles in response to conditions within the subject and in one, two, or three dimensions, thereby improving the ability to direct the therapy.

The imaging modality can be any imaging modality capable of resolving a device or chemical agent which is affected by the fluidic current generated by the magnetic nanoparticles. The modality could be able to image the area of interest and provide metric information. The system can include a communication module for communicating imaging data to an external device, such as a display device and/or storage device. The system can include a registration module for registering the reference frame of the image to the reference frame of the magnetic system. The system can then receive the image, register the image, track the magnetic nanoparticles, and provide a means of directing the nanoparticles to be navigated along a desired path, either by an operator or automatically by a computer controller. The imaging data can be two-dimensional or three-dimensional. Three-dimensional information could be advantageous where navigation occurs in three dimensions. In some embodiments, the control of the magnetic nanoparticles can occur remotely using the systems described herein.

Figure 10:
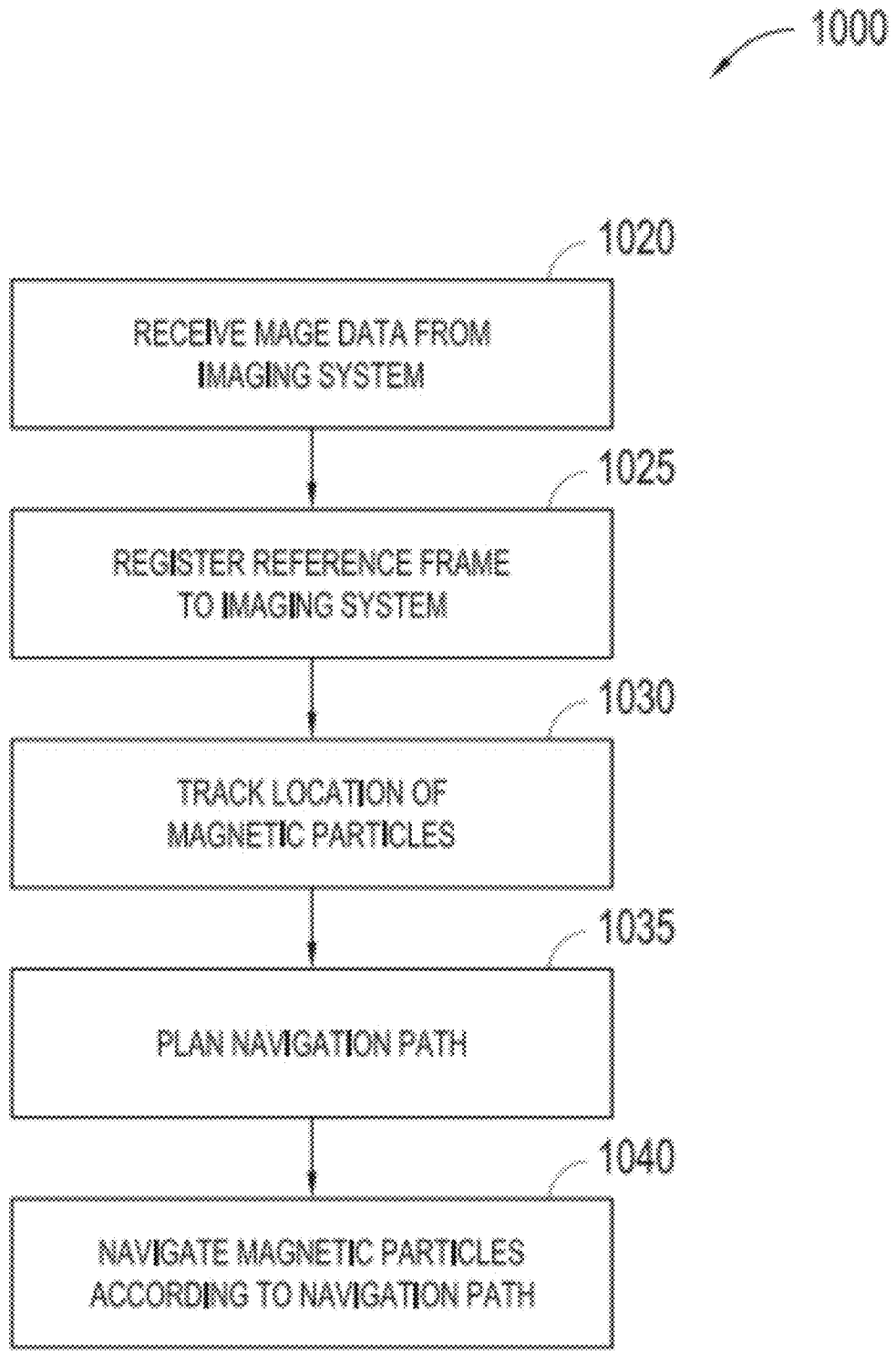
FIG. 10 illustrates an embodiment of a method for controlling magnetic nanoparticles.

FIG. 10 illustrates a flow chart of an embodiment of a process 1000 for controlling magnetic nanoparticles. At block 1020, the system accepts the imaging data from the imaging system. Accepting the imaging data can include receiving the information from the imaging system. In some implementations, the system can request an image and/or direct the imaging system to provide an image at a defined time and/or location.

At block 1025, the system registers its reference frame to that of the imaging system. The imaging system can provide information regarding the position and orientation of the system to aid in registering the reference frames. Registering the reference frames can include identifying or detecting features in an image and comparing them to previous images to properly align the reference frames.

At block 1030, the system tracks the magnetic nanoparticles. As described above, the magnetic nanoparticles can include a coating or chemical agent that makes them detectable for a given imaging modality. Using the images received from the imaging system, the control system can identify the location of the magnetic nanoparticles. The current location of the magnetic nanoparticles can be compared to previous nanoparticles and the position of the magnetic nanoparticles can be tracked over time.

At block 1035, the system plans or determines a navigation path. Planning the navigation path can be automatic and/or based on information received from a user. The navigation path can be based, at least in part, on the imaging data received from the imaging system, patient characteristics, characteristics of the magnetic nanoparticles, the location of the therapeutic target, characteristics of the therapeutic target, the injection site, or any combination of these factors.

At block 1040, the system navigates the magnetic nanoparticles according to the navigation plan by positioning the rotating magnet so that the rotating magnetic field is oriented properly with respect to a direction of travel and to a therapeutic target site. As described above, positioning the rotating magnet can include automatic positioning by a computer controller or manual positioning by an operator. The position of the magnets and/or electromagnets can be controlled in one, two, or three dimensions and the orientation of the magnets can be controlled along one, two, or three axes as well. In addition, the system can change the strength of the magnetic field and/or magnetic gradient and the variation of the magnetic field and/or gradient, to direct the movement and behavior of the magnetic nanoparticles.

Additional Embodiments of the Magnetomotive Stator System

Figure 3:
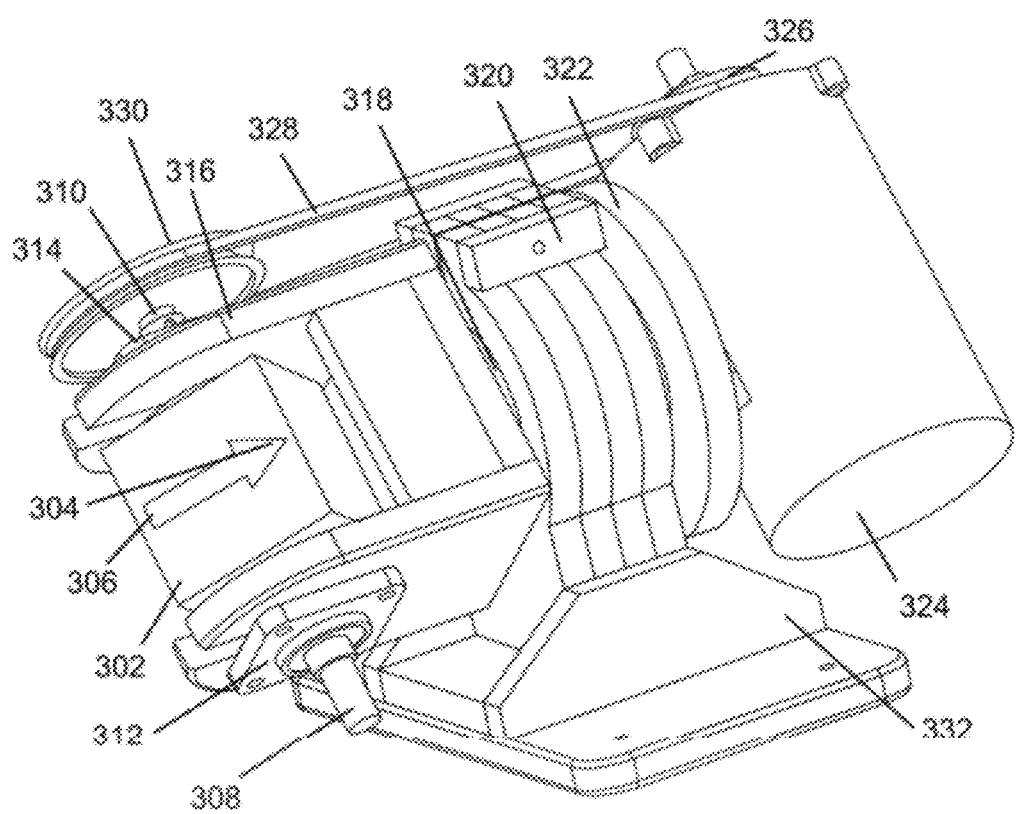
FIG. 3 illustrates an example of a permanent-magnet stator system whose magnet's North-South pole rotates in a plane perpendicular to the system's front face, which is driven by a single motor.

FIG. 3 depicts an embodiment in which the magnet is made to spin in a plane that is perpendicular to that shown in FIG. 1. Here the permanent magnet 302, which possesses a North magnet pole 304 and a South magnet pole 306, possesses two support flanges. The first magnet flange 308 passes through the first bearing 312 and the second magnet flange 310 passes through the second bearing 314. The bearings are supported by a magnet support structure 316. The magnet support structure is connected to a center shaft 318, which is supported by the support 320 for the center shaft. The center shaft 318 is attached to the motor mounting plate 322, to which is attached the drive motor 324. In this embodiment, the magnet drive motor sheave 326 is connected to the drive belt 328. The drive belt 328 is connected to the magnet sheave 330. The support for the center shaft 320 is attached to the magnet assembly support structure 332.

In some embodiments, the permanent magnet 302 is made to spin in the plane perpendicular to the front face so that the North magnet pole 304 and South magnet pole 306 rotate in the same plane. The drive motor 324 turns the motor sheave 326, which turns the drive belt 328. The drive belt 328 then turns the magnet sheave 330, which is attached to the second magnet flange 310. The first magnet flange 308 and second magnet flange 310 pass through the first bearing 312 and second bearing 314, respectively. Both magnet flanges 308 and 310 are attached to the permanent magnet 302, thus allowing the drive motor 324 to spin the permanent magnet 302.

Figure 4A:
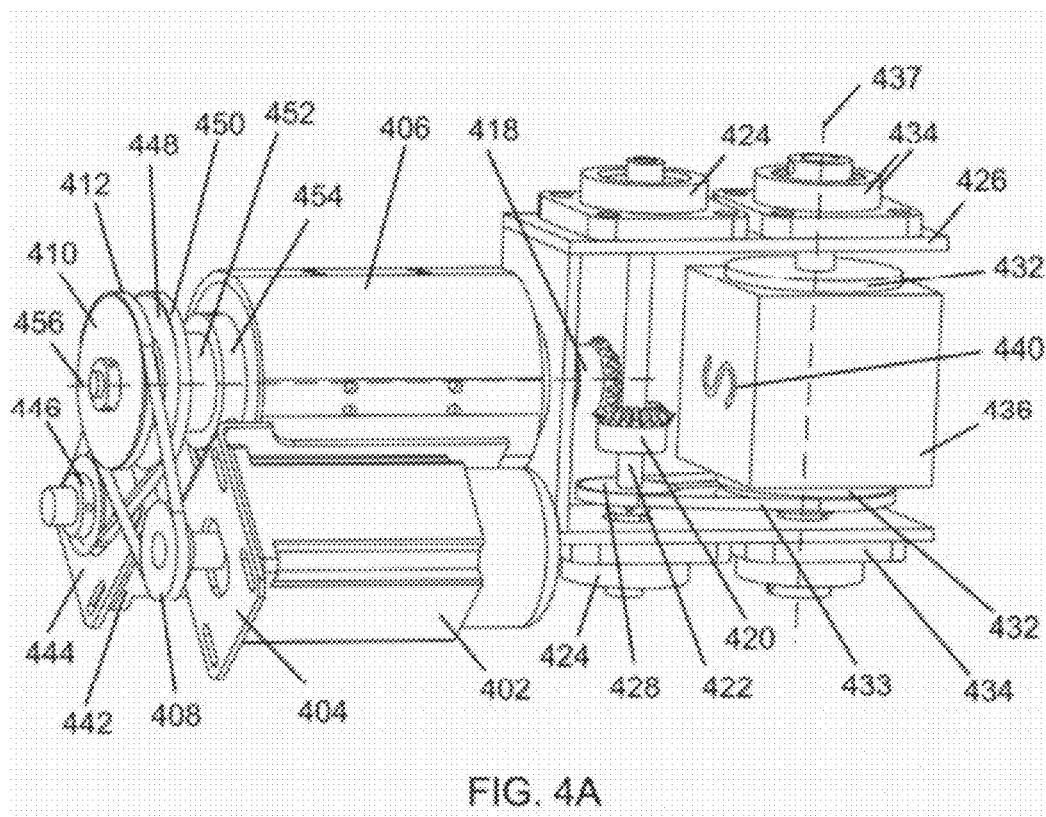
FIGS. 4A and 4B illustrate an example of a permanent-magnet stator system driven by two motors, allowing the magnet to be rotated in any plane.
Figure 4B:
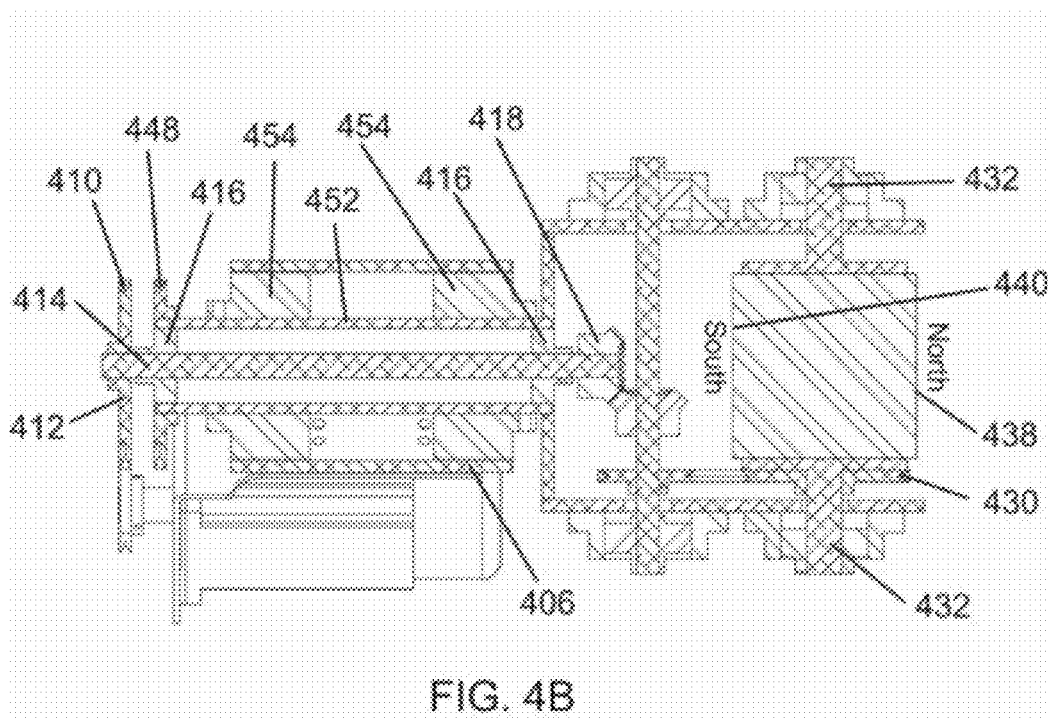

In FIGS. 4A and 4B, an embodiment of a permanent magnet 436 is depicted that is capable of being rotated in any plane using a two-motor system. The magnet possesses a North magnet pole 438 and a South magnet pole 440. The first motor 402 is attached to the central support 406 via the first motor flange 404. Attached to the first motor 402 is the first motor pulley 408. The first motor pulley 408 is connected to the first axle pulley 410 via the first motor belt 412. The first axle pulley 410 is attached to the first axle 414 which passes through the first axle bearings 416. At the end of the first axle 414 is the first miter gear 418. The first miter gear 418 engages the second miter gear 420. The second miter gear 420 is attached to the second miter gear axle 422, which passes through the second miter gear bearings 424. The second miter gear bearings 424 are attached to the magnet support yoke 426. The second miter gear pulley 428 is connected to the second miter gear axle 422. The second miter gear axle 422 is connected to the magnet pulley 430 by the magnet belt 433. The magnet pulley 430 is attached to one of the two magnet flanges 432. The magnet flanges 432 pass through the magnet bearings 434. A second motor 442, which is attached to the central support 406 by a second motor flange 444, which possesses a second motor pulley 446. The second motor pulley 446 is connected to the second axle pulley 448 by the second motor belt 450. The second axle pulley 448 is connected to the second axle 452, which passes through second axle bearings 454.

In this embodiment, the first motor 402 turns the first motor pulley 410, which transmits the rotation of the first motor pulley 410 to the first axle pulley 410 via the first motor belt 412. The first axle pulley 410 turns the first axle 414, which is made free to turn using the first axle bearings 416. Turning the first axle 414 results in the turning of the first miter gear 418, which is connected to the first axle 414. The first miter gear 418 transmits the rotation to the second miter gear 420, which turns the second miter gear axle 422. The turning of the second miter gear axle 422 is made possible using the second miter gear bearings 424. The turn of the second miter gear axle 422 results in the turning of the second miter gear pulley 428, which turns the magnet pulley 430 via the magnet belt 433. The magnet pulley 430 turns the magnet flanges 432, which results in a turn of the magnet 436 around a first axis.

The second motor 442 turns the second motor pulley 446, which turns the second axle pulley 448 via the second motor belt 450. The turning of the second axle pulley 448 results in the turning of the second axle 452, which is made free to rotate using the second axle bearings 454, thus allowing the magnet 436 to be rotated around the second axis.

Figure 5:
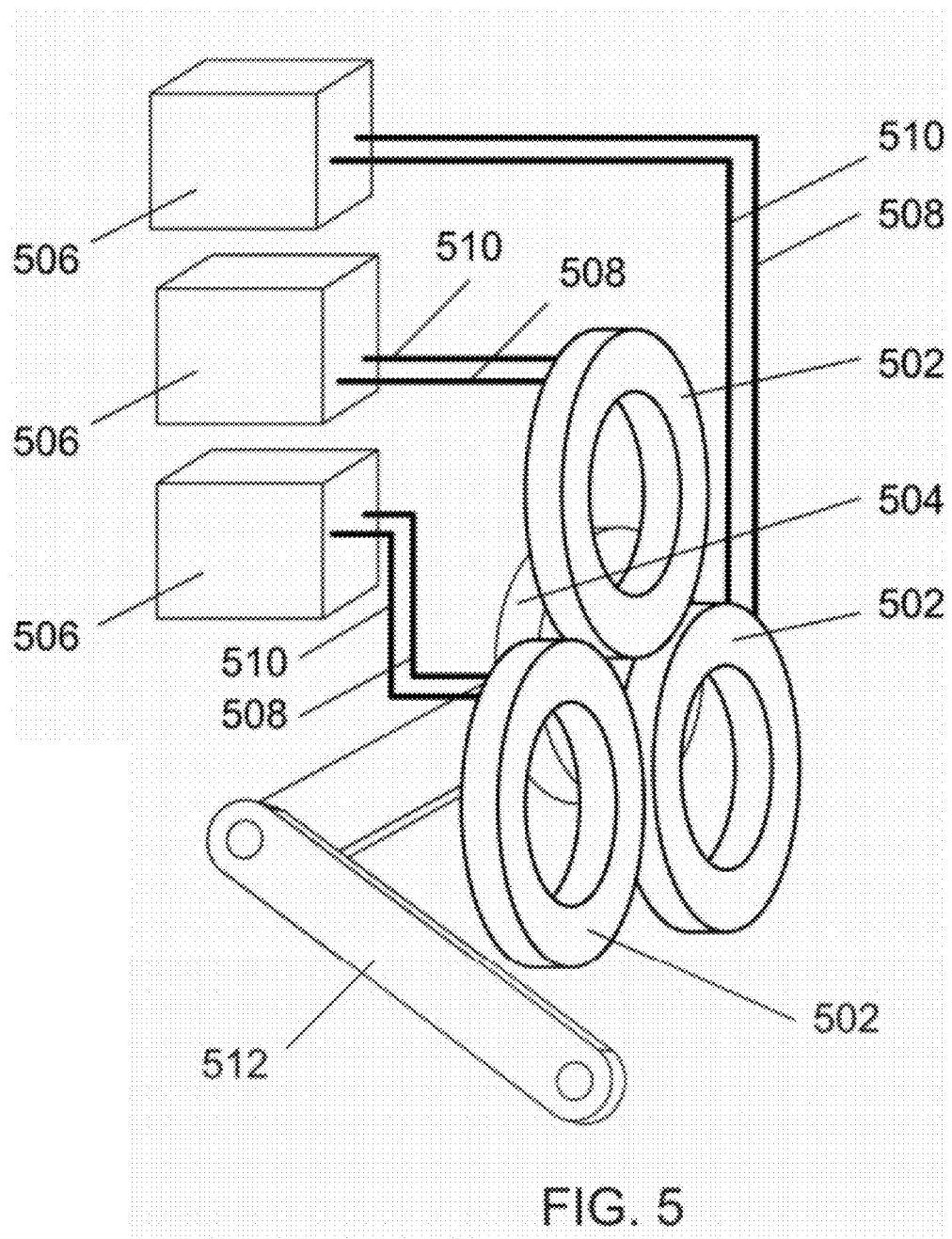
FIG. 5 illustrates an example of a three-electromagnet stator system, with power supplies, attached to an arm positioner.

FIG. 5 is an embodiment of a magnetomotive system comprising electromagnetic coils 502. The electromagnetic coils 502 are attached to a support structure 504. Electromagnetic coils 502 can be connected to power supplies 506 via power supply cables 508 and power supply return cables 510. The support structure is connected to a two-segment arm positioner 512. In the illustrated embodiment, power supplies 506 deliver power to electromagnetic coils 502 via the power supply cables 508 and the power supply return cables 510. The two-segment arm positioner 512 allows the support structure 504 to be positioned in space. In some embodiments, the power supplies 506 control the amount of electric current that is generated within the electromagnetic coils 502.

Robotic Arm

In some embodiments, an arm positioner (e.g., arm positioner 212 and the two-segment arm positioner 512) can couple the magnet system to a base (e.g., portable base 202). The arm positioner can be a robotic arm capable of positioning and orienting the magnetomotive system without being constrained by movement along one or two axes. The arm positioner can provide universal movement. The arm positioner can include motors or other mechanical actuators that allow the arm to be controlled by an electrical system or by a remote control. For example, the mechanical control system can allow an operator to control the position of the magnetic system in one, two, or three dimensions through a remote control, computer, electrical controls, or the like. In this way, the operator can manipulate the position and orientation of the magnet(s) in addition to manipulating the strength and/or variation of the magnetic field. In some embodiments, the arm positioner can be used in conjunction with the magnetomotive systems depicted in FIGS. 1, 3, and 4. In some embodiments, the position of the magnets is controlled through other electrical means in addition to or as an alternative to the arm positioner, such as with cables, rails, motors, arms, or any combination of these. In some embodiments, the position and orientation of the magnets is controlled at least in part through a five-axis robotic arm. In some embodiments, the arm positioner provides movement with six degrees of freedom. In certain embodiments, the electrical control of the position of the magnets can be included in a system having a display coupled to an imaging modality and computer control such that the operator can control the infusion and navigation of magnetic nanoparticles in real-time in response to the display and imaging of the patient.

In some embodiments, the robotic arm can be automatically manipulated by the magnetomotive system. Automatic manipulation allows the magnetomotive system to stow the magnetic system in a substantially shielded enclosure, thereby substantially reducing or preventing magnetic fields of one or more magnets of the system from having an effect on persons or items outside the system. For example, the system can include an enclosure made out of a suitable shielding material (e.g., iron). The automatic manipulation provided by the controller can move the one or more magnets of the system into the shielded enclosure when not in use.

Portable Magnet Pod with Rail Attachment

Figure 6:
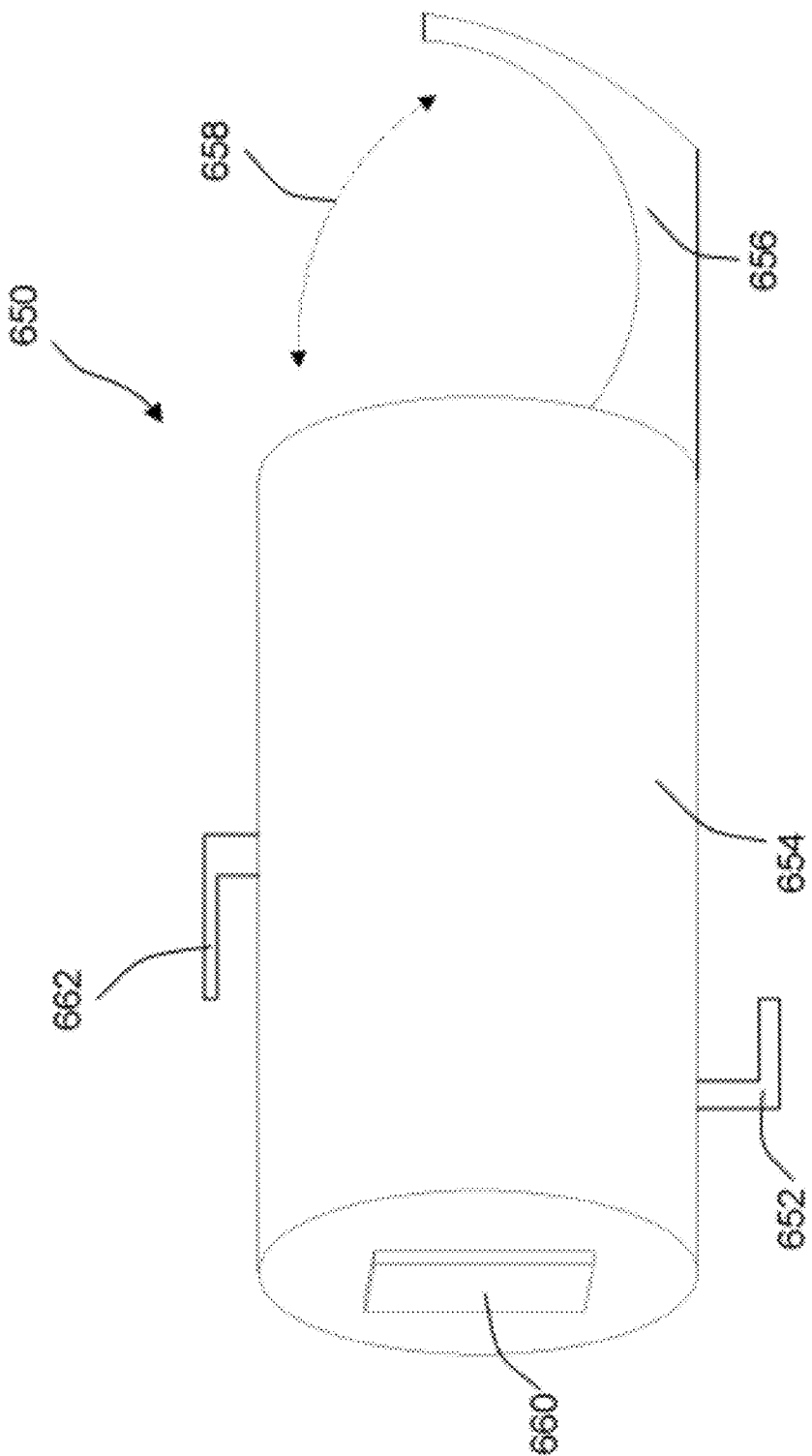
FIG. 6 illustrates an embodiment of a portable magnetic pod with a rail attachment capable of being attached to a bedside rail of a bed.

FIG. 6 illustrates a schematic drawing of an embodiment of a portable magnet pod 650 with a rail attachment 652. The portable magnet pod 650 can be designed to be carried by and secured (detachably or fixedly) to a patient bed or transport device, for example, in a hospital, urgent care facility, at home, in an ambulance, in a helicopter, or in another emergency vehicle. The portable magnet pod 650 can be used to control magnetic rotors within the patient in a manner similar to that described herein with reference to the various magnetomotive and magnetic systems.

In some embodiments, a portable magnet pod 650 includes a magnet pod 654 configured to house permanent magnets and/or electromagnets, and the associated electrical and/or mechanical support and control elements for creating a desired magnetic field. The electrical and/or mechanical components can be similar to those described herein with reference to the various magnetomotive stator systems. The portable magnet pod 650 can include controls 660 configured to operate the portable magnet pod 650, for example, allowing an operator to manipulate a desired magnetic field to control magnetic nanoparticles injected into a patient.

The portable magnet pod 650 can include a rail attachment 652 attached (detachably or fixedly) to the magnet pod 654 to provide stability. In some embodiments, the rail attachment 652 eliminates a need for setting of the patient's supine, or head elevation, angle. The rail attachment 652 can substantially secure the pod to the rail of a bed, gurney, stretcher or other patient transport device. In situations where the portable magnet pod is used for a patient suffering a stroke or has a clot or obstruction in a blood vessel leading to the brain, the attachment of the portable magnet pod 650 to a rail can ensure that the magnetomotive system is properly aligned with the central axis of the head and properly positioned aside the affected hemisphere of the brain. The portable magnet pod 650 can include a handle 662 configured to allow a user to conveniently carry the portable magnet pod 650 to a desired location.

The portable magnet pod 650 can include an integral folding headrest 656 attached (e.g., pivotably) to the magnet pod 654. The headrest 656 can be pivoted open when being used on a patient (represented by line 658). In the open position, the headrest can aid the operator in properly aligning the patient and the magnet(s). This can simplify the operation and/or control of a magnetic control system by ensuring that the patient's head is at a defined distance and attitude with respect to the rotating magnet(s). The headrest can be closed for convenience and ease while transporting the system. In some embodiments, the portable magnetic pod includes a dispensable cover for hygienic purposes.

Magnetic Tool Rotors

In some embodiments, a therapeutic system is provided for increasing fluid flow in a circulatory system comprising a magnet having a magnetic field for controlling a magnetic tool in the fluid, and a controller positioning and/or rotating the magnetic field with respect to the therapeutic target to rotate an abrasive surface of the magnetic tool and maneuver the rotating abrasive surface to contact and increase fluid flow through or around the therapeutic target. In various aspects, the circulatory system can be vasculature of a patient, particularly a human patient. In various aspects, the magnetic tool can be coupled to a stabilizing rod, wherein the magnetic tool rotates about the stabilizing rod in response to the rotating magnetic field. In some aspects, the magnetic tool can include an abrasive cap affixed to a magnet which engages and cuts through the therapeutic target. In certain aspects, the controller positions the magnetic tool at a target point on the therapeutic target, and rotates the magnetic tool at a frequency sufficient to cut through the therapeutic target. In some aspects, the magnet can be positioned so that poles of the magnet periodically attract the opposing poles of the magnetic tool during rotation, and the magnetic tool is pushed towards the therapeutic target by a stabilizing rod upon which the magnetic tool rotates. In some aspects, the magnet can be positioned so that the poles of the magnet continuously attract the opposing poles of the magnetic tool during rotation, and the magnetic tool is pulled towards the therapeutic target by an attractive force of the magnet.

Figure 11:
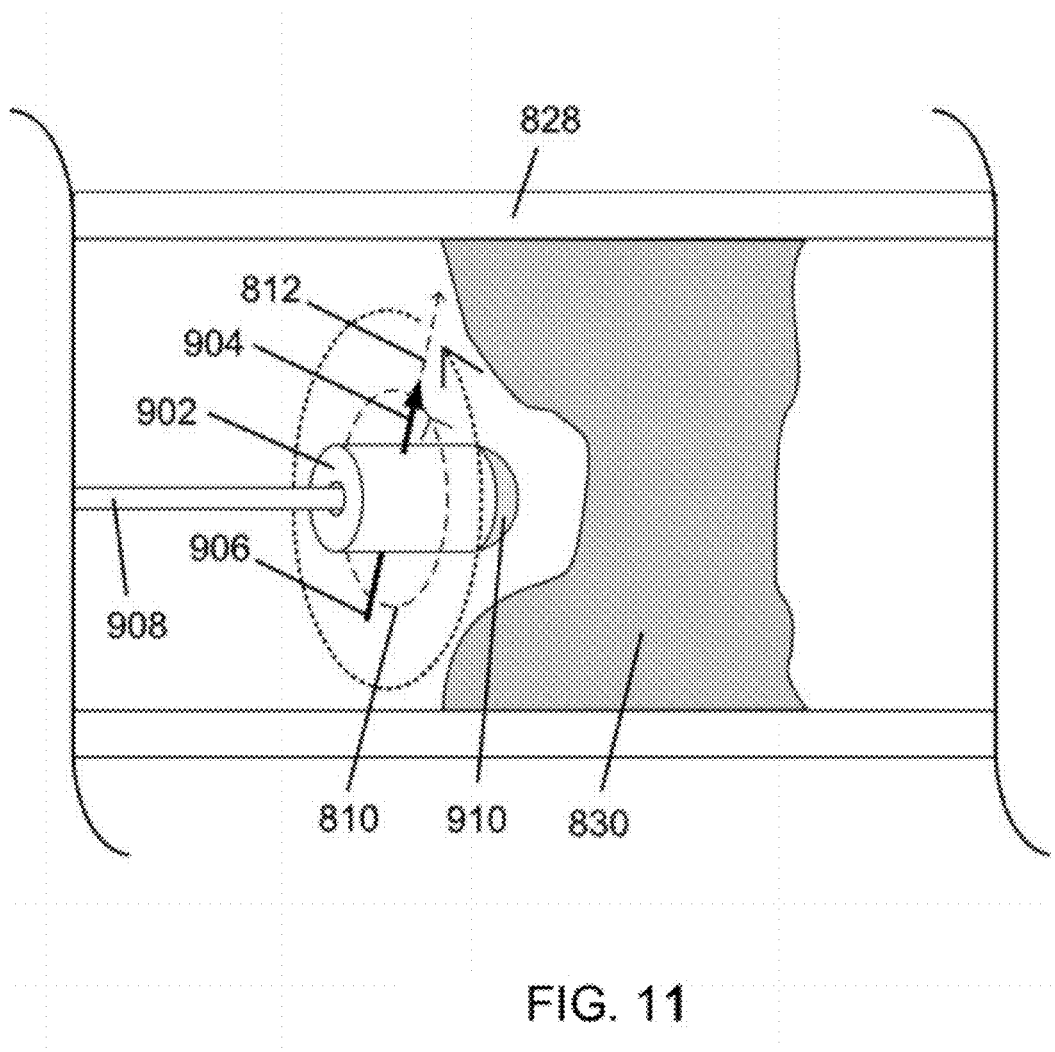
FIG. 11 illustrates the manipulation of a magnet to cross a vessel occlusion, in accordance with an embodiment of the invention.
Figure 12A:
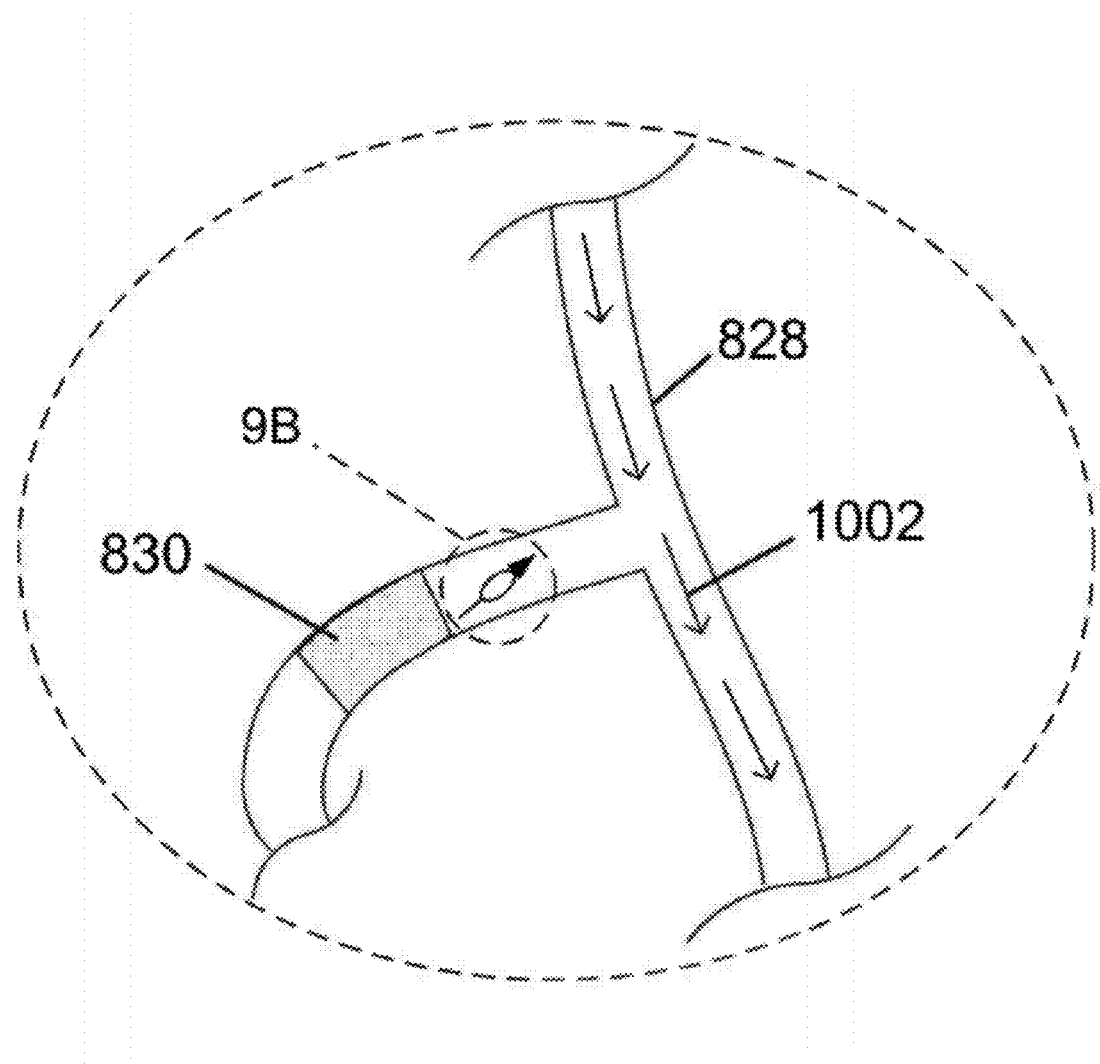
FIGS. 12A and 12B illustrate an example method of use of a magnetomotive stator system and magnetic nanoparticles for the treatment of a vascular occlusion in the brain, in accordance with an embodiment of the invention.
Figure 12B:
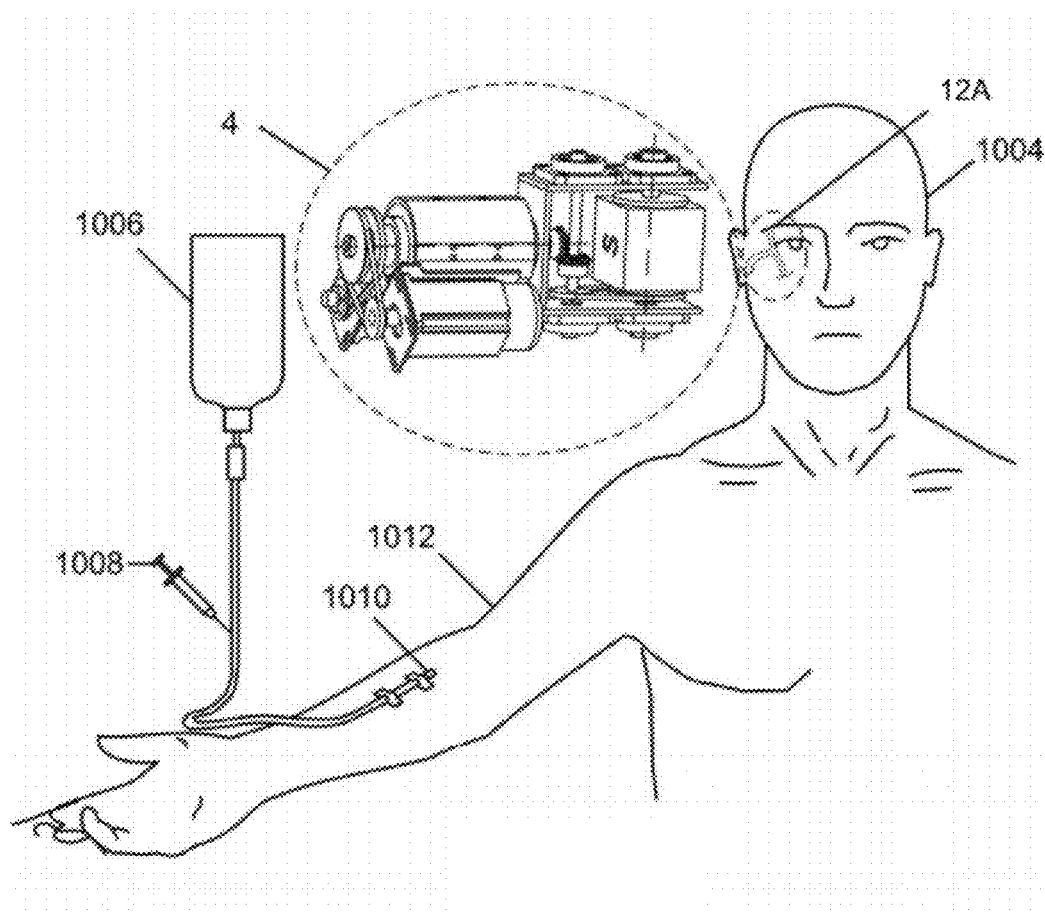

FIG. 11 shows an example use of the magnetomotive stator system to wirelessly manipulate a mechanical thrombectomy device (also referred to as a "magnetic tool" above). In this example, a vessel obstruction 830 inside a blood vessel 828 is unblocked by a rotating magnet 902 which possesses a North magnet pole 904 and a South magnet pole 906 in directions transverse to the axis 908. The magnet 902 follows the external magnetic field vector 812, which is generated wirelessly by the magnetomotive stator system. The external magnetic field vector 812 changes in time in the direction of the magnetic field rotation angle 810. The rotation of the magnet 902 is stabilized by passing a stabilizing rod 908 through a hole in the magnet 902. The magnet 902 is free to rotate about the stabilizing rod 908. An abrasive cap 910 is affixed to the magnet 902 which engages the vessel obstruction 830. This abrasive cap 910 may use a coating or surface treatment that ensures minimal damage to healthy tissue and maximal damage to the vessel obstruction 830.

In accordance with several embodiments, the use of the magnetic gradient, which may be time-varying, and a time-varying magnetic field allows for devices to be constructed which possess a magnet capable of rotating at the distal end. The magnetomotive devices described herein can be made much smaller and cheaper than existing clinical devices used to amplify the effects of pharmaceuticals or to bore through obstructions in the vasculature. Moreover, commercial technologies that use a rotation mechanism within a vessel or chamber require a mechanical or electrical transmission system from the proximal end to the distal end, which can complicate the device, make the device more expensive, and/or increase the overall size. Systems and devices described herein can generate mechanical action wirelessly at the tip without the need for a mechanical or electrical transmission system, thereby allowing the device to be smaller, simpler, and/or cheaper to manufacture.

For example, the magnetic-based system may be used in a clinical setting for the enhancement of the effectiveness of tPA which is injected intravenously. Magnetic particles (e.g., magnetic nanoparticles) can be injected either before or after introduction of the tPA within the vasculature, or can be attached to a thrombolytic agent (e.g., tPA). The magnetic-based system, which is placed or positioned close to the patient (e.g., within two feet, within 1 foot, within 10 inches, within 9 inches, within 8 inches, within 7 inches, within 6 inches, within 4 inches, within 3 inches, within 2 inches, within an inch of the patient) and near a location of a therapeutic target (e.g., an obstruction, a clot), can be activated. In some embodiments, the magnetic-based system would not need to be generating a changing (e.g., rotating) magnetic field at this time in that the gradient would be sufficient to collect particles at the therapeutic target (e.g., an obstruction, a clot). When magnetic-based mixing of fluid within the vasculature is desired, the magnetic field can be made to alternate in time (e.g., by rotating one or more permanent magnets or controlling current through coils of an electromagnet) which, when combined with the magnetic gradient, which may or may not be varying in time, causes the action of the therapeutic agent (e.g., a thrombolytic agent such as tPA) to be enhanced. In accordance with several embodiments, a clot or other fluid obstruction or blockage could be destroyed faster and better as compared to existing approaches. For example, the magnetic nanoparticles can be manipulated to form a vortex (e.g., predictably circulate) in a region of stagnant flow so that the therapeutic agent (e.g., tPA) is better mixed, resulting in a more efficient drug interaction. Creating a vortex can also draw in more of the therapeutic agent near the region of turbulent flow.

Magnetically-Enhanced Drug Diffusion

FIG. 13 illustrates some examples of how to magnetically enable control over the diffusion of a therapeutic agent (e.g., a chemical or adjunct) injected into a moving fluidic system (e.g., circulatory system). In the illustrated model, fluid A is travelling and permeates the fluidic system (illustrated as the white region in FIG. 13A). At a later time, fluid B is injected (illustrated as the shaded region). FIG. 13B illustrates a problem associated with solely injecting fluid B without introducing and manipulating magnetic nanoparticles—fluid B is limited in its ability to penetrate the "leg" or branch to reach a therapeutic target because the velocity of the flow does not travel far into the leg or branch. Existing systems then must rely on diffusion to dilute fluid-A with fluid-B. This can take a very long time.

Figure 13A:
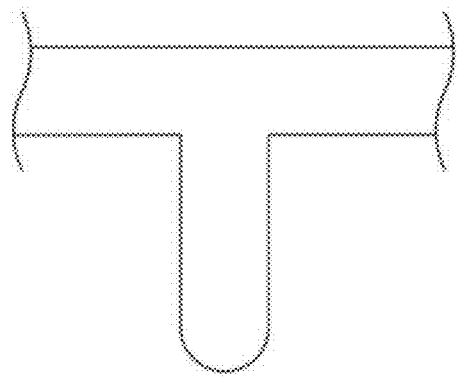
FIGS. 13A-13E illustrate a model for the enhanced diffusion of therapeutic drugs in an area of complete blockage having no fluid flow, in accordance with an embodiment of the invention, where (A) shows a vessel having no drug, (B) shows the addition of a drug to the system (shown in grey), but the inability to mix at the site of the blockage, (C) shows the addition of magnetic nanoparticles to the system that are drawn to the blockage site via a magnet (not shown), (D) shows turbulence created by applying the magnetic field and gradient in a time-dependent fashion and mixing the drug to come closer to contacting the blockage site, and (E) showing completed diffusion of the drug and contact at the blockage site via mixing using the magnetic nanoparticles.
Figure 13B:
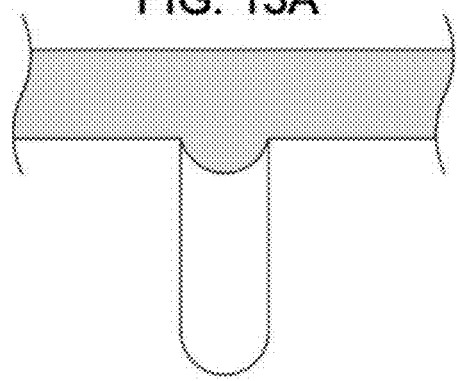
Figure 13C:
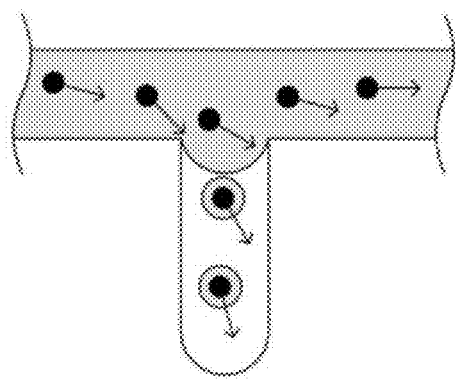
Figure 13D:
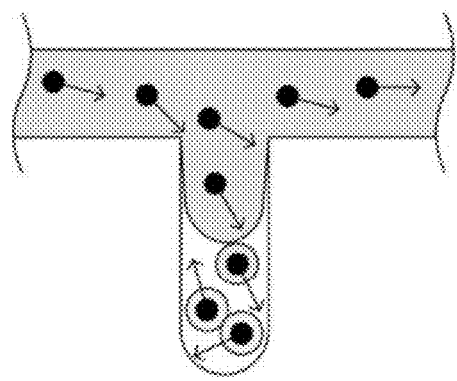
Figure 13E:
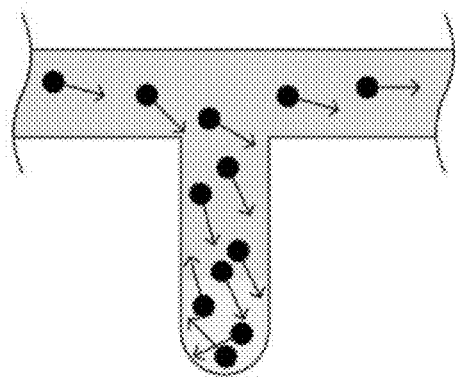

In some embodiments, it has been observed that when magnetic nanoparticles are placed into fluid B, and a magnetic field and gradient are applied (e.g., imposed) to pull some of the nanoparticles out of the bloodstream into the leg or branch, the nanoparticles take a bit (e.g., an amount) of fluid B with them (as shown in FIG. 13C). Time-varying aspects can be changed or varied to amplify the diffusion-facilitating action. For example, the rate of magnetic field rotation, the strength of the magnetic gradient, the orientation of the source field, the size and strength of the magnetic nanoparticle, or any combination of these can be changed to amplify the action. In time, more nanoparticles can collect at the bottom of the leg or branch and begin to set up circulation patterns (e.g., vortexing patterns), which distribute fluid B into fluid A faster than via diffusion alone. The longer the process runs, the more nanoparticles are collected, and the stronger the mixing effect becomes, until fluid A is substantially replaced with fluid B at the region of the therapeutic target.

In the case of clot destruction, the leg or branch represents a blocked (e.g., partially or completely obstructed or occluded) vein or artery. As depicted in FIG. 13, to facilitate contact of a therapeutic agent (e.g., thrombolytic drug) with the therapeutic target (e.g., surface of a blocked vessel), the force of diffusion is principally involved if the obstruction is sufficiently far from the main flow. Therefore, therapeutic agents (e.g., thrombolytic drugs, chemicals, adjuncts, pharmaceutical compositions) effective in substantially clearing a fluid blockage from a circulatory system are limited in their effectiveness; relying on diffusion alone in vivo could result in negative clinical outcomes. Because therapeutic agents (e.g., thrombolytic drugs, chemicals, adjuncts, pharmaceutical compositions) effective in substantially clearing fluid blockages from a circulatory system may have a relatively short half-life, the use of the magnetomotive stator systems, in combination with the magnetic nanoparticles described herein, can speed the process of clearing fluid blockages by the therapeutic agents. If the objective is to deliver a therapeutic concentration of fluid B at the end of the leg or branch which is a fraction of the concentration in the main flow, use of the systems and methods described herein can result in the same therapeutic concentration of fluid B for a much smaller dose of fluid B initially injected (See FIG. 38). Thus, some embodiments provide enhanced therapeutic advantages by allowing the use of a smaller dose of a therapeutic agent than would normally be used without the introduction of magnetic nanoparticles controlled by the magnetic-based control systems described herein, thereby reducing the occurrence of bleeding or even death due to excessive doses. For example, the dose of therapeutic agent used on conjunction with the magnetic nanoparticles and magnetic-based control systems described herein can be less than or equal to about 50%, about 45%, about 40%, about 35%, about 30%, about 25%, about 20%, about 15%, about 10%, about 5%, of the standard prescribed dose.

For example, systems and methods described herein can be used in a collection mode to manipulate a collection of magnetic nanoparticles to translate a stream of the magnetic nanoparticles into an occluded branch. As a result, a fluidic current can originate from the parent vessel flow's turbulent region near bifurcation. This flow can draw in a therapeutic agent (e.g., a chemical adjunct) within the bloodstream towards the terminal end of the occluded branch better than by diffusion alone.

As another example, magnetic-based systems and control methods described herein can be used in a vortexing mode to manipulate the magnetic nanoparticles to create a vortex in a region of stagnant flow so that a therapeutic agent (e.g., chemical adjunct) is better mixed within the bloodstream, resulting in a more efficient chemical reaction with a fluid obstruction (e.g., due to continuous refreshing of the portions or molecules of the therapeutic agent that is in contact with the fluid obstruction). In some embodiments, clot dissolution time can be increased by a factor of three or more when the vortexing mode is used. Such manipulation can be achieved by oscillating a magnetic field in different directions at a particular frequency. For example, the frequency can be greater than or equal to about 0.25 Hz and/or less than about 3 Hz, including but not limited to between about 0.25 Hz and about 1 Hz, between about 0.5 Hz and about 2 Hz, between about 1 Hz and about 3 Hz, between about 0.75 Hz and about 2.5 Hz, overlapping ranges thereof, less than 3 Hz, less than 2 Hz, less than 1 Hz. The vortexing mode of control can enable more of the therapeutic agent (e.g., chemical adjunct) to be drawn in near the region of turbulent flow.

In accordance with several embodiments, alternating between the collection and vortexing modes can result in an improved ability to draw the therapeutic agent (e.g., chemical adjunct) near a region of turbulent flow and translate that therapeutic agent in a better way into an occluded branch. Alternating between the collection mode and the vortexing mode can include altering the magnetic gradient and/or the time-varying magnetic field to cause the magnetic nanoparticles to behave differently. For example, in the collection mode, the magnetic gradient can be increased and the time-varying magnetic field can be decreased such that the magnetic nanoparticles experience a net force that results in the magnetic nanoparticles substantially accumulating at a desired location. As another example, in the vortexing mode, the magnetic gradient and/or the time-varying magnetic field can be adjusted such that the magnetic nanoparticles experience a time-varying net force that results in circulating motion and/or angular velocity within a desired region. Thus, by changing the magnetic field properties (e.g. the magnetic gradient, the magnetic field strength, orientation of the magnetic field, direction of the magnetic field, etc.) as a function of time, the magnetic-based systems and control methods can be used in and switched between collection mode, vortexing mode, navigation mode, or some combination of modes.

In the case of the magnetic tool, the system is capable of advantageously grinding away large volumes of thrombus or other blockage material, such as atherosclerotic plaque material, quickly and very precisely. It has been observed that, in accordance with some embodiments, a 2 French hole (⅔ mm) was cut through a mock atherosclerotic clot using an embodiment of the wireless magnetomotive stator system. With respect to the use of magnetic nanoparticles, the system allows for more precise control of magnetic nanoparticles to create a relatively "gentle" scouring action that allows the leaf valves in the veins to remain intact and undamaged. With respect to the magnetic tool, this action can be used in combination with thrombolytic drugs to remove clot material in an occluded artery or vein. When used with a thrombolytic drug to treat a blood clot, the thrombolytic drug could be helpful when mechanical action is intended to be minimized. Using magnetic nanoparticles, the material removed from the blocked vein can be captured with a small magnet on a guide wire. Depending on the mode of operation, the removed material has been observed to be small (less than 1 mm size clot particles), or ball mixtures of clot material, drug and magnetic nanoparticles. Both the magnetic nanoparticle collection and magnetic tool objects are capable of being visualized with standard imaging technologies allowing for computer-reconstructed path planning.

Furthermore, imaging technologies can be incorporated into (e.g., communicatively coupled to) the magnetic control system such that an operator can have real-time feedback of the position of the magnetic nanoparticles, thereby allowing for dynamic control and navigation. The real-time feedback provided by imaging technologies can increase the effectiveness of the process, for example, by providing adjustment of parameters of the rotating magnetic field (e.g., orientation, position, rotation frequency) and/or the magnetic gradient, by introducing more nanoparticles and/or by introducing increased quantities of therapeutic agents.

The real-time feedback can include information related to the concentration of therapeutic agent in a particular location (e.g., adjacent a fluid obstruction of an obstructed blood vessel), information related to the concentration of magnetic nanoparticles or nanorods in a particular location (e.g., adjacent a fluid obstruction of an obstructed blood vessel), which may be correlated to or indicative of the concentration of therapeutic agent at the location, images of the fluid obstruction, information related to fluid flow through an obstructed blood vessel, and or other information. The information received through the imaging technologies can be used to determine when to switch between the collection and vortexing modes, which can be performed manually by an operator or automatically by a computer controller. For example, if it is determined that a concentration of therapeutic agent or magnetic nanoparticles or nanoparticle rods is low at a location adjacent a therapeutic target, the magnetic control system can be switched to or remain in the collection mode to increase the concentration levels. If it is determined that a concentration of therapeutic agent or magnetic nanoparticles or nanoparticle rods is sufficient, the magnetic control system can be switched to or remain in the vortexing mode.

Figure 14:
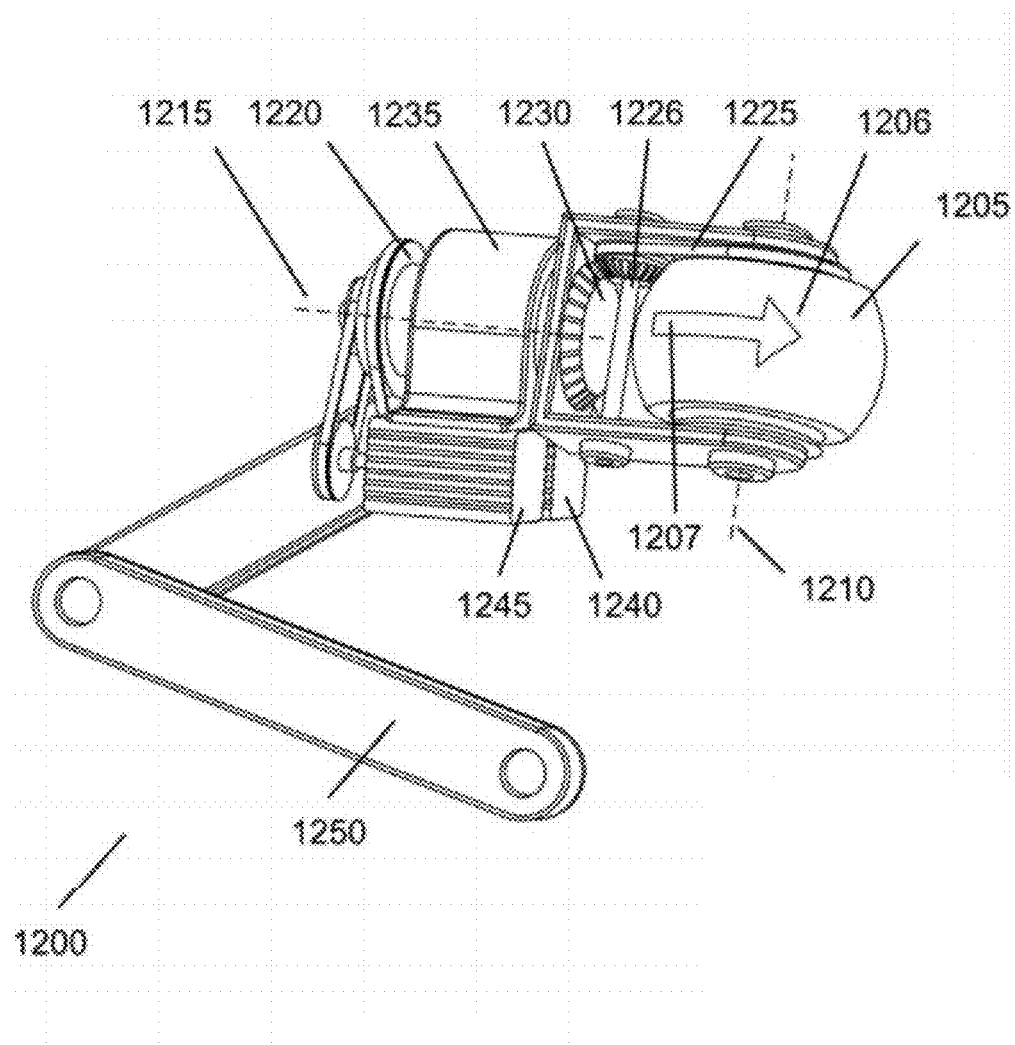
FIG. 14 illustrates an embodiment of the magnetomotive stator system.

FIG. 14 illustrates an embodiment of a magnetic field generator. In the depicted figure, the generator 1200 comprises a permanent magnet source 1205 with North 1206 and South 1207 poles, mounted so that two separate rotations about axis 1210 and about axis 1215, respectively, are enabled. For spin about axis 1210, magnet source 1205 is rotated by pulley belt 1225, which is driven by geared shaft 1226, which in turn is driven by driving gear 1230. Gear 1230 is mounted on thrust bearing 1235 and driven by motor 1240 mounted on rotor system 1225, 1226, 1230, 1231 that enables rotation about the spin axis 1210 using a motor 1245. A separate drive system enables rotation about second axis 1215 using components 1220, thrust bearing 1235, and motor 1240. The generator is positioned with the jointed arm 1250.

In some embodiments, the jointed arm 1250 is a robotic arm, configured to move (e.g., translate the generator 1200 in one, two, or three dimensions and/or rotate the generator along one, two, or three axes. The jointed arm 1250 can include one or more joints to facilitate positioning and translation of the generator 1200. In some embodiments, the jointed arm 1250 allows for unrestricted free motion that is not dependent on movement along or about fixed axes. The jointed arm 1250 can be configured to move automatically and/or through operator remote control. The generator 1200 advantageously provides simplicity, smaller size, and lower cost in accordance with several embodiments.

Figure 15:
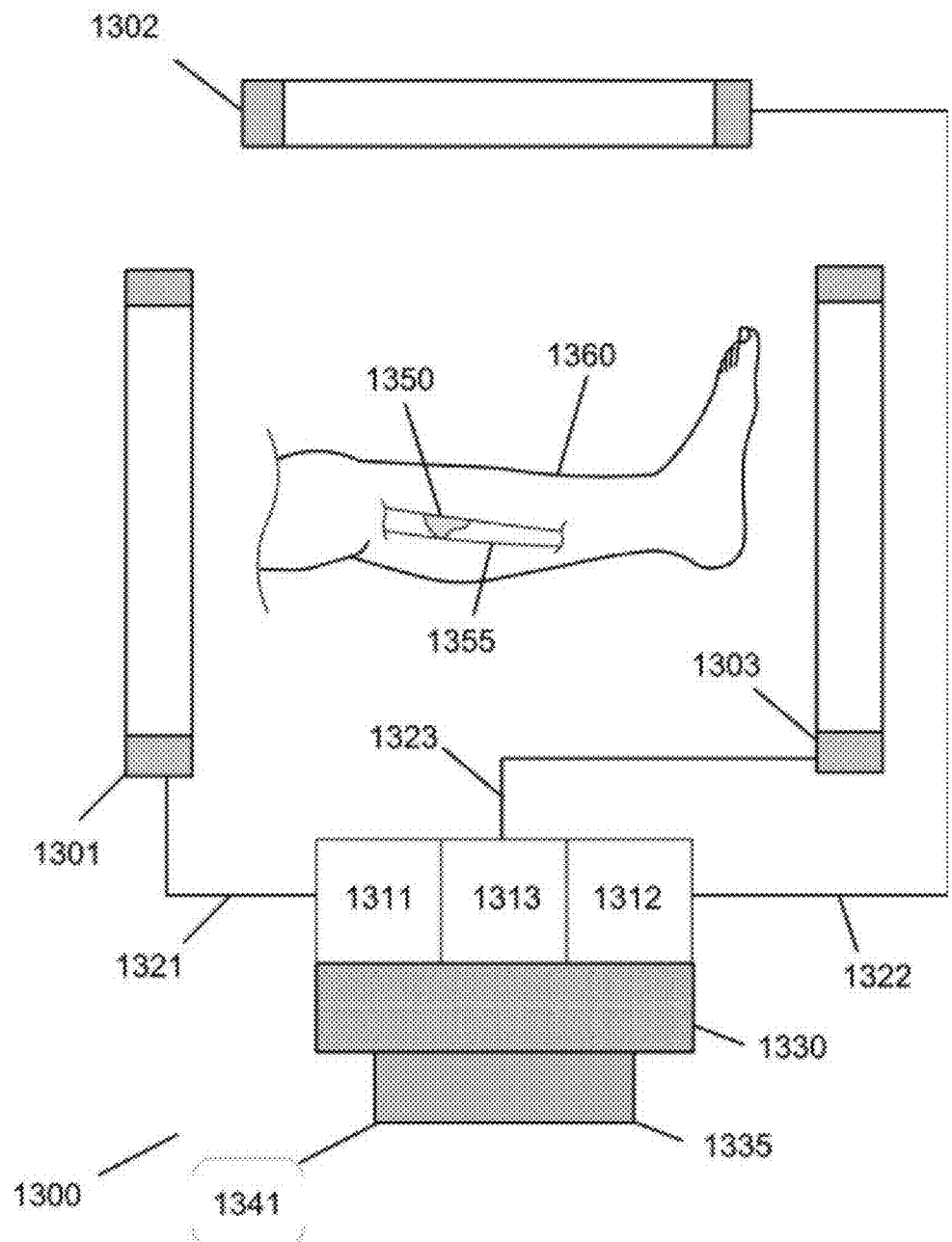
FIG. 15 illustrates an embodiment of the magnetomotive stator system.

In some embodiments, the generator 1200 has additional features where the simplicity of the design of generator 1200 is not desired. The generator 1300 depicted in FIG. 15 displays an example of such an embodiment. FIG. 15 is a schematic drawing of an embodiment of a field and gradient generating device. FIG. 15 is a block diagram of a magnetic field generator 1300. Three coils, 1301, 1302, and 1303, are fed currents from drivers 1311, 1312, and 1313, through connections 1321, 1322, and 1323, respectively. Drivers 1311, 1312, and 1313 are current sources controlled separately by a distributing circuit 1330, which receives information from a computing device 1335. Current sources, 1311, 1312, 1313, can be capable of generating a sine wave current sufficient to provide the peak magnetic field desired. In some embodiments, the peak magnetic field is less than or equal to about 0.3 Tesla. If different magnetic field characteristics are desired in individual cases, the currents may have more complex temporal variations than sine waves. As determined by computing device 1335, in response to operator input 1341, the distribution and types of currents and their sequences to the coils can be calculated by the computing device 1335. The specific operational instructions from programs stored in memory communicatively coupled to the computer 1335 are based on knowledge of the particular operation, with specific instructions thereby provided for operating according to the procedure input by the operator (e.g., physician). The generator 1300 advantageously provides added flexibility in the type of fields generated from the more complex magnetic field sources and the computer input, and the added refinement to the new procedures.

Figure 16A:
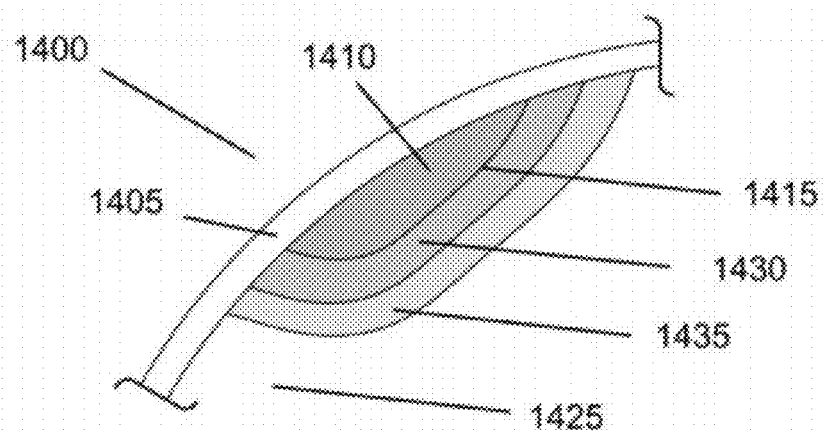
FIG. 16A is a cross sectional drawing displaying a representative targeted region of a blocked lumen with no flow, under conventional treatment.
Figure 16B:
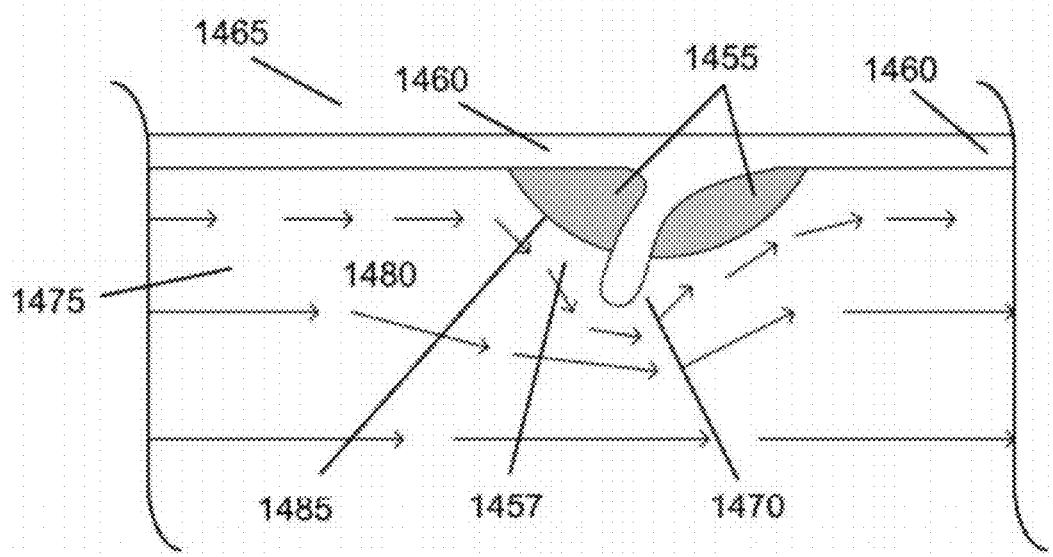
FIG. 16B is a cross sectional drawing of a targeted region having blood flow, but with ineffective drug clearance using standard drug delivery.

Two major classes of blockage in the medical cases to be treated by methods described herein are partial and total. Partial blockage yields, in general, low blood flow, while total blockage will result in no blood flow. In both cases, the effectiveness of a drug delivered to remove the clot by conventional means will generally be difficult and inefficient. The delivery of the drug to the surface of a clot is in principle difficult and inefficient in spite of special methods to stir the drug-blood mixture near a clot. Major limits to methods of removing the blockages include the difficulty of effective drug action on an occlusion, the incompleteness of removal of dislodged material, damage to vessels and adverse effects of downstream components of the removed material. FIGS. 16A and 16B exhibit the underlying physical reasons for the difficulty and inefficiency of conventional treatments of a blood clot, and for which this disclosure provides major improvement.

FIG. 16A is a cross sectional view of a typical accumulation of occluding material in a bend of a section of a blood vessel 1400 having no flow, illustrating a common difficulty in using a drug (e.g., thrombolytic drug) for dissolving the occluding material. Adjacent a vessel wall 1405 is a target region of deposited occluding material 1410, the "clot," with internal boundary edge 1415. In the depicted example, the physician or other medical professional has introduced a drug 1425 in the vicinity of the clot. FIG. 16A exhibits the typical situation of a stagnant action layer 1430 of partially interacting material and a layer 1435 of more concentrated but less effective drug. Layers 1430 and 1435 separate the clot from the more concentrated thrombolytic drug 1425 that had been injected into the vessel 1400 in the general region of the target region. Motion and distribution of the drug can arise from thermal agitation and slow dispersion as a means of refreshing contact between the clot and the injected drug, which makes the action extremely slow and inefficient. Some practitioners have introduced metal stirrers, venturi flow-based jets, and sound-based agitation technologies to increase efficiency, but the difficulties and limitations of those methods have been documented.

FIG. 16B is a cross section view of a target occlusion 1455 formed against a wall 1460 of a vessel 1465 having a stiffened valve leaflet 1470, with low blood flow in a region 1480 and with relatively low fluid (mixed blood and drug) flow at the clot surface 1457. As a result, there is relatively little interaction between the clot and a drug 1475 injected upstream into the region 1480. One approach could be to increase the quantity of drug 1475 injected upstream, but this may be undesirable due to potential adverse effects caused by increased drug dose and/or cost. Other typical approaches involve closing off the vessel and slowly injecting a thrombolytic agent, with slow, inefficient dissolving of the clot, and the injection of large quantities of thrombolytic drug, thus exhibiting approximately the same difficulties of the case with a blocked vessel (e.g., vein). Some treatments provide artificial mechanical, venturi flow-based, and sound-based agitation in region 1480 in attempts to enhance the efficiency of interaction at the clot surface 1485. Catheters with jets may spray thrombolytic drugs in attempts to get more efficient dissolution of the clot. Removal of the occluding material is sometimes performed by insertion of mechanical devices, with considerable difficulty and with danger to the valve. All of these methods may be helpful in some cases, but are generally of limited effectiveness.

Figure 17A:
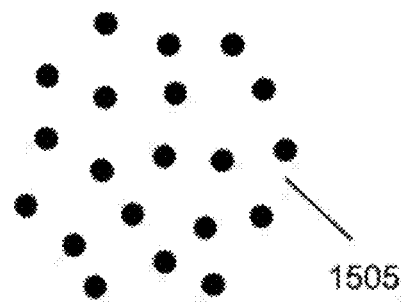
FIGS. 17A-17C illustrate arranged structuring of magnetic nanoparticles to create rods as used in procedures according to some embodiments, where (A) shows unorganized nanoparticles in zero field, (B) shows a small field applied to the nanoparticles and organization into "rods," and (C) shows a larger field applied to the nanoparticles.
Figure 17B:
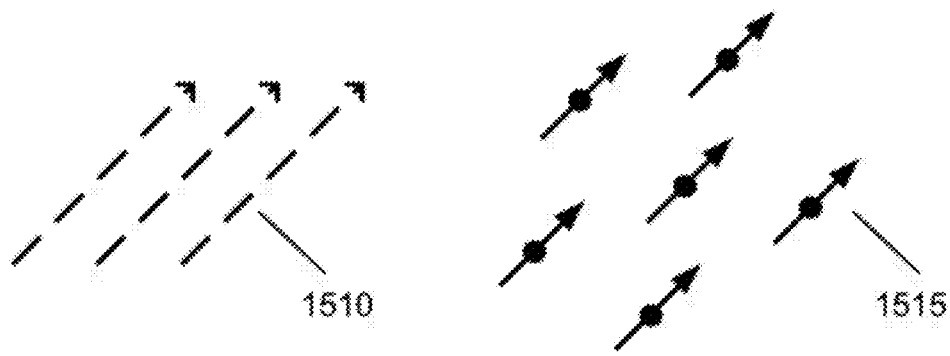
Figure 17C:
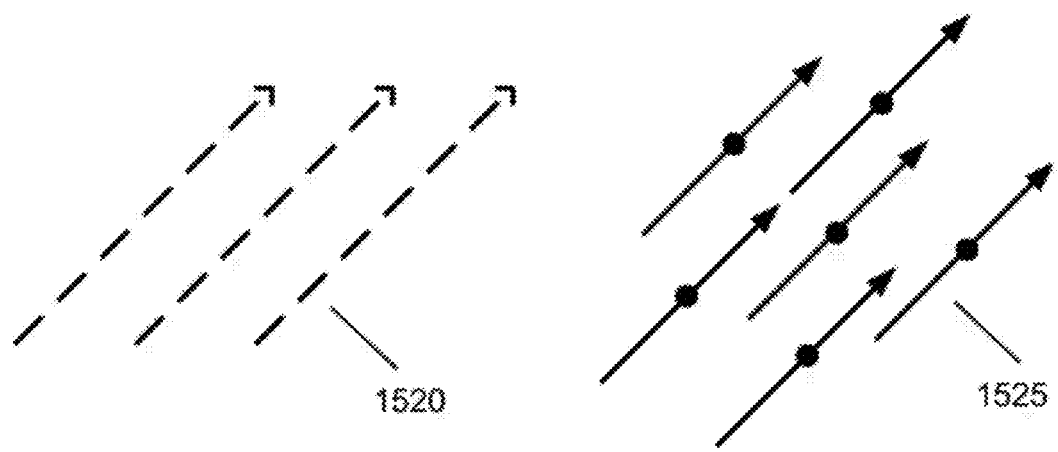

FIGS. 17A through 17C exhibit the underlying process, according to some embodiments, in the development of nanoparticle rods from chains of magnetic nanoparticles. FIGS. 17A-17C show a cross section of the sequence of structuring of coated or uncoated magnetic nanoparticles with increasing magnetic field. Increase of the field during a rising part of the cycle may cause more and more nanoparticles to align into longer nanoparticle rods.

These are shown with zero field in FIG. 17A as nanoparticles in a random disposition of particles 1505, arrayed so as to be roughly evenly distributed in space, and having a certain statistical fluctuation in position. In FIG. 17B, when a small external magnetic field 1510 is applied to the same group of nanoparticles, they are formed into a loose array 1515 of short, oriented magnetic "rods." At a certain larger field 1520, depending on nanoparticle size and coating, shown in FIG. 17C, the same nanoparticles aligned as magnetic rods 1525 have become longer. In this figure, it is depicted that the rods are uniform in size although that is not strictly the case, nor is it necessary. This magnetic process can be viewed in two ways: a) the field increase from FIG. 17A to FIG. 17B being that in a single (slow) cycle of magnetic field alternation, or b) the increase over a number of cycles as the peak-to-peak magnitude of the field generated is increased. Depending on the absolute scale and oscillating frequency, the actions are not reversed during a given cycle of oscillation. In general, the method applies magnetic fields of greater than or equal to about 0.01 Tesla and/or less than or equal to about 1 Tesla, including but not limited to from about 0.01 Tesla to about 0.1 Tesla, from about 0.05 Tesla to about 0.5 Tesla, from about 0.1 Tesla to about 0.6 Tesla, from about 0.3 Tesla to about 0.9 Tesla, from about 0.5 Tesla to about 1 Tesla, overlapping ranges thereof, less than 1 Tesla, less than 0.5 Tesla, less than 0.25 Tesla, less than 0.1 Tesla. Gradient strength can be greater than or equal to 0.01 Tesla/m and/or less than or equal to 10 Tesla/m, including but not limited to from about 0.01 Tesla/m to about 1 Tesla/m, from about 0.01 Tesla/m to about 3 Tesla/m, from about 0.05 Tesla/m to about 5 Tesla/m, from about 1 Tesla/m to about 4 Tesla/m, overlapping ranges thereof, less than 5 Tesla/m, less than 3 Tesla/m, less than 2 Tesla/m, less than 1 Tesla/m. In general, rods can have a length that is greater than or equal to about 0.05 mm and/or less than or equal to about 3 mm in length, including but not limited to from about 0.05 mm to about 2 mm, from about 0.1 mm to about 2 mm, from about 0.2 mm to about 1.5 mm, from about 0.2 mm to about 1 mm, from about 0.3 mm to about 0.9 mm, from about 0.4 mm to about 0.8 mm, overlapping ranges thereof, less than 3 mm, less than 2 mm, less than 1.5 mm, less than 1 mm.

Figure 18:
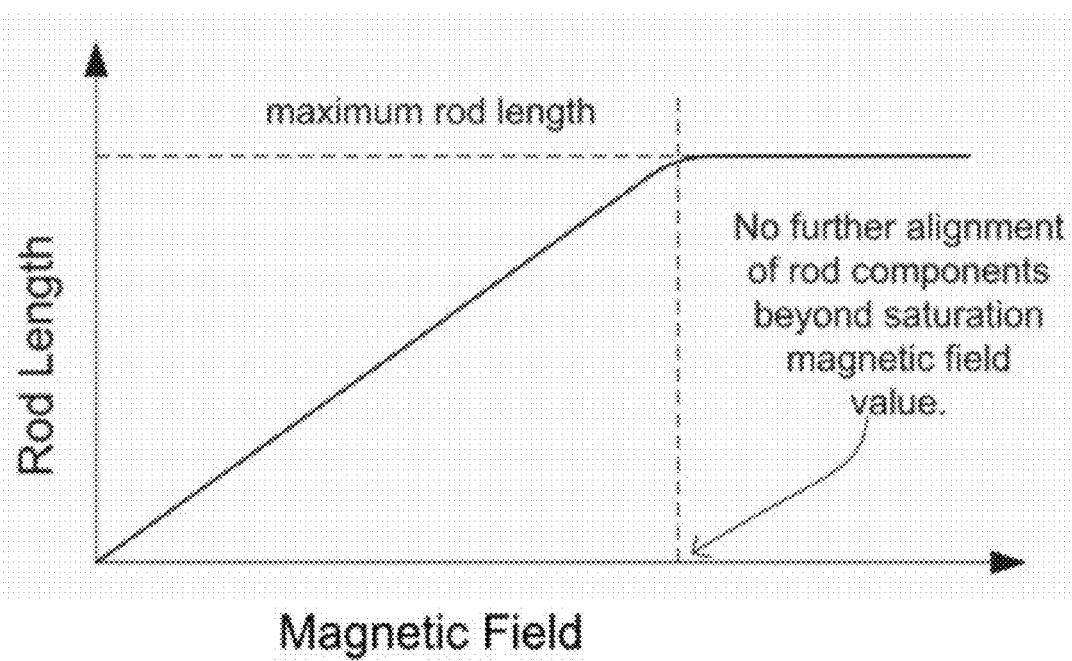
FIG. 18 is a plot of nanoparticle agglomerate rod length as a function of the applied magnetic field, showing a limiting length, in accordance with an embodiment of the invention.

At a certain rotating magnetic field strength and field rotation frequency, depending on nanoparticle size and coating, the rods will reach a saturation field and achieve a maximum length, developing as depicted in the graph of FIG. 18. The rod growth is not necessarily exact, and the curve illustrates a general nature of the growth. Fully developed rods may contain a number of nanoparticles, as many as 10 or many more, depending on their size, and the magnitude of the rotating magnetic field. The rods are not stiff, depending on the magnetic field and gradient, and on the amount of magnetite in each nanoparticle as well as the nanoparticle size. Other materials may be attached to nanoparticles for chemical, magnetic, and imaging reasons. That chemical can be a thrombolytic drug. The thrombolytic drug can also be injected independently.

Figure 19:
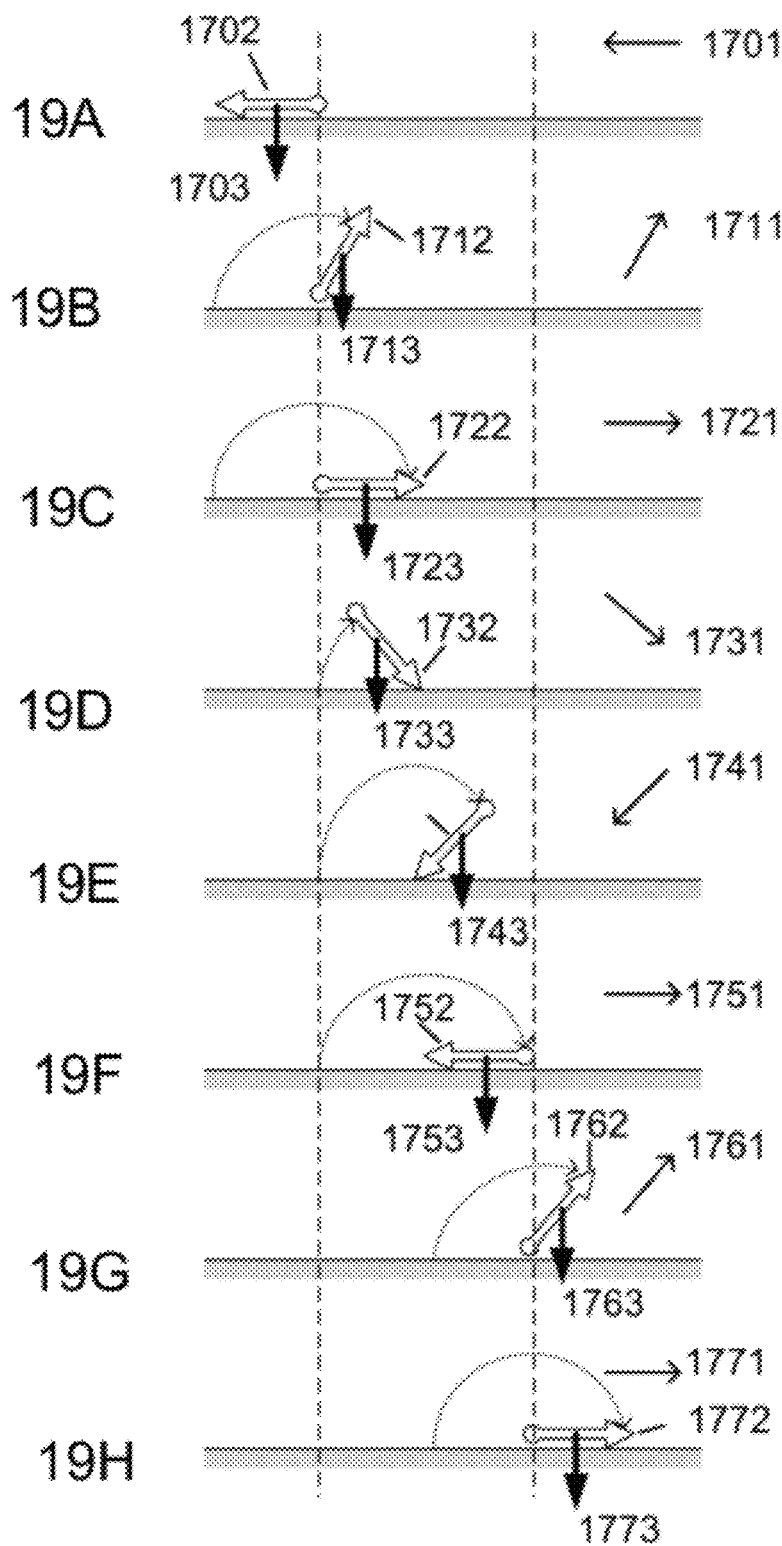
FIG. 19 illustrates a sequence of end over end motions leading to translation of magnetic rods formed from a plurality of magnetic nanoparticles, in accordance with an embodiment of the invention.

FIG. 19 illustrates geometric features of the end-over-end walk of a single rotating rod acting from application of a rotating magnetic field emanating from a fixed source in space. It displays a sequence of 8 positions of a single rotating rod as it rotates and walks, so as to exhibit the directions of field and pulling force of the gradient. It is to be understood that the effective magnetic moments of individual nanoparticles are substantially continually aligned with the local magnetic field, so that they maintain the interactions to retain the rod and its magnetic moment, while the field and rod are rotating, that is, maintaining alignment of the rod with the field.

Without being bound by a particular theory, and as will be discussed in the following section in equations [1] and [2], the field B establishes a torque, but it does not exert a pulling force on the rod moment, while the gradient G exerts a pulling force but no turning torque on the moment. Therefore, a rotating magnet source will have a pulling gradient towards it, shown as the downward arrows in stages shown in FIG. 19. Smaller magnetic nanoparticles (generally below 200 nm, below about 170 nm, below about 150 nm in diameter) act primarily as magnetically permeable materials, which substantially align with the local field without individually rotating in space. In FIG. 19, trigonometric labeling illustrates the geometrical (angular) aspects of changing components of the force and torques on the nanoparticles as related to the walk of the rod towards the right in response to the rotating field. In other words, the rods act approximately as fixed magnetic rods. In FIG. 19, the field direction in each of the 8 positions, is shown by arrows 1701, 1711, 1721, etc. as the field rotates clockwise. The rod magnetic moments 1702, 1712, 1722, etc. follow that direction. In the stages shown in FIG. 19, however, the arrows 1703, 1713, 1723, etc. point downward towards the center of the rotating field source, representing the magnetic gradient according to equation [2] below. On the scale of the rod lengths, about 2 mm, the movement to the right is small relative to the distance to the source magnet.

Figure 20A:
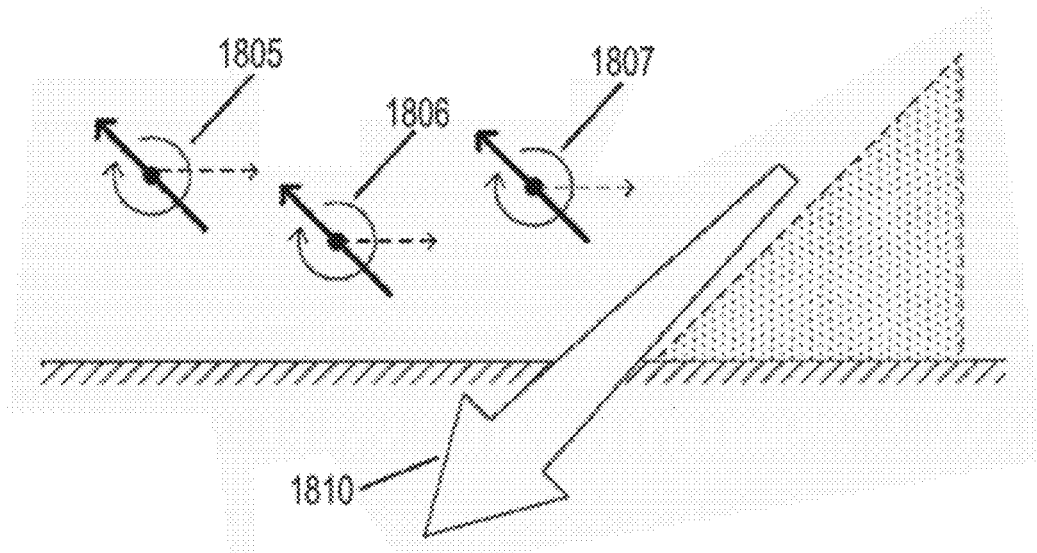
FIGS. 20A and 20B illustrate a characteristic saturation of nanoparticles with increased density as a result of rotating motion leading to a buildup of magnetic nanoparticles.
Figure 20B:
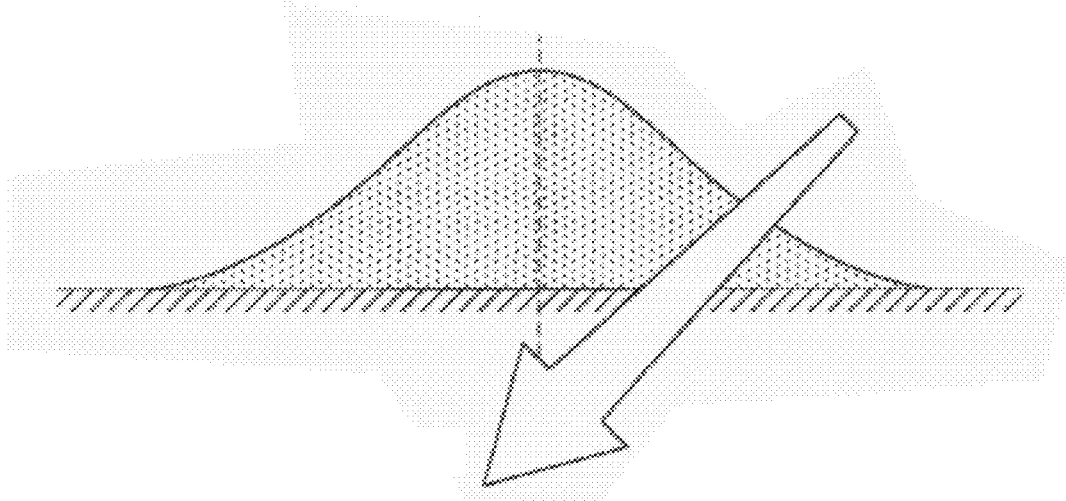

FIGS. 20A and 20B illustrate the development of a limit to the concentration of magnetic rods when the source magnetic field is rotating about a fixed position of the source magnet. The gradient, unlike the field, may pull towards the magnetic center of the source. The field B itself creates a torque $\tau$ of alignment on a magnetic dipole moment $\mu$:

$$\tau = \mu B \sin \phi, \qquad [1]$$

where $\phi$ is the angle between the direction of the magnetic moment $\mu$ and the magnetic field B. A uniform field without gradient will not create a net force on the moment $\mu$. However, a gradient G will create a force F on magnetic moment $\mu$ according to:

$$F = \mu G \cos \phi, \qquad [2]$$

where φ is the angle between the direction of the moment μ and of the gradient G.

FIG. 20A shows the nature of the spatial "resolution" of the system in an open location for the rods. For a fixed location of the rotating magnet source, the pull towards it from the gradient will change direction as the rods 1805, 1806 and 1807 walk to the right. They will have increased their distance from the source, resulting in a loss of strength of the field. In FIG. 20A, as the rotating external field source will have remained at the left shown by arrow 1810, the rod locations have moved to the right of the fixed rotating magnet (below and off screen in FIG. 20A). At the stage shown here, the arrows depicting the three rods 1805, 1806, and 1807 have moved far to the right from the center of the rotating source magnet system. Relative to their size and their distance to the magnet source, this distance to the right has increased so that the field source and gradient are at an angle and are reduced in magnitude. The gradient, in the direction shown by large arrow 1810, pulls on the nanoparticles and rods, which are driven by the traction provided according to the force of equation [2] at their locations. The gradient G can fall off with distance from the source, typically by a factor between the inverse cube and inverse fourth power of distance, while the field B is falling off with distance from the source roughly as the inverse cube of distance from the source center. In this walking, the force caused by the magnetic gradient is reducing which is used to pull them down onto a walking surface. As a result, they can ultimately lose traction. For a fixed location of the magnet source, the distribution of particles begins to approximate a Gaussian distribution. This distribution of particles can be used to describe the spatial resolution of the system.

The resulting motion of the magnetic nanoparticles in the presence of the gradient G can be more easily described if the gradient G is represented as a vector having a component pointing perpendicular to the direction of walking motion (e.g. down in FIG. 20) and a component pointing parallel to the direction of walking motion (e.g. left in FIG. 20). Once the magnetic nanoparticles travel a sufficient distance along a surface such that the perpendicular component of the magnetic gradient G no longer provides sufficient force to maintain traction against the surface, the magnetic nanoparticles can lose traction and change direction. In some embodiments, the change in direction occurs due to the parallel component of the gradient G, which acts to provide a force on the magnetic nanoparticles opposite the walking direction and towards the magnetic source. As illustrated in FIG. 20A, the gradient 1810 would cause a force to the left on the magnetic nanoparticles which would result in motion to the left because the magnetic nanoparticles no longer have sufficient traction against the surface to walk to the right. In some embodiments, the change in direction occurs when the magnetic nanoparticles no longer have sufficient traction against the surface to walk along said surface as illustrated in FIG. 19, and a fluid flow in the region causes the magnetic nanoparticles to move in an opposite direction. In some embodiments, the change in direction is caused by both the magnetic gradient and the flow in the region. Once the nanoparticles have traveled a sufficient distance in the opposite direction, and if the magnetic gradient G is of a sufficient magnitude and direction, then the magnetic nanoparticles can again gain traction against the surface and walk along the surface in the original direction (e.g. to the right in FIG. 20A). Repeating this sequence can cause the magnetic nanoparticles to move in a circulating, or vortexing, motion.

FIG. 20B illustrates the distribution of particles that can occur when the angle of the gradient is changed from left to right, as a result of the mechanism described in FIG. 20A. This graph is for a fixed location of the magnet source, and is useful in describing the "resolution" of the walking rod system. In practice, the source can be moved if desired for a long occlusion, depending on the medical strategy for treating it.

A consequence of the action described in FIG. 20A is that, for a fixed location of the rotating magnet source, the reduction in force with distance as the rods walk can result in a distribution of rod activity approximately as shown in FIG. 20B where the arrow 1810 simply points to a region of maximum density at closest location to a magnet, and represents the position dependence of the rod walking, which is of maximum strength when the rods are closest to the magnetic source.

The magnetic mechanics of a single rotating rod provide the "soft brush" quantities according to the following calculations. It is to be understood that these conditions apply directly for rod bundles that have relatively sparsely attached clot material. Discussed below is a useful mode of operating rods in a rotating field in which the clot material is allowed to become bundled with the rods, leading to soft clumps that are stable and magnetically removable. Such a mode may not follow the calculations of this section. Nevertheless, the calculations of this section show the underlying behavior of the rotating scouring rods when lightly loaded, and a mode that may be used in cases of small occlusion material, or cases where the delicacy of the procedure or size of vein or artery may not allow clumps of material to be endured. Such cases may arise in some occlusions in the brain.

Figure 21A:
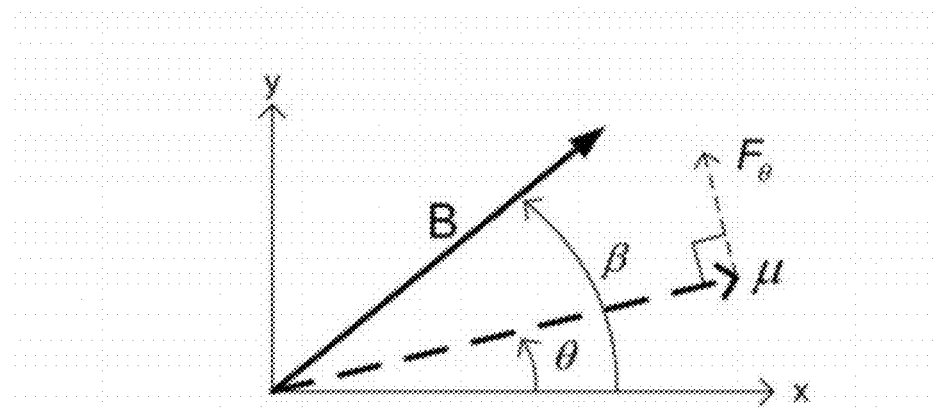
FIGS. 21A and 21B illustrate a derivation of the physics of elements and fields leading to magnetic torque on a nanoparticle rod, in accordance with an embodiment of the invention.

Here, for simplicity, the rods are treated as rigid. FIG. 21A is a diagram exhibiting trigonometric detail of the creation of rotational force and energy on the rotating rods that in turn creates turbulence to enhance drug mixing and interaction with the surface of the clot. The elements of the action of the magnetic rotating field B are shown at a given moment on a single rod of magnetic moment μ in a plane defined by directions of the rod magnetic moment, and the direction of the field B at an instant when B is directed at an angle β from the x-axis. At this instant the (constant) moment μ is directed at an angle θ from the x-axis. Therefore, at this instant the magnitude of the torque τ generated on the moment μ by the external source magnet is given by:

$$\tau = \mu B \sin(\beta - \theta), \quad [3]$$

Figure 21B:
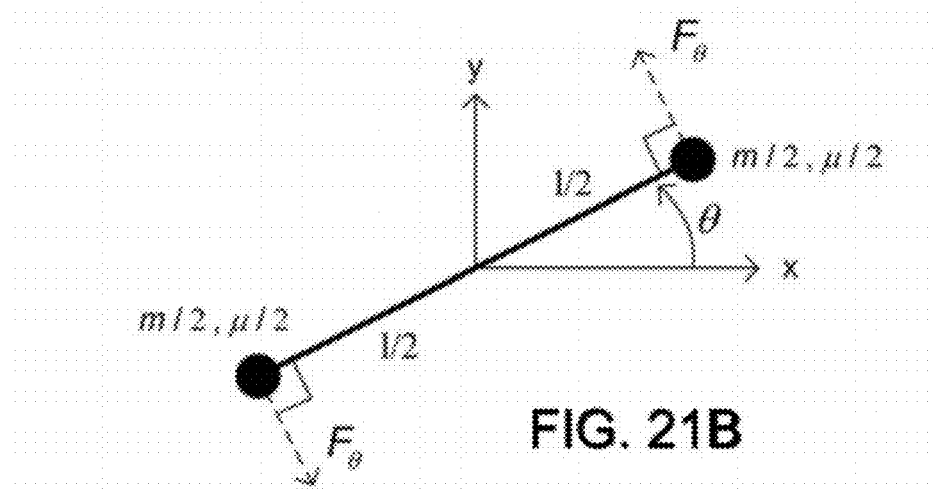

FIG. 21B shows, in coordinates centered at the center of a symmetrical rod, the angular force $F(\theta)$ exerted on the rod, which is assumed to be symmetrical. This assumption is practical when the rod size is small compared with the distance to the magnet source. The resulting force:

$$F_\theta = 2\mu(B/L)\sin(\beta - \theta) \quad [4]$$

is generated by the field B at the ends of a rod of length L.

A drag force might be approximated from standard mechanics with angular velocity dependence $(d\theta/dt)^2$, that is:

$$F_{drag} = -C(d\theta/dt)^2 \quad [5]$$

where C is a proportional constant. Under that assumption, the final equation of motion for a symmetric rod is:

$$(mL/4)(d^2\theta/dt^2) = 2\mu B/L[\sin(\beta - \theta)] - C(d\theta/dt)^2 \quad [6]$$

Further, defining an angle $\alpha = \beta - \theta$ and letting $\beta = \omega t$, with $\omega$ an angular rotational frequency of the magnetic field B, then $\alpha = \beta - \theta$ and therefore, $d^2\alpha/dt^2 = -d^2\theta/dt^2$.
Equation [3] becomes:

$$(mL/4)(d^2\theta/dt^2) = 2\mu B/L \sin \alpha - C(\omega - d\alpha/dt)^2 \quad [7]$$

For a constant lead angle α, this simplifies to:

$$\sin \alpha = CL\omega^2/2\mu B \quad [8]$$

A maximum frequency $\omega_o$ that preserves a constant lead angle $\alpha$ is $$\omega_o^2 = 2\mu B/CL, \quad [9]$$

where $\alpha = \pi/2$, that is, 90 degrees.

Figure 21C:
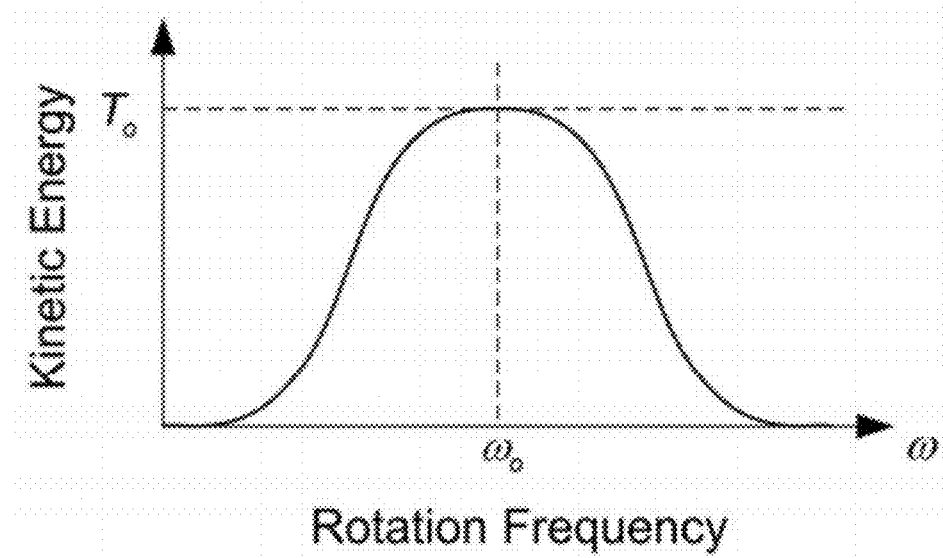
FIG. 21C illustrates the distribution of kinetic energy as a function of frequency of rotation of the rods, in accordance with an embodiment of the invention.

At some angular frequency greater than $\omega_o$ the moment $\mu$ cannot follow the field rotation and the system becomes destabilized. At much higher frequency, the motion substantially halts, since half of the time the field leads by less than $\pi/2$ and for the other half of the time it leads by greater than $\pi/2$. Thus, the two torques effectively cancel. From this reasoning, the kinetic energy shows a frequency dependence such as shown in FIG. 21C. Specifically, the kinetic energy T is:

$$T = 2 \times (\tfrac{1}{2})(m/2)(L/2)^2 (d\theta/dt)^2 \quad [10]$$

FIG. 21C is a graph expressing this dependence of kinetic energy of the rod on frequency of rotation in which the maximum energy $T_o = (ml^2/8)\omega_o^2$ where $\omega_o = d\theta/dt$. That is, the peak rotational kinetic energy available for a single rod depends on the rod mass, length, and is quadratic in the angular velocity up to the point where the rod cannot follow the field rotation.

With the above understanding of the formation and mechanical behavior of a rod of magnetic nanoparticles, the use of the system and methods as it applies to medical applications can be shown. The system of nanoparticles has been found to behave (and appear visually) as a group of flexible magnetic rods acting on occlusions in blood vessels. First, the treatment of the two characteristic problematic cases discussed with FIGS. 16A and 16B, above, will be shown with the introduction of rotating rods.

Figure 22A:
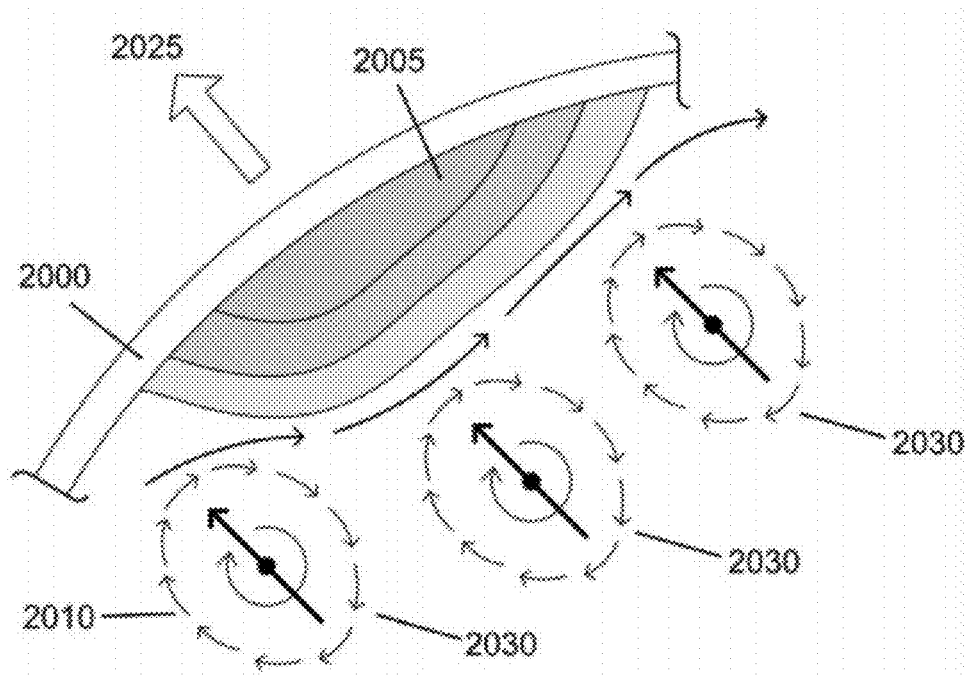
FIG. 22A illustrates the introduction of turbulence with spinning rods in a vessel with no flow, to treat the occlusion problem shown in FIG. 16A, in accordance with an embodiment of the invention.
Figure 23A:
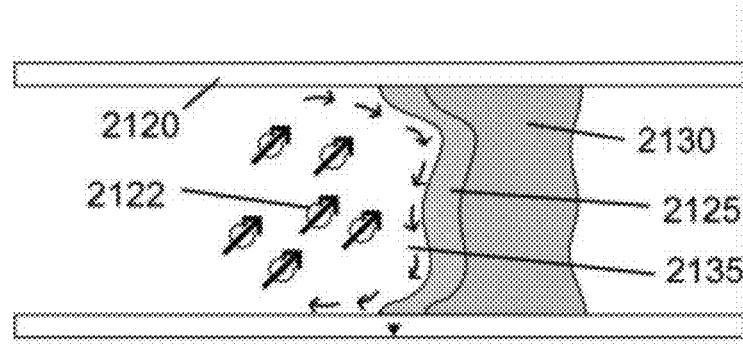
FIG. 23A is a cross section view of a group of rotating rods in a generally circular motion against a total occlusion in a vessel, in accordance with an embodiment of the invention.

FIG. 22A illustrates a practical benefit of the introduction of turbulence with spinning rods. FIG. 22A illustrates a portion of a vessel having complete spatial blockage being treated using the methods described herein, in contrast to the conventional treatment illustrated in FIG. 16A. FIG. 22A is a cross section view of lumen 2000 with no flow, having a clot 2005, with a fresh supply of thrombolytic drug 2010 being injected near the occlusion. Three spinning magnetic rods 2030 (not to scale) have been shown injected along with the fresh drug 2010, and they generate local turbulence as they are pulled in the direction 2025 of a rotating magnet source (not shown here). With a clockwise spinning rotation the rods are shown co-mingling with the fresh drug, and brushing the surface of the clot 2005 as they move slowly to the left as the external rotating magnetic field source moves. The tiny particles of clot 2005 accumulate at the right, where they will form a ball, when the rotation is continued, as illustrated in FIG. 23A.

In some embodiments, the removal of the clot 2005 occurs without mechanical scouring of the clot material. In some embodiments, the principal mechanism for removal of the clot 2005 is not the abrasion of the magnetic rods 2030 scraping pieces of the clot 2005. In some embodiments, the principal mechanism for removal of the clot 2005 is not due to hyperthermia caused by inductive heating of the magnetic rods 2030 arising from an alternating magnetic field. In some embodiments, the magnetic rods 2030 do not have an abrasive coating. In some embodiments, the magnetic rods 203 have a non-abrasive coating. The situation is to be compared with that of FIG. 16A, in a static application of drug that would have little mixing action, and must depend on lengthy time for removal of the clot. In some embodiments, the magnetic nanoparticles can be manipulated to form a vortex, e.g. predictably circulate, in a region of stagnant flow to better mix an adjunct, resulting in a more efficient chemical interaction.

Creating a vortex can also draw in more of the adjunct near the region of turbulent flow. The circulation can occur at a frequency greater than or equal to about 0.1 Hz and/or less than or equal to about 5 Hz, or a frequency greater than or equal to about 0.25 Hz and/or less than or equal to about 3 Hz, or overlapping ranges thereof.

Figure 22B:
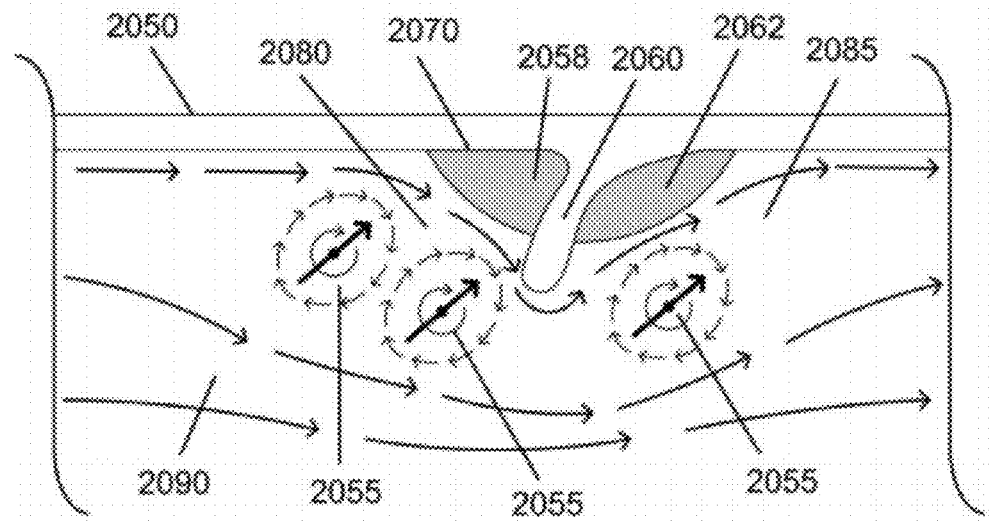
FIG. 22B exhibits motion and effect of drug delivery according to some embodiments for introduction of turbulence in the occluded flow category shown in FIG. 16B, in accordance with an embodiment of the invention.

FIG. 22B is a cross section view of the upper part of a lumen 2050 in which example embodiments of methods and devices are shown solving the problem of inefficient clot removal by standard methods in the case as shown in FIG. 16B. This case might represent partial blockage in a leg artery. In some embodiments, there is slowly flowing blood 2090 in the partially blocked lumen 2050, as was exhibited in FIG. 16B. Clot material 2058 and 2062 has built up around valve leaflet 2060, stiffening it and causing significant but not total flow reduction. In this case, the vessel 2050 is not totally closed, and the reduced flow is due to the partial occlusion and rigidity of rigid valve 2060. As described in relation to FIG. 16B the blood flow, though slow, carries off injected drug with inefficient contact with the occluding material. In some embodiments of the method, the actions of rotating scouring rods 2055 acting on clots 2058 and 2062 can be shown to greatly increase the drug contact, as well as provide gentle scuffing on a small scale. Turbulent flow in regions 2080 and 2085 is generated by the rotating rods 2055 whose relatively small and flexible structure can work in such regions without substantially or significantly damaging the vessel wall 2070 or valve leaf 2060. In some cases the removed magnetically infused material will be collected downstream by magnetic means.

In some embodiments, a principal mechanism for removal of the clot material 2058 and 2062 is not the abrasion of the rotating rods 2055 scraping pieces of the clot material 2058 and 2062. In some embodiments, the principal mechanism for removal of the clot material 2058 and 2062 is not due to hyperthermia caused by inductive heating of the rotating rods 2030 arising from a time-varying magnetic field. In some embodiments, the magnetic rods 2030 do not have an abrasive coating. In some embodiments, the rotating rods 2030 have a non-abrasive coating.

When the rotation is continued under certain conditions (especially low flow) the clot material and magnetic nanoparticles can form a magnetic ball, as described in FIG. 23B below. Again, without being bound by a particular theory, it is believed that as the magnetic nanoparticles circulate they may engage the surface of the thrombus. As the thrombus breaks into tiny pieces, the magnetic nanoparticles become encapsulated in a ball-like structure that comprises the magnetite and thrombus materials. This structure has several advantageous properties, in accordance with several embodiments of the invention.

1. The object can accelerate the destruction of the thrombus by increasing the surface area of interaction and by causing more efficient circulation of the thrombolytic drug.

2. The structure can capture smaller emboli, encasing them in the ball structure, thereby preventing them from escaping.

3. The structure can continue to break down slowly as that structure is lysed by the thrombolytic drug.

4. The structure can be recollected with a magnet-tipped device, thereby capturing the larger emboli and the magnetic nanoparticles.

With an appropriate rate of delivery of a drug, depending on the nature and age of a clot and of magnetic rod interaction, the magnetic rod scouring process can be arranged to mix clot material and rods, as described, to provide small, roughly spherical balls of clot material combined with the magnetic rods. Those conditions can be determined by the rate of application and concentration of the thrombolytic drugs during the magnetic procedure. Physicians trained in the treatment of occlusions can use judgment of the rate of delivery of drug in order to form the ball of desired or optimal properties (stiffness and size) for completion of the removal.

An example application of this technique is described as follows. FIG. 23A is a cross section view of a blood vessel 2120, totally occluded by a clot 2130, with no blood flow. Here magnetic rods 2122 are stirring the region just proximal to clot 2130 with clockwise rotation of the magnetic field, causing circulation pattern 2135. The mixing region 2125 contains a mixture of clot material, thrombolytic drug, and a small amount of magnetic rod material.

Figure 23B:
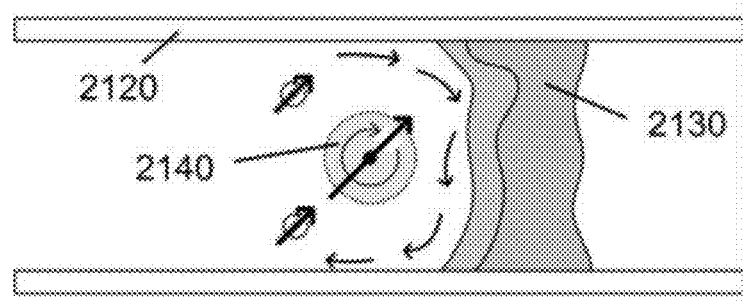
FIG. 23B is a cross section view of the rotation of rods starting to form a ball, in accordance with an embodiment of the invention.

In the cross section view of FIG. 23B, this rotational interaction in blood vessel 2120 has continued and a ball 2140 begins to form of material stripped from clot 2130 using captured emboli, and a small amount of magnetic rod material.

Figure 23C:
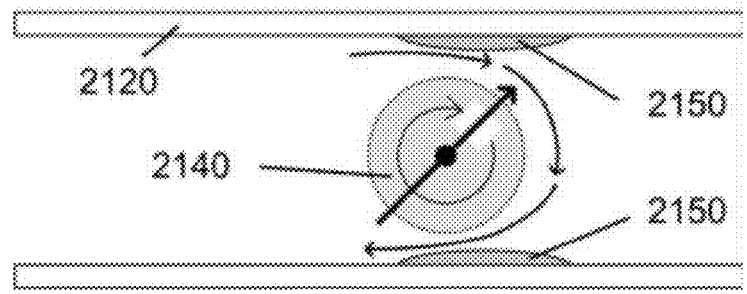
FIG. 23C is a cross section view of the rotating ball of rods and clot material having opened the obstructed vessel, in accordance with an embodiment of the invention.

In FIG. 23C, the rotating ball 2140 has become enlarged and accelerates the therapy. It has opened the blocked channel in vessel 2120, leaving minor remains 2150 of occlusion material. The ball 2140 is still rotating and held in location by the force from the gradient of the rotating magnetic source (e.g., magnet).

Figure 23D:
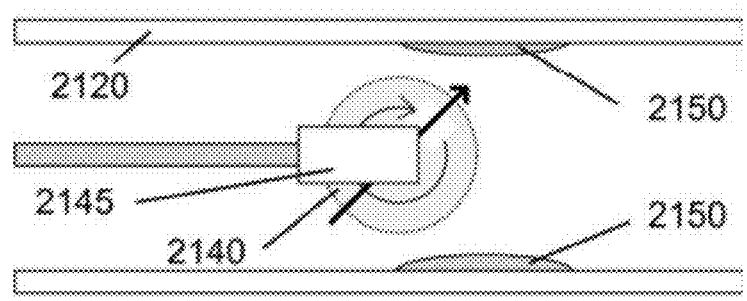
FIG. 23D is a cross section view of the ball of FIG. 23C being removed by a small magnet on a guide wire, in accordance with an embodiment of the invention.

FIG. 23D shows the means of capture and removal of completed clot ball 2140. At an appropriate time, before restored blood flow has pushed the thrombus ball 2140 downstream, a magnet-tipped probe 2145 is inserted and captures the ball structure 1040 for removal by retracting the magnet-tipped probe 2145.

Figure 24:
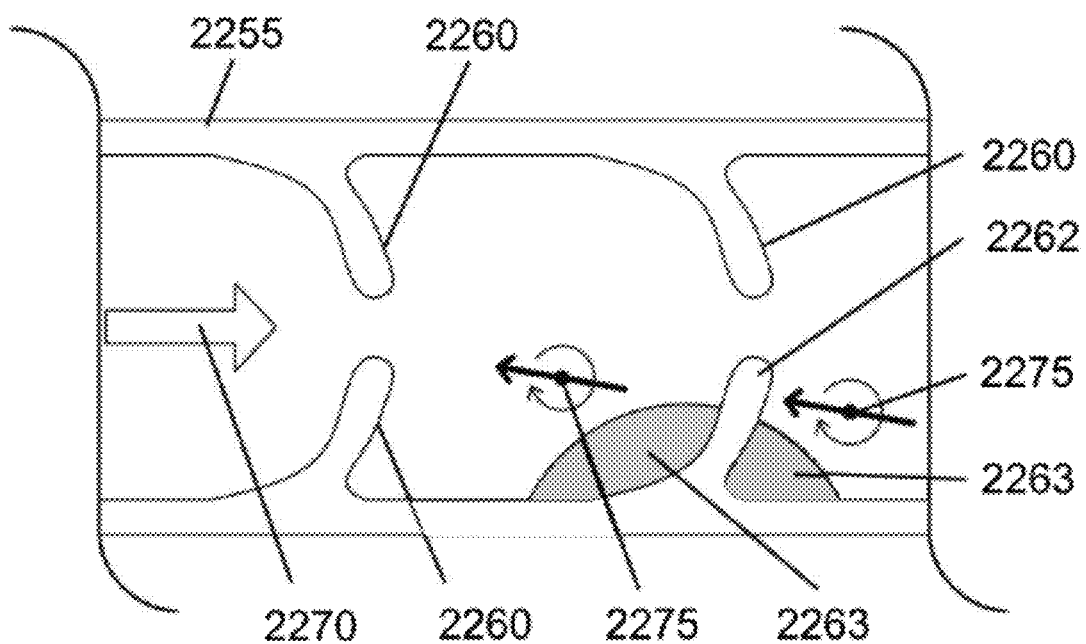
FIG. 24 is a cross section view of a vessel with rotating magnetic carriers applying therapeutic agents to safely remove occluding material on a valve leaflet in a blood vessel, in accordance with an embodiment of the invention.

FIG. 24 is a cross section view of blood vessel 2255 containing valve leaflets 2260, one of which, 2262, has occluding material 2263 that has stiffened valve 2262 to become non-functional. Blood is flowing slowly in the direction of arrow 2270. An external magnetic field generator, (such as depicted in FIG. 14 or FIG. 15), has generated a rotating field in this region into which rotating nanoparticle rods 2275 are acting on clot deposits 2263 in the manner shown, for example, in FIG. 22B above. The magnetic nanoparticle rods 2275 shown may actually be members of a large number of such rods in the space adjacent the clot deposits 2263. The rods 2275 are flexible and can be brushed to lengths shorter than the approximately one to two millimeters as described above, in order to function on the narrow corners of the clot deposits 2263. In laboratory tests, the rods 2275 have functioned to remove material in model spaces that were approximately 2 centimeters wide and 3 millimeters deep and removed approximately 100 cubic millimeters of thrombus material.

Figure 25:
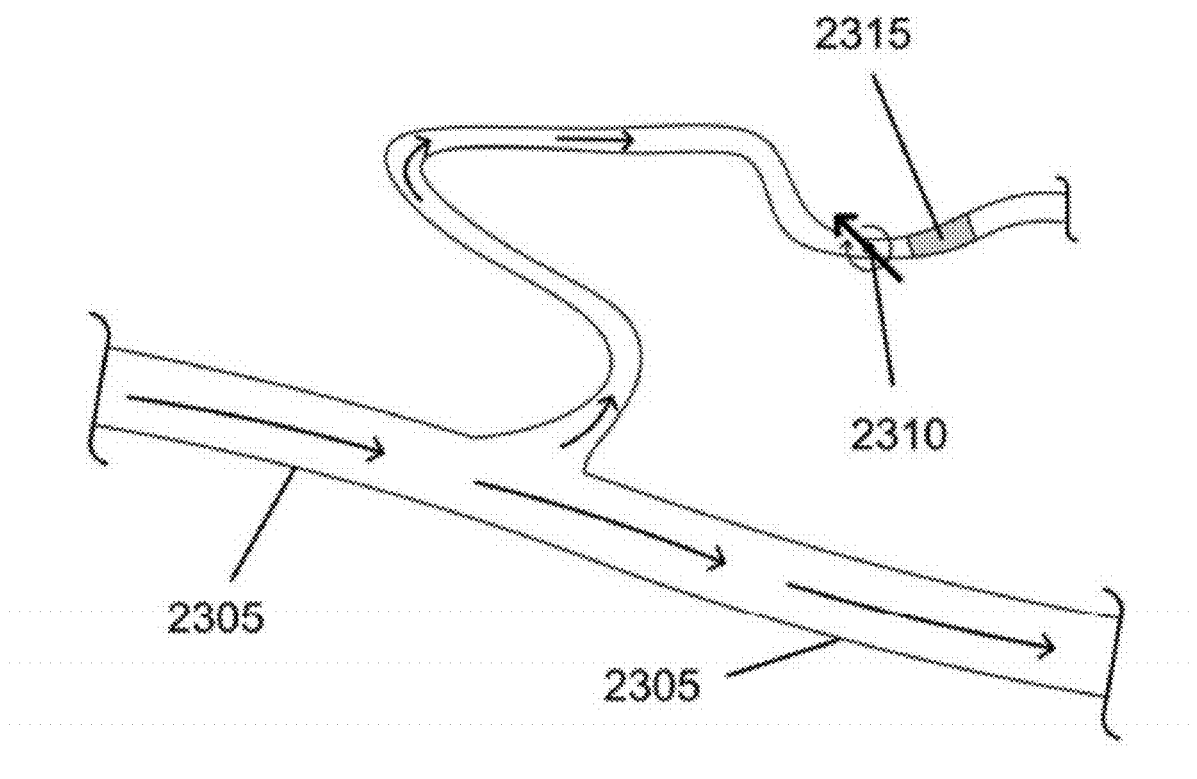
FIG. 25 illustrates the result of end over end motion of a magnetic rod "walk" along a path to a distant clot in a complex vessel, in accordance with an embodiment of the invention.

FIG. 25 is a cross section drawing of a small blood vessel 2300 branching off a larger vessel 2305. The small blood vessel 2300 may be tortuous as shown, but does not hinder the walking travel such as that of a magnetic rod 2310 shown approaching clot 2315, which might be a clot in a brain or otherwise. Accordingly, the systems and methods described herein advantageously facilitate movement of magnetic nanoparticles, and treatment of fluid obstructions, within tortuous or curved vasculature (such as the neurovasculature). Such small clots 2315 can be scrubbed as described for other, generally larger vessels such as 2255 in FIG. 24 above. The scrubbing can be generated to remove pieces of occluding material with the appropriate field and gradient choices. These removed particles may be up to a few microns in size, and may not cause further downstream damage. In accordance with several embodiments, an advantage of this method of clearing a clot such as clot 2315 is that the occlusion might be total and difficult to reach by conventional existing methods, but the external rotating field provided by the systems and methods described herein can walk the rods to the occlusion point. The thrombolytic drug may then be introduced, if possible, at the site of the clot 2315. At that point, the stirring activity of the magnetic rods 2310 can make the drug interact with the clot 2315 much faster than a static delivery.

Although magnetic nanoparticles are sufficient to gently clear delicate structures, it may sometimes be desirable to rapidly remove material quickly, as is the case for ischemic stroke, in which parts of the brain are starved of blood. The same principles used with magnetic nanoparticles may be employed with larger magnetic structures which are specifically designed to rapidly remove occlusions by mechanical abrasion while simultaneously increasing the flow of thrombolytic drugs to the blockage. These larger magnetic structures, termed here as thrombectomy devices, may be spheres with an abrasive material bonded on the surface. They can be sub-millimeter in size up to a millimeter or more, with the consideration that removal after the particular procedure is desirable. This technique can result in smaller residual emboli than is typically seen with conventional techniques. A further advantage of this method over existing procedures is the controllable magnetic character of the removed material. The thrombectomy device, which is depicted herein as a sphere with a magnetic moment (i.e., a "magnetic ball"), may be tethered to simplify retrieval of the device. In some embodiments, the thrombectomy device can be recovered in a manner similar to that proposed for the magnetic nanoparticles, namely, the use of a magnetically-tipped guide wire. The ball's surface may comprise any one or a combination of the following:

1. Contrast agent or agents which allow visualization with magnetic resonance imaging, X-ray, PET, ultrasound technologies, or other imaging modalities.

2. Drugs which accelerate destruction of the blockage.

3. Surface geometries designed and/or optimized to accelerate grinding.

4. Abrasive surfaces to accelerate grinding.

Figure 26A:
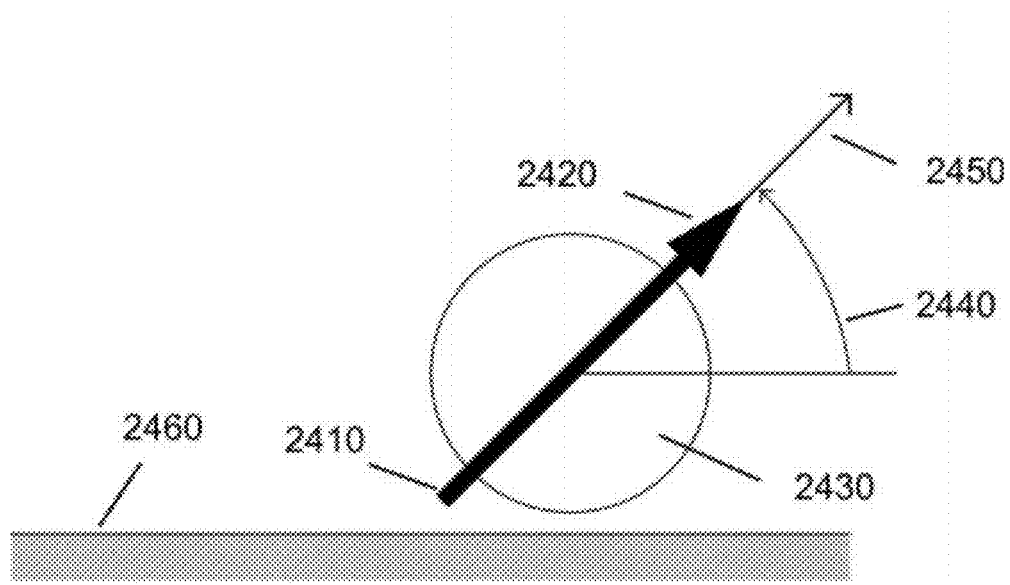
FIGS. 26A and 26B illustrate the generation of motion of a magnetically-enabled thrombectomy device which is depicted as a sphere, where (A) shows no field or gradient applied and (B) shows a field and gradient applied causing the sphere to move laterally, in accordance with an embodiment of the invention.

FIG. 26A illustrates elements of the basic operation of the magnetically-enabled thrombectomy device which is presented as a sphere 2430. The ball 2430 possesses a permanent magnetic moment with South 2410 and North 2420 ends. An externally applied magnetic field 2450 which advances in the counter-clockwise direction 2440 causes the ball to rotate. If the magnetic gradient is absent, as is the case in FIG. 26A, no traction is generated against the surface 2460 and the ball does not translate.

Figure 26B:
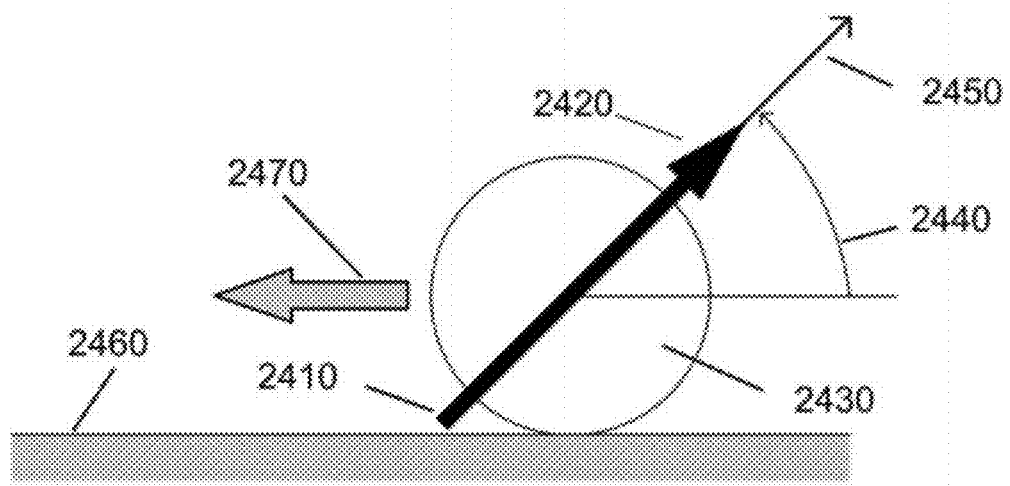

FIG. 26B depicts the same case as FIG. 26A except that a magnetic gradient 2480 is present in a substantially fixed direction 2480 which generates a force in the direction 2480 acting on the magnetic ball 2430 to press it against the vessel wall 2460. As a result, traction is created and translational motion occurs in direction 2470 with the counter clockwise rotation 2440 of the field.

An example application of this technique is described as follows. FIG. 27A is a cross section view of a blood vessel 2510, totally occluded, with no blood flow. As shown, a magnetic ball 2530 can stir the region just proximal to occlusion 2515 while mechanically grinding the occlusion's surface 2522. Contact against surface 2522 is created by a gradient in direction 2520 which results in a translational force in direction 2520. Clockwise motion of magnetic ball 2530 causes circulation pattern 2525 to be formed, which accelerates action of the thrombolytic drug.

In the cross section view of FIG. 27B, the rotational interaction in blood vessel 2510 has continued and ball 2530 has deeper penetration into occlusion 2515 in the translation direction 2520.

In FIG. 27C, the rotating magnetically-enabled ball 2530 has opened a blocked channel 2535 in vessel 2510, leaving minor remains of occlusion material. In some embodiments, the principal mechanism for removal of the occlusion 2515 is not the abrasion of the magnetic ball 2530 against the occlusion 2515, but is the increased exposure of the occlusion to a therapeutic agent (e.g., thrombolytic drug). In some embodiments, the principal mechanism for removal of the occlusion 2515 is not due to hyperthermia caused by inductive heating of the magnetic ball 2530 arising from a time-varying magnetic field. In some embodiments, the magnetic rods 2530 do not have an abrasive coating.

FIG. 27D shows a means of capture and removal of the magnetically-enabled ball 2530 from the vessel 2510. The external field 2520 is no longer rotated or is removed, which causes the ball 2530 to no longer translate to the right. At an appropriate time, before restored blood flow has pushed the magnetically-enabled ball 2530 downstream, a magnet-tipped probe 2540 is inserted and captures ball 2530 for removal by retracting magnet-tipped probe 2540.

Figure 28A:
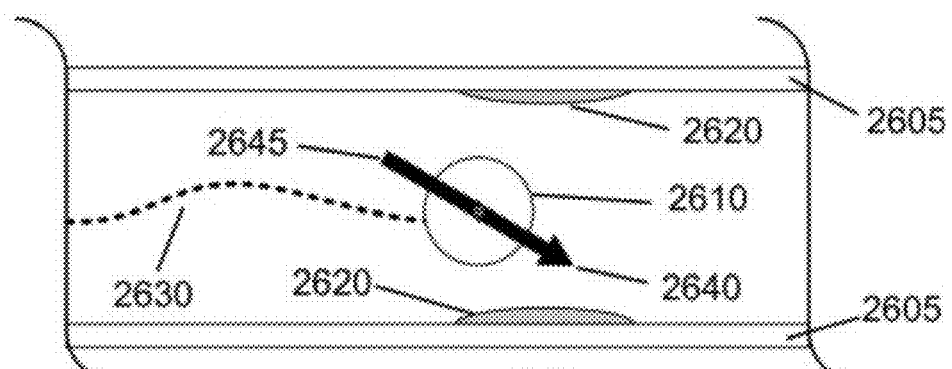
FIG. 28A is a cross section view illustrating a tethered magnetically-enabled thrombectomy sphere having opened an obstructed vessel, in accordance with an embodiment of the invention.

Cross sectional view FIG. 28A shows a tethered magnetically-enabled ball 2610 in vessel 2605. The tether 2630 allows the ball 2610 to rotate with the magnetic field, using attachments to be shown in FIG. 28B or 28C. In FIG. 28A, the North 2640 and South 2645 ends of the magnet are depicted at the ends of the black arrow. A free rotation of the magnetic field 2640-2645 allows grinding of the thrombus or plaque material 2620 inside of the vessel 2605. The tether 2630 ensures the magnet 2610 can be manually retrieved without the need of the magnetically-tipped wire 2540 that was depicted in FIG. 27D. In accordance with several embodiments, tether 2630 will not wind on the ball 2610 under rotation (for example, when designed according to methods and devices of FIGS. 28B and 28C).

Figure 28B:
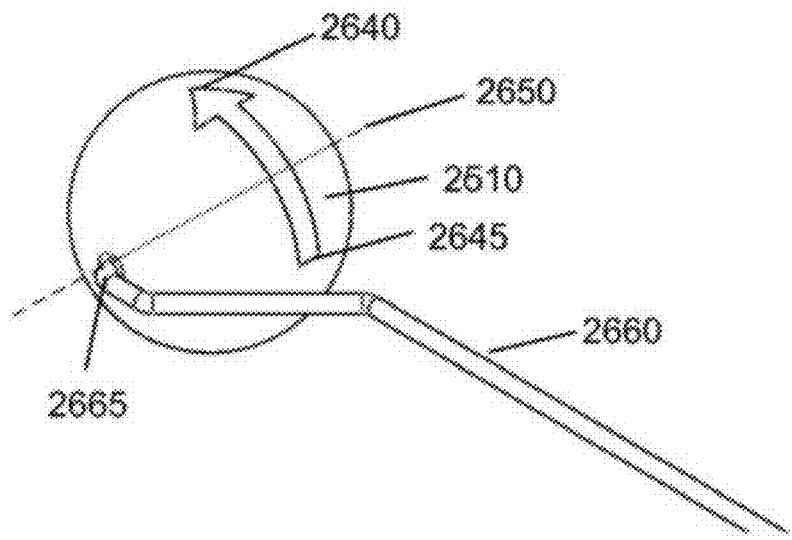
FIG. 28B illustrates an embodiment of a tethered magnetically-enabled thrombectomy sphere in which the tether runs through the magnetic sphere's rotational axis.

FIG. 28B shows a first embodiment of a tether 2660 which allows rotation around a rotational axis 2650 of magnetic ball 2610. As shown in FIG. 28B, a tether end 2665 is inserted through the rotational axis 2650 loosely to ensure free rotation about the rotational axis 2650. North 2640 and South 2645 arrow depicts the magnetization direction of ball 2610.

Figure 28C:
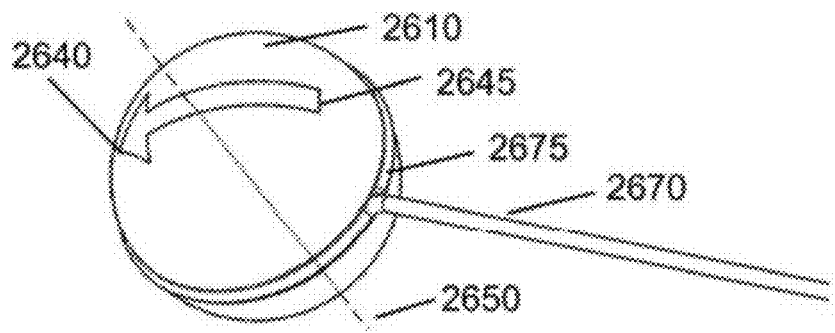
FIG. 28C is another example tether embodiment which loops around the magnet's rotational axis, in accordance with an embodiment of the invention.

FIG. 28C shows a second embodiment of a tether. Tether 2670 allows rotation around the rotational axis 2650 of the magnetic ball 2610 (perpendicular to a loop 2675). As shown in FIG. 28C, the tether comprises a loop 2675 which loosely surrounds the magnetic ball's rotational axis 2650 to ensure free rotation about the rotational axis 2650. The North 2640 and South 2645 ends of arrow 2680 depict the magnetization direction of ball 2610.

Figure 29:
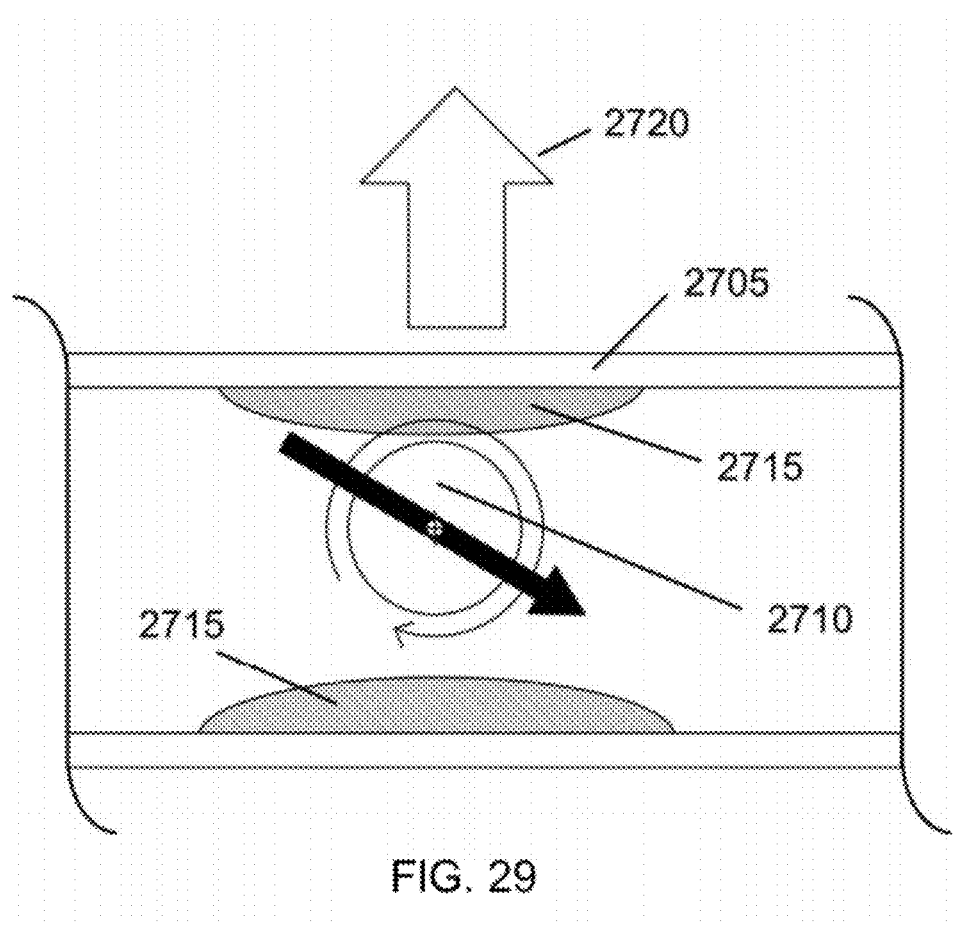
FIG. 29 is a cross section view of a rotating magnetically-enabled thrombectomy sphere in circular motion against plaque on vessel walls, in accordance with an embodiment of the invention.

The technologies described herein also may be used in removing vulnerable plaque 2715 on a vessel 2705 wall, as depicted, for example, in FIG. 29. In FIG. 29, a cross section view of a blood vessel 2705 is shown with vulnerable plaque 2715 on the top and bottom of the vessel 2705. A rotating magnetic ball 2710 is shown grinding the plaque 2715 in a manner similar to that used on the occlusion 2515 depicted in FIG. 27C and the tethered embodiment in FIG. 28A. This is made possible by using an externally-generated magnetic gradient 2720 to direct the action upwards towards the plaque 2715. In some embodiments, therapeutic agents (e.g., thrombolytic drugs) may also be present to substantially dissolve the removed (e.g., ejected) plaque material.

To image the magnetic nanoparticles and magnetically-enabled thrombectomy device with modern imaging technologies, the particles can possess a coating which makes them substantially opaque to that imaging technology. Example contrast coatings include contrast coatings detectable by x-ray, PET, MR and ultrasound imaging technologies. Such coatings can advantageously provide the ability to reconstruct a vessel which would normally be invisible due to the lack of blood flow in that region. Likewise, the ability to control and recollect the magnetic nanoparticles can result in less toxic side effects, which may result from use of traditional contrast agents. For example, X-ray contrast agents typically require multiple injections because they are swept away with blood flow and are not able to travel in high concentrations down low-flow vessels.

Figure 30A:
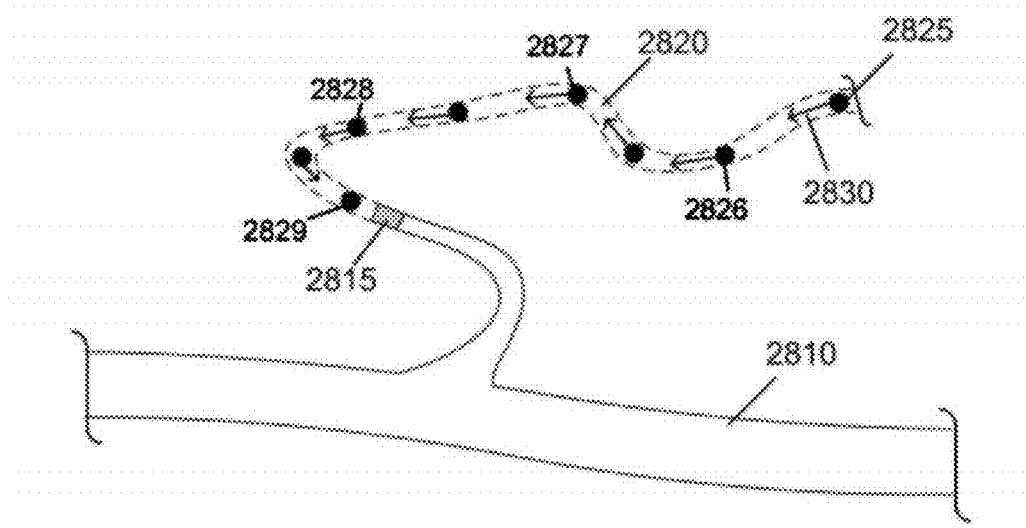
FIG. 30A illustrates the result of end over end motion of a magnetic rod or magnetic ball "walk" along a path to a distant clot in a complex vessel as imaged by an imaging technology, in accordance with an embodiment of the invention.

FIG. 30A is a cross section drawing of a small blood vessel 2820 branching off a larger vessel 2810. The small vessel 2820 may be tortuous, as shown, but does not hinder the walking travel of magnetic rod collection and/or the rolling motion of a magnetically-enabled ball. Both technologies are schematically depicted as starting at the right side of the small vessel 2825 and approaching a blockage 2815. At subsequent points in time, the location of the magnetic ball or magnet rod collection 2825 is identified at the points indicated by 2826, 2827, 2828, and 2829. The translation direction of the magnetic rod collection or magnetically-enabled ball is indicated by the arrow 2830 extending from the body.

Figure 30B:
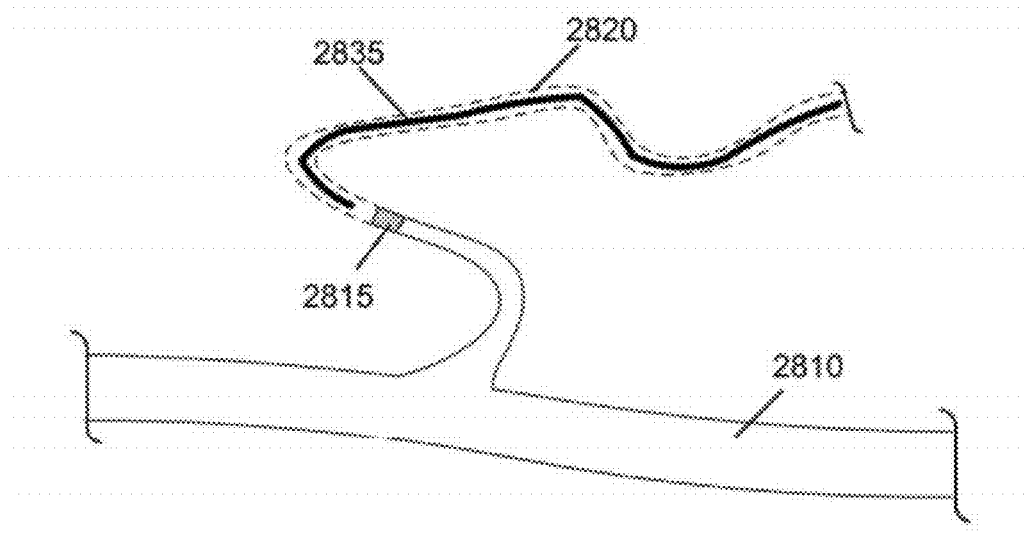
FIG. 30B illustrates the ability to recreate the path based on the measurements made in FIG. 30A.

FIG. 30B is the same cross section drawing depicted in FIG. 30A. In this view, the imaged locations of the magnetic rod collection or the magnetically-enabled ball are connected, thereby allowing a computer to reconstruct the path 2835 traveled. This path can be referenced against preoperative images to confirm the anatomy and to plan procedures using navigation along the path 2835.

Compositions for Use in the System

Various formulations of magnetic nanoparticles, whether formulated in combination with pharmaceutical compositions or not, may be used for administration to a patient. Those of skill in the art will recognize how to formulate various therapeutic agents (e.g., pharmaceutical compositions, drugs and compounds) for co-administration with the magnetic nanoparticles hereof, or administration separate from the nanoparticles. In some embodiments, various formulations of the magnetic nanoparticles thereof may be administered neat (e.g., pure, unmixed, or undiluted). In some embodiments, various formulations and a pharmaceutically acceptable carrier can be administered, and may be in various formulations. For example, a pharmaceutically acceptable carrier can give form or consistency, or act as a diluent. Suitable excipients include but are not limited to stabilizing agents, wetting and emulsifying agents, salts for varying osmolarity, encapsulating agents, buffers, and skin penetration enhancers. Example excipients, as well as formulations for parenteral and non-parenteral drug delivery, are set forth in Remington, The Science and Practice of Pharmacy 20th Ed. Mack Publishing (2000) the disclosure of which is hereby expressly incorporated by reference herein.

The magnetic nanoparticles can be formed having a mono-crystalline core with diameters greater than or equal to about 20 nm and/or less than or equal to about 200 nm, diameters greater than or equal to about 50 nm and/or less than or equal to about 100 nm, or diameters greater than or equal to about 60 nm and/or less than or equal to about 80 nm, overlapping ranges thereof, diameters less than or equal to 170 nm, or diameters of any integer between about 20 nm and about 200 nm. The mono-crystalline core can be advantageous because the structure allows for stronger magnetic interactions when compared with magnetic particles of similar sizes having poly-crystalline cores. Such nanoparticles having reduced magnetic effects can be advantageous for use in imaging applications, such as using them as contrast agents in MRI. The mono-crystalline magnetic nanoparticles described herein can also include a coating of polyethylene glycol (PEG), polyethylene oxide (PEO), polyoxyethylene (POE) or other polymer, which can serve as a platform for attaching other drugs.

Administration of Magnetic Nanoparticles

In some embodiments, the magnetic nanoparticles are formulated for administration by injection (e.g., intraperitoneally, intravenously, subcutaneously, intramuscularly, etc.), although other forms of administration (e.g., oral, mucosal, etc.) can be also used depending on the circulatory system blockage to be treated. Accordingly, the formulations can be combined with pharmaceutically acceptable vehicles such as saline, Ringer's solution, dextrose solution, and the like. The particular dosage regimen, i.e., dose, timing and repetition, will depend on the particular individual, that individual's medical history, and the circulatory system blockage to be treated. Generally, any of the following doses may be used: a dose of about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or less, is administered. Empirical considerations, such as the half-life of a thrombolytic drug, generally will contribute to determination of the dosage.

In accordance with several embodiments, systems and methods are provided for delivering non-dispersible or difficult to disperse agents (such as embodiments of the magnetic nanoparticles described herein). Administering magnetic nanoparticles by injection can present challenges where a substantially consistent infusion mass is desired as a function of time. The infusion mechanism can include syringes, drip bags, reservoirs, tubing, drip chambers, other mechanisms, or any combination of these. Magnetic particles can be dispersed in solutions such as, for example, saline, Ringer's solution, dextrose solution, and the like. After a certain amount of time has elapsed in such solutions, magnetic particles can settle near the bottom of the solution due primarily to gravitational forces on the particles possibly resulting in an inconsistent infusion mass.

For example, in certain applications, the magnetic nanoparticles are supplied in a single-dose vial containing about 500 mg of magnetic nanoparticles dispersed in about 17 mL of phosphate buffered saline (PBS), and are designed to be infused over the course of about an hour. These magnetic nanoparticles can settle out of dispersion in about 5 to 10 minutes. Thus, the magnetic nanoparticles would settle faster than the time used to administer them, thereby causing the infusion mass to be inconsistent.

Some embodiments of the magnetic nanoparticles described herein are non-dispersible or difficult to disperse in a fluid. Some embodiments of the magnetic nanoparticles described herein include a magnetically-strong, relatively large, single-crystalline core having a diameter greater than or equal to about 50 nm and/or less than or equal to about 200 nm. The magnetic nanoparticles can also be coated with a relatively thin (e.g., less than or equal to about 5 nm, 10 nm, 20 nm, etc.) coating (e.g., polyethylene glycol coating) to reduce the charge associated with the particles. For example, the relatively thin coating can possess less than 20% of the volume of the magnetic core. In one embodiment, a 70 nm diameter magnetite nanoparticle can have a 1 nm coating such that the coating volume is 9% of the magnetic core. The relatively thin coating advantageously can facilitate control of the magnetic nanoparticles and structuring of the nanoparticles by agglomeration or grouping into chains or rods. In several embodiments, the shell coating is thin enough such that the ability of the magnetic nanoparticles to mutually interact is substantially reduced. In various embodiments, the shell coating can be less than 50%, less than 45%, less than 40%, less than 35%, less than 30%, less than 25%, less than 20%, less than 15%, less than 10%, or less than 5% of the volume of the magnetic core of the nanoparticle. To disperse such nanoparticles in a fluid, e.g. saline, the thickness of the nanoparticle coating can be substantially increased and/or the viscosity of the dispersion medium can be increased. In some embodiments, systems and methods are provided for maintaining a substantially consistent infusion mass without altering the thickness of the nanoparticle coating or the viscosity of the dispersion medium.

Magnetic particles can be made more dispersible by coating the particles with a relatively thick coating. As an example, a relatively thick coating can be applied to magnetic nanoparticles to ensure the nanoparticles remain in steric repulsion, such as magnetite or hematite nanoparticles coated with Dextran or polyethylene glycol surrounding a relatively small polycrystalline, magnetic core (e.g., the magnetic core has a diameter less than or equal to about 20 nm). In some embodiments, systems and methods for maintaining a consistent infusion mass can infuse magnetically strong particles without a relatively thick coating, e.g., magnetic nanoparticles described herein having a single-crystalline core with a diameter greater than or equal to about 20 nm and/or less than or equal to about 200 nm. In some embodiments, the relatively thick coating prevents the magnetic particles from structuring effectively because the magnetic cores are mechanically prevented from sufficiently nearing one another due to the buffering of the coating. Magnetic particles can experience steric repulsion because they have a relatively thick coating that buffers the interaction of the magnetic particles such that they remain substantially dispersed throughout the infusion process. In some applications, magnetic particles are coated with a relatively thick coating to reduce the magnetic susceptibility of the particles, like when the magnetic particles are used as contrast agents for use in magnetic resonance imaging.

In some embodiments, magnetic particles are coated with biodegradable substances, hydrophobic drugs, or other such coatings. Such coatings can be effective in increasing the dispersion of the particles in a solution. In some embodiments, the magnetic nanoparticles described herein and the infusion methods and systems described herein advantageously allow the magnetic nanoparticles to substantially remain in dispersion throughout an infusion process without experiencing steric repulsion and/or without requiring a relatively thick coating to facilitate dispersion.

In some embodiments, a system for delivering agents that are not readily dispersed in a solution to ensure predictable delivery of the agents in the solution comprises a pump (e.g., syringe pump) that, in use, pushes a solvent through tubing towards a subject. The agent delivery or infusion system can comprise an inlet tubing coupled to the pump that, in use, transports the solvent from the pump and a reservoir coupled to the inlet tubing that, in use, holds at least a portion of a solute comprising the agents that are not readily dispersed in the solution. In some embodiments, the system comprises an agitating mechanism coupled to the reservoir that, in use, agitates the solvent and the solute to create a dispersed solution and an outlet tubing coupled to the reservoir that, in use, transports the dispersed solution to the subject. In some embodiments, an infusion and delivery system comprises a support structure and an IV drip bag coupled to the support structure that, in use, holds at least a portion of the solution with the agents that are not readily dispersed and an outlet tube coupled to the IV drip bag that, in use, transports the dispersed solution to the subject.

In some embodiments, an infusion system for delivering agents that are not readily dispersed in a solution to ensure predictable delivery of the agents in the solution comprises a syringe pump that, in use, controls dispersal of contents of two or more syringes. An outlet tubing section can be coupled to each of the syringes. In some embodiments, a manifold is coupled to the outlet tubing sections that, in use, joins the solution from two or more of the syringes for delivery to a subject. The manifold can comprise a manifold valve that, in use, controls fluid flow along the manifold. A delivery tube can be coupled to the manifold that delivers the mixed solution from the manifold to the subject. The delivery tube can include an outlet valve that, in use, controls fluid flow from the manifold to the delivery tube. In some embodiments, the syringe pump transfers a portion of the solution from a first syringe to a second syringe by dispersing the solution from the first syringe and collecting the solution with the second syringe such that the movement of the solution from the first syringe to the second syringe agitates the solution to maintain dispersion. In some embodiments, at least one of the plurality of syringes contains a saline solution.

Figure 31:
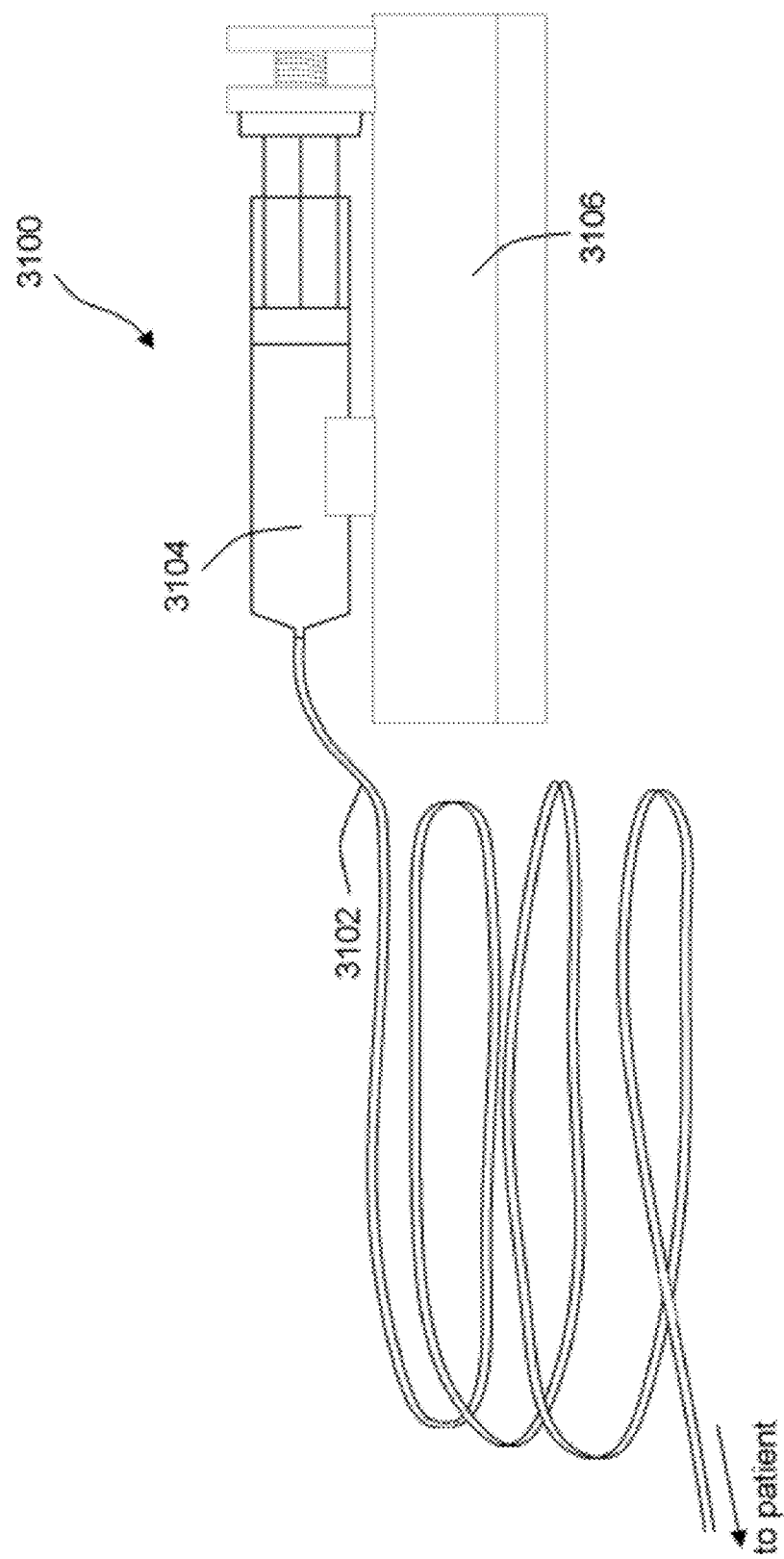
FIG. 31 illustrates an embodiment of an infusion system having micro-bore tubing.

In accordance with several embodiments, dispersion of the magnetic nanoparticles is at least partially maintained through the use of micro-bore tubing. Micro-bore tubing can be provided in the infusion mechanism to keep particles entrained in the infusate during the infusion process. Typical infusion sets include tubing having an inner diameter of about 4 mm. By decreasing the diameter of the tubing, infusion velocity is increased for a given infusion rate. This increase in velocity can be sufficient to reduce the amount of particles that settle in the tubing of the infusion mechanism such that the infusion mass remains substantially consistent throughout the infusion process. For example, a micro-bore tubing can have an inner diameter of less than or equal to about 1 mm, less than or equal to about 0.7 mm, less than or equal to about 0.5 mm, and/or less than or equal to about 0.3 mm. The inner diameter can depend on the desired fluid velocity through the tubing, the diameter of the particles to be infused, the length of tubing desired, or any combination of these. FIG. 31 illustrates an embodiment of an infusion system 3100 having micro-bore tubing 3102 that is at least partially pre-filled with a particle dose that is administered (e.g., pushed) to the patient with sterile saline 3104 from a syringe pump 3106.

Figure 32A:
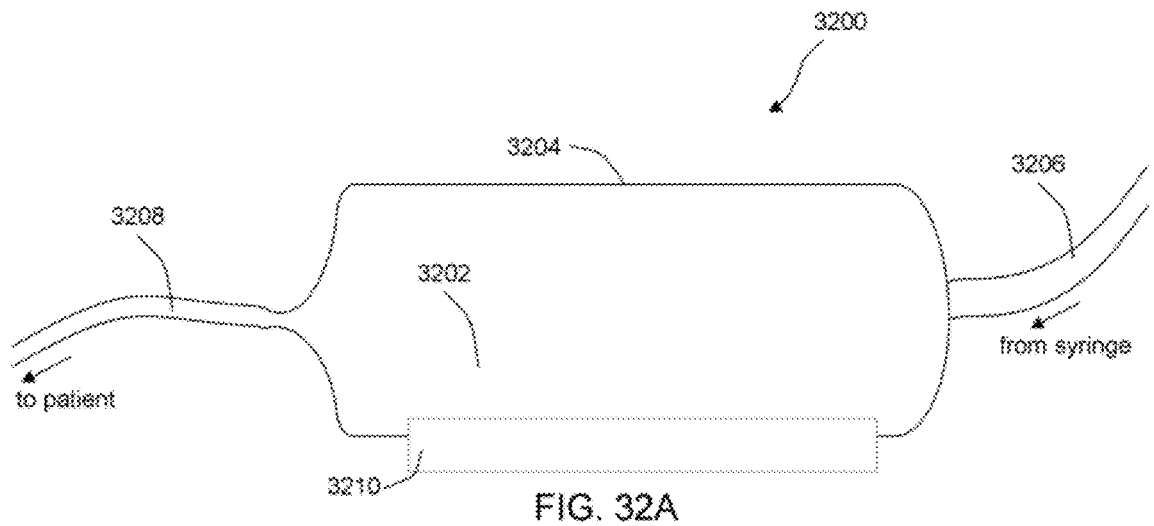
FIGS. 32A and 32B illustrate embodiments of infusion systems having ultrasonic transducers to maintain dispersion of an infusate.
Figure 32B:
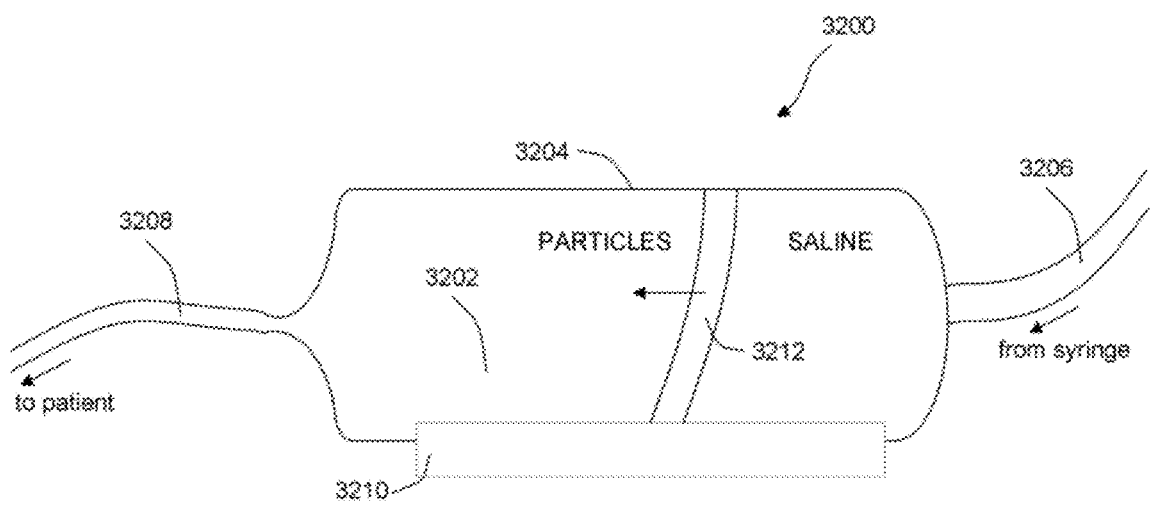

In some embodiments, the dispersion of the particles is at least partially maintained through the application of ultrasonic energy. FIG. 32A illustrates an example of such a system 3200. The example system 3200 includes a particle volume 3202 partially contained within a reservoir 3204, inlet tubing 3206 from a syringe pump, outlet tubing 3208 leading to a patient, and an ultrasonic transducer 3210 in contact with the reservoir 3204. The ultrasonic transducer 3210 can produce a timed (e.g., periodic) ultrasonic pulse to maintain the dispersion in the reservoir 3204. Infusion of the magnetic nanoparticles can be driven by a saline infusion via a syringe and syringe pump (not shown). In some embodiments, the ultrasonic transducer 3210 delivers substantially continuous ultrasonic energy to the reservoir 3204. In certain embodiments, the reservoir 3204 includes coiled infusion tubing (not shown) in a medium (e.g., a liquid or gel) configured to transmit ultrasonic energy to the tubing. The system 3200 delivering the ultrasonic energy can include, for example, ultrasonic transducers, ultrasonic pads, ultrasonic vibrators, ultrasonic stirrers, or any combination of these. In some embodiments, the outlet tubing 3208, or a portion of the outlet tubing 3208, can be micro-bore tubing configured to maintain dispersion of the particles upon delivery to the patient. In some embodiments, as illustrated in FIG. 32B, the reservoir 3204 can include a diaphragm 3212 that reduces the internal volume for the particle dispersion 3202 in response to increasing volume from the syringe/syringe pump infusion. As a result, the diaphragm 3212 pushes the particle dispersion 3202 in the reservoir 3204 into the outlet tubing 3208 as the saline infusion from the syringe pump enters the reservoir from the inlet tubing 3206.

Figure 33:
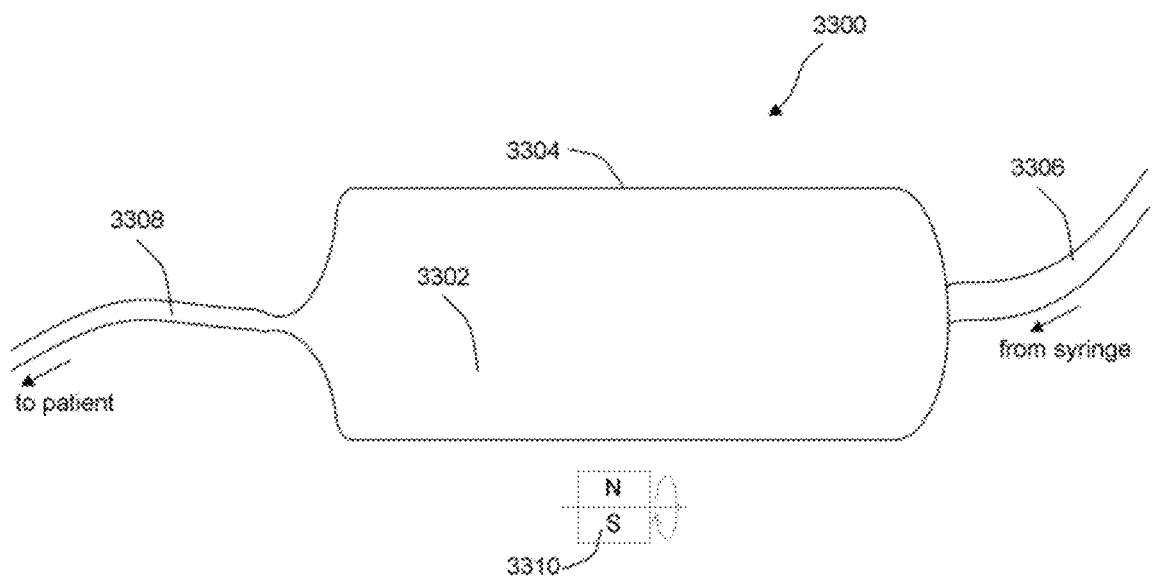
FIG. 33 illustrates an embodiment of an infusion system employing magnetic energy to maintain dispersion of an infusate.

In some embodiments, the dispersion of the magnetic nanoparticles is at least partially maintained through the application of magnetic fields. FIG. 33 illustrates an example of a system 3300 having a reservoir 3304 with a particle volume 3302, an inlet tube 3306 from a syringe, an outlet tube 3308 to a patient, and at least one magnet 3310 configured to produce a time-varying magnetic field. The magnetic nanoparticles can respond to the time-varying magnetic field by moving within the dispersion 3302 to substantially maintain a consistent infusion mass. The one or more magnets 3310 can be permanent magnets configured to rotate to produce a time-varying magnetic field. The one or more magnets 3310 can be electromagnets that have varying currents induced through them to produce a time-varying magnetic field. The one or more magnets 3310 can be any combination of permanent magnets and electromagnets. In some embodiments, more than one rotating magnet 3310 is spaced around the reservoir 3304, rotating in similar or different planes. The magnetic field can vary with a frequency greater than or equal to about 1 Hz and/or less than or equal to about 100 Hz, greater than or equal to about 5 Hz and/or less than or equal to about 50 Hz, and/or greater than or equal to about 10 Hz and/or less than or equal to about 30 Hz, greater than or equal to about 1 Hz and/or less than or equal to about 10 Hz, or overlapping ranges thereof, less than 100 Hz, less than 50 Hz, less than 30 Hz, less than 10 Hz. In some embodiments, the outlet tubing 3308, or a portion thereof, includes micro-bore tubing as described herein with reference to FIG. 31. In certain embodiments, the reservoir 3304 includes a diaphragm (not shown) that reduces the internal volume for the particle dispersion 3302 in response to increasing volume from the syringe/syringe pump infusion, similar to the ultrasonic system 3200 illustrated in FIG. 32B.

Figure 34:
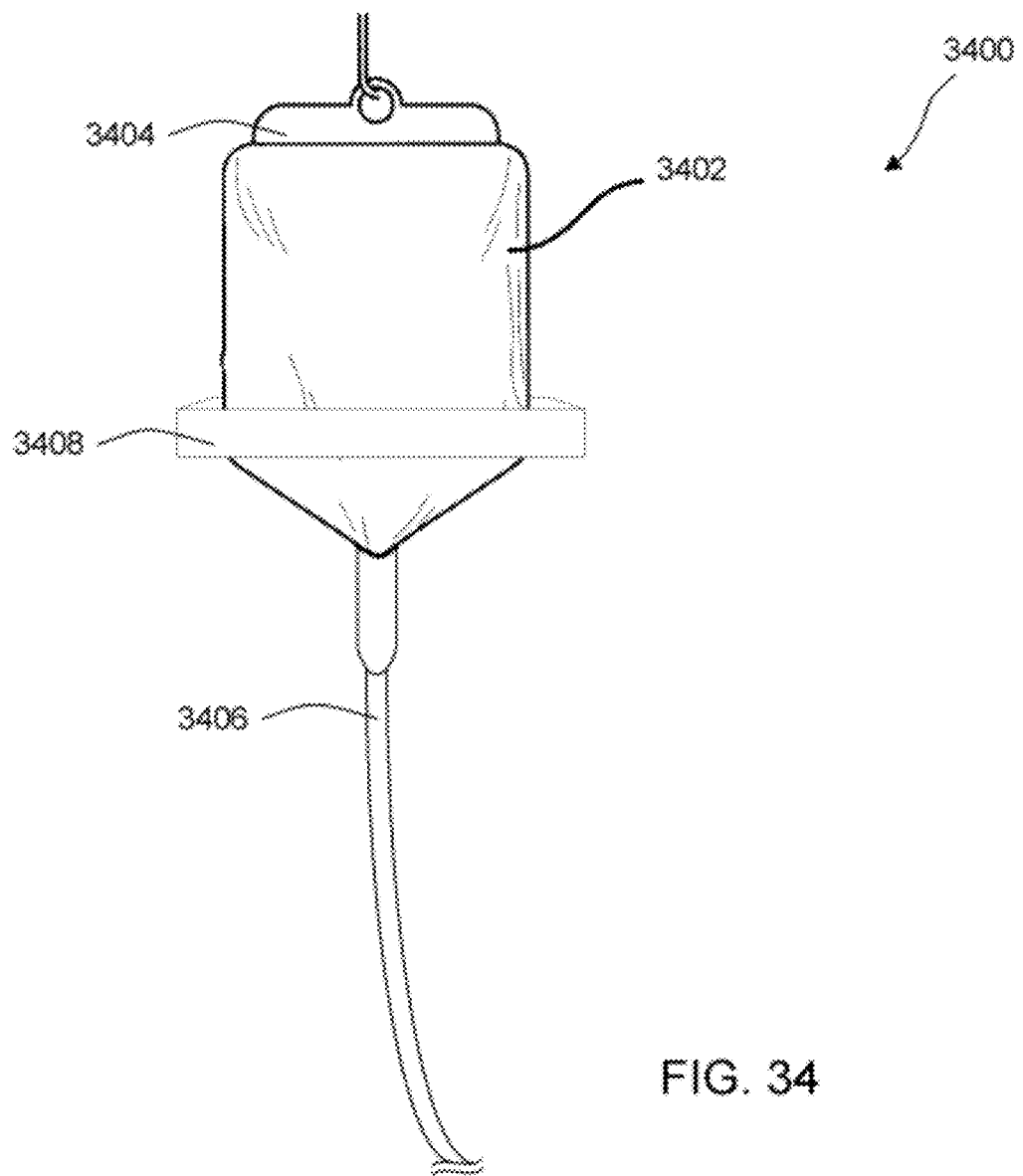
FIG. 34 illustrates an embodiment of an infusion system having a mechanical agitation system configured to maintain dispersion of an infusate.

In some embodiments, the dispersion of the magnetic nanoparticles is at least partially maintained through the application of mechanical agitation. FIG. 34 illustrates an example of a system 3400 having a drip bag 3402, a support structure 3404 for supporting the drip bag 3402, an outlet tube 3406 to the patient, and a mechanical agitator 3408 coupled to the drip bag 3402 and/or support structure 3404. In some embodiments, the system includes a drip chamber with a conical bottom (not shown) coupled to the drip bag 3402 and the outlet tube 3406 which allows a user to view and/or control flow into the outlet tube 3406. The dispersion can be maintained by continuous or timed agitation of an IV infusion drip bag 3402 through repeated squeezing of the drip bag 3402. In certain embodiments, the agitator 3408 comprises a mechanically actuated bar that squeezes a portion of the bag 3402 in a timed, continuous, periodic, and/or rhythmic manner. The mechanical agitation 3408 can be repeated with a frequency greater than or equal to about 0.1 Hz and/or less than or equal to about 5 Hz, or a frequency greater than or equal to about 0.25 Hz and/or less than or equal to about 3 Hz, or overlapping ranges thereof. In some embodiments, the agitator 3408 can be an air bladder, or balloon, coupled to a compressor that pulses air to the bladder, pauses to allow the air from the bladder to bleed into the drip bag 3402, and then repeats. In some embodiments, the agitator 3408 can be a mechanical vortexer configured to mechanically agitate the particle container. In some embodiments, the dispersion in the drip bag 3402 can be maintained through any combination of mechanical agitation, ultrasonic energy, and magnetic energy as described herein. In some embodiments, the outlet tubing 3406, or a portion thereof, includes micro-bore tubing as described herein with reference to FIG. 31.

Figure 35:
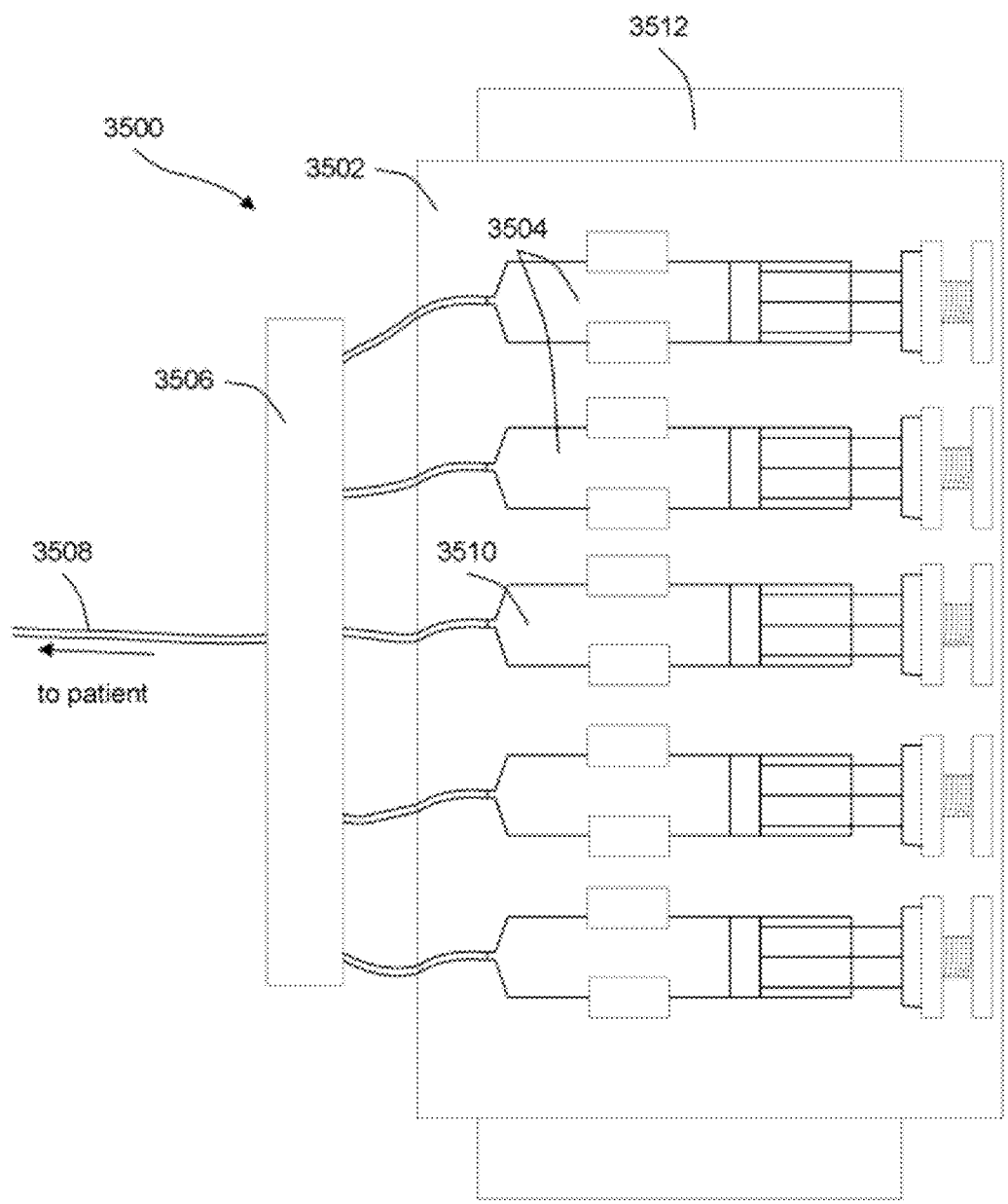
FIG. 35 illustrates an embodiment of an infusion system employing multiple bolus cartridges.

In some embodiments, the infusion mass is delivered using multiple bolus cartridges at timed intervals (e.g., periodic or randomized). FIG. 35 illustrates an example embodiment of such an infusion system 3500. The system 3500 includes an infusion pump 3502, multiple syringes 3504 or other delivery mechanisms, the syringes being coupled to a multi-connector or manifold 3506, the multi-connector or manifold 3506 coupled to outlet tubing 3508. The multiple syringes 3504 can be preloaded with individual doses and at least one syringe with saline 3510 can be included to infuse (e.g., push) each dose down the outlet tubing 3508 and/or flush the infusion line. In some embodiments, ultrasound and/or magnetic energy 3512 can be applied to the injection pump 3502 to maintain dispersion in one or more syringes 3504. In some embodiments, the outlet tubing 3508, or a portion thereof, includes micro-bore tubing such as described herein with reference to FIG. 31.

Figure 36A:
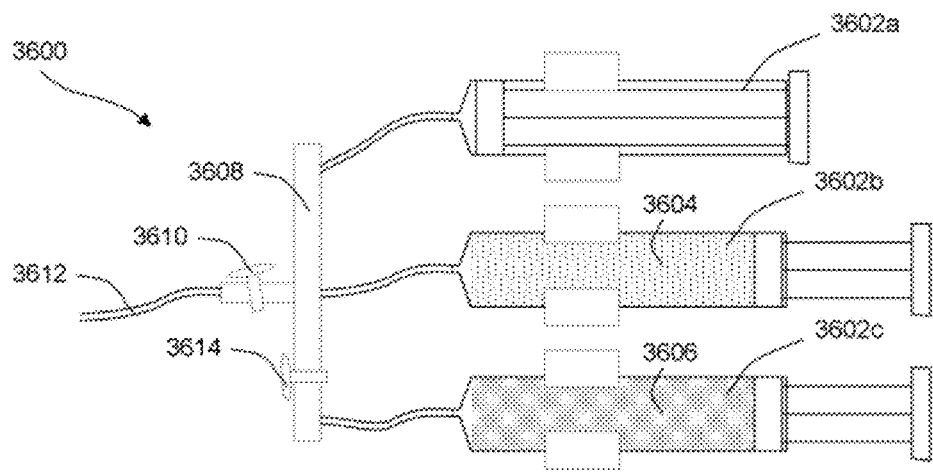
FIGS. 36A and 36B illustrate an embodiment of an infusion system employing fluid dynamic mixing to maintain dispersion of an infusate.
Figure 36B:
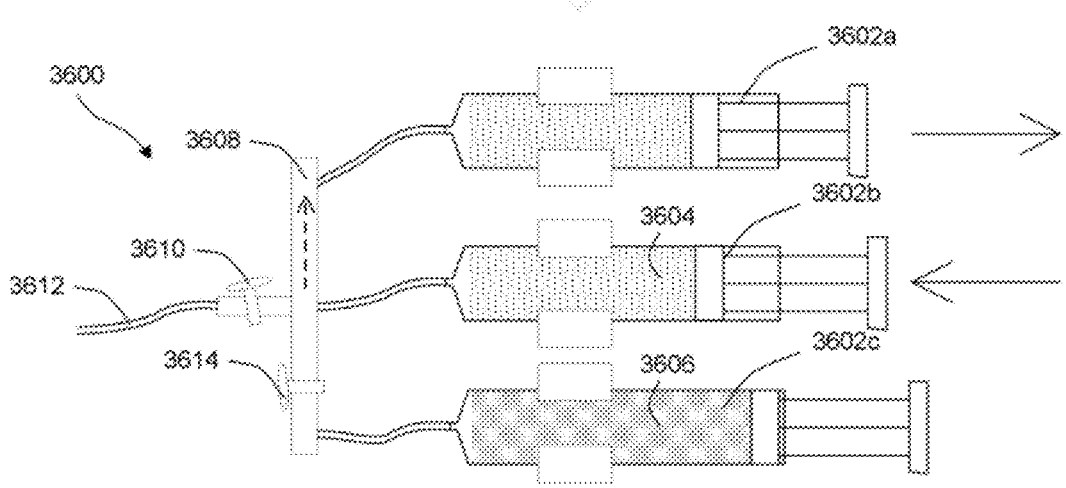

In some embodiments, the dispersion of the particles is at least partially maintained through the use of fluid dynamic mixing. FIG. 36A illustrates an example of such a fluid dynamic mixing system 3600. In this example, the fluid dynamic mixing system 3600 includes continuously mixing syringes 3602 wherein a first syringe 3602b includes the dispersion 3604, a second syringe 3602a is empty, and a third syringe 3602c includes a saline solution 3606. The syringes 3602 are fluidicly coupled by a manifold 3608. The system 3600 includes a valve 3610 controlling flow to an outlet tube 3612. The fluid dynamic mixing system 3600 can have one or more saline valves 3614 to control the introduction of saline 3606 into the manifold 3602 and/or outlet tubing 3612. The fluid dynamic mixing system 3600 can function by having the empty syringe 3602a withdraw at substantially the same time and/or rate as the dispersion syringe 3602b delivers, thereby transferring the dispersion 3604 from one syringe to the other in a substantially continuous manner, as depicted in FIG. 36B. This substantially continuous motion of the fluid can be sufficient to maintain the dispersion. At defined time intervals, the valve 3610 could open to allow the appropriate volume of solution to be delivered to the subject, after which the valve 3610 can close so that the mixing can continue. The saline syringe 3602c can be included and used to flush the dispersant 3604 from the tubing 3612 into the subject. For example, in a dynamic mixing phase the saline valve 3614 can be closed to substantially prevent the saline solution from exiting a saline solution portion of the manifold 3608, and the valve 3610 can be closed to substantially prevent the solution from flowing from the manifold 3608 to the outlet tube 3612. As another example, in a solution distribution phase the saline valve 3614 can be closed to substantially prevent a the saline solution from exiting a saline solution portion of the manifold 3608, and the valve 3610 can be open to allow the solution to flow from the manifold 3608 to the outlet tube 3612. As another example, in a flushing phase the valve 3610 and the saline valve 3614 can be open to allow the saline solution to flow from the manifold to the outlet tube 3612. In some embodiments, the outlet tubing 3612, or a portion thereof, includes micro-bore tubing such as described herein with reference to FIG. 31.

Having described the magnetomotive stator system and methods of controlling magnetic nanoparticles and other magnetic rods (e.g., magnetic tools), several advantages can be observed when compared to devices and pharmaceutical compositions currently on the market. First, the ability to combine the magnetic gradient with the magnetic field in an advantageous way that allows for magnetic rotors to be controlled from a distance, as opposed to catheters and cannulae which may cause unintended injury to a patient. Second, the ability to construct a compact mechanism that allows for the magnetic field to be changed in time in a simple and precise way, as well as possibly optimized, so that control is enabled over the wireless rotors, is a significant enhancement in view of pharmaceutical compositions that are hard to precisely control in vivo at normal dosages.

In addition, in one embodiment, when the magnetic rotors comprise magnetic nanoparticles, such as magnetite or another ferromagnetic mineral or iron oxide, the rotors can be manipulated in a way that improves mixing of a chemical or pharmaceutical agent that is in the vicinity of the magnetic nanoparticles. The use of the magnetic gradient combined with a time-varying magnetic field allows for flow patterns to be created which then amplifies the interaction of the chemical or pharmaceutical. This mechanism has been observed in animal models for the destruction of clots within the endovascular system using tPA as a thrombolytic. The pharmaceutical compositions can also be attached to the magnetic nanoparticles to perform the same function. As a result, less of those agents may be used for patient treatment provided that the nanoparticles are able to be navigated to and interact with the desired targets using the magnetic gradient and the time-varying magnetic field of the system.

In one embodiment, the magnetomotive system can make use of an easy-to-understand user-interface which allows the user to control the rotation plane of the magnetic field in a way that is not presently found. In some embodiments, the user interface comprises a touchscreen display. Furthermore, imaging technologies can be incorporated into or used in combination with the user interface such that an operator can have real-time feedback of the position of the magnetic nanoparticles, allowing for dynamic control and navigation. This can aid the operator to take steps to increase the effectiveness of the process, for example, by introducing more nanoparticles or more chemical agents. Images of the patient and/or regions of interest can be incorporated into a user face to aid an operator, physician, technician, or the like to plan a navigation route for the magnetic nanoparticles. Planning a navigation route can comprise identifying a therapeutic target, such as a clot, choosing a practical injection site for the nanoparticles, and planning a route through the patient's vasculature to arrive at the targeted object. During the actual navigation of the magnetic nanoparticles, the operator can use the original images used to plan the navigation or the user interface can receive updated images to show the operator, thus providing real-time imaging and feedback to the operator. The real-time user-interface can be coupled with a single-axis or multi-axis robotic arm to allow the operator to substantially continuously control the direction of nanoparticle infusion in real-time.

As an example, the real-time user interface can incorporate image information from an imaging system. The imaging system can be a system incorporating one or more imaging modalities, configured to provide imaging data to the magnetomotive system. The imaging data can be derived from x-ray data, PET data, MR data, CT scan data, ultrasonic imaging data, or other imaging modality data. In some embodiments, the magnetic nanoparticles act as contrast agents in conjunction with an imaging modality.

The magnetomotive system, in one embodiment, receives imaging data from the imaging system. In some embodiments, the imaging data comprises information derived from an imaging modality that, in use, provides information about vasculature of a subject, relative position of magnetic nanoparticles, fluid flow, fluid obstructions, or any combination of these. For example, the imaging system can produce image data based on ultrasound-based imaging. The imaging system can transmit sound waves aimed at an area of interest and interpret the echoed waves to produce an image. The ultrasound-based imaging system can be configured to provide imaging data in real-time and can be configured to identify fluid flow, tissue, liquid, magnetic nanoparticles, and the like. In some embodiments, ultrasound-based imaging is based on Doppler imaging which provides information about fluid flow. The ultrasound imaging system can image using frequencies from 1 and 18 MHz. The ultrasound images generated by the ultrasound-based imaging system are two-dimensional, three-dimensional, or four-dimensional images.

The magnetomotive system, in one embodiment, registers a reference frame of the magnetomotive system to a reference frame of the imaging system such that the imaging data from the imaging system is mapped to positions relative to the magnetomotive system. In some embodiments, registering the reference frames includes identifying elements of a received image and mapping those elements to positions within a subject. In some embodiments, registering the reference frames includes receiving information about the image system itself such as a physical orientation of an imaging device relative to a subject, depth of scan or image, field of view, and the like such that the magnetomotive system can map the received image relative to a coordinate system of the magnetic system. For example, an ultrasonic imaging system can send information to the magnetomotive system about the frequencies transmitted into the targeted area, the orientation of the imaging system relative to the subject, the position of the imaging system relative to the patient, or any combination of these. As another example, a CT system can include information about the depth of scan of an image, the field of view, the orientation of the system relative to the patient, and the like.

In one embodiment, the magnetomotive system identifies the magnetic nanoparticles within the imaging data received from the imaging system to track the particles, to navigate the particles, to switch between control modes (e.g. collection mode, vortexing mode, navigation mode, etc.), to monitor drug diffusion, or any combination of these. Identifying the magnetic nanoparticles can include analyzing the imaging data for signals associated with magnetic nanoparticles. For example, in ultrasonic imaging the magnetic nanoparticles can have a distinctive signal in an image due to their motion, composition, position, behavior, orientation, or any combination of these. As another example, in PET systems the magnetic nanoparticles can have a distinctive and/or identifiable signal in an image based on attached contrast agents, the density or composition of the nanoparticles, the position of the nanoparticles, or the like.

The magnetomotive system can determine a position of the magnetic nanoparticles relative to the magnetomotive system, based on the registration of the reference frames. The magnetomotive system can plan a navigation path from the identified position of the magnetic nanoparticles to a desired location within the subject based on the imaging data from the imaging system. For example, the navigation path can include an acceptable path through the vasculature of the subject from the current location of the magnetic nanoparticles to the targeted structure, such as an occlusion. In some embodiments, planning a navigation path comprises identifying a therapeutic target, such as a clot, choosing a practical injection site for the nanoparticles, and planning a route through the patient's vasculature to arrive at the therapeutic target.

The magnetomotive system can manipulate a magnetic field produced by the magnetic system to navigate the magnetic nanoparticles according to the navigation path. In some embodiments, manipulation of the magnetic field causes the magnetic nanoparticles present within the vasculature to agglomerate into a plurality of magnetic nanoparticle rods and causes the magnetic nanoparticle rods to travel through fluid within the vasculature by repeatedly walking end over end away from the magnetic field in response to rotation of the magnetic nanoparticle rods and the magnetic gradient and (b) flowing back through the fluid towards the magnetic field in response to the rotation of the magnetic nanoparticle rods and the magnetic gradient. In certain embodiments, the circulating motion of the magnetic nanoparticles increases exposure of a targeted structure (e.g. a fluid obstruction) within a blood vessel of the vasculature to a therapeutic agent (e.g. a thrombolytic drug) present in the blood vessel and accelerates action of the therapeutic agent (e.g. the thrombolytic drug on the fluid obstruction).

The magnetomotive system can also be used to move nanoparticles within small channels in a manner superior to approaches attempted with non-varying magnetic fields. The combined use of the magnetic gradient with a time-varying magnetic field allows for the nanoparticles to travel into small vessels, at which point therapy can be directed.

EXAMPLES

Aspects of the disclosure may be further understood in light of the following examples of illustrative embodiments of methods and systems, which should not be construed as limiting the scope of the disclosure or claims in any way. Moreover, the methods and procedures described in the following examples, and in the above disclosure, need not be performed in the sequence presented

Example 1

Administration of Magnetic Nanoparticles to Rabbits

Anesthetized rabbits were used to create an endovascular obstruction model by using the jugular veins and generating a clot at this location using thrombin, a natural product that produces blood clots. Once a stable clot was established, tPA (an enzyme commonly used to dissolve clots in endovascular obstruction patients), and magnetic nanoparticles were directed to the clot location and the length of time to dissolve the clot was recorded. See FIG. 38. After varying time points, the animals were euthanized, the remaining clots were weighed and analyzed and tissues were collected to ensure that there was no damage to the vessel itself.

The endovascular obstruction model allows the determination whether the magnetomotive stator system can re-open a vein or artery faster than with tPA alone, and if the dosage of tPA can be reduced without causing damage to the vein. The data gathered from the present endovascular obstruction studies clearly show that the magnetomotive stator system significantly speeds up the "clot-busting" activity of tPA.

Detailed Protocol

Summary: Deep Vein Thrombosis is a common and potentially deadly condition, and current treatment options can do more harm than good in some cases. Our aim is to use a non-survival anesthetized rabbit model of venous thrombosis to determine whether we can substantially increase the efficiency of current pharmacological treatment by manipulating commonly used MRI contrast media magnetically (Magnetic particles in imaging: D. Pouliquen et. al., Iron Oxide Nanoparticles for use as an MRI contrast agent: Pharmacokinetics and metabolism; Magnetic Resonance Imaging Vol. 9, pp. 275-283, 1991, the disclosures of which are hereby expressly incorporated by reference herein).

Magnetics: The iron nanoparticles described above are currently used in humans and considered safe.

Introduction: Deep Vein thrombosis (DVT) can be asymptomatic, but in many cases the affected area is painful, swollen, red and engorged with superficial veins. Left untreated, complications can include tissue necrosis and loss of function in the affected limb. A serious complication is that the clot could dislodge and travel to the lungs resulting in a pulmonary embolism (PE) and death. Current treatment of DVT includes high doses of lytic enzymes such as streptokinase and tissue plasminogen activator (tPA), sometimes augmented with mechanical extraction (Angiojet, Trellis Infusion System). The doses of lytic enzymes are such that in many patients (particularly elderly) the risk of hemorrhage is high and poor outcomes common (A review of antithrombotics: Leadley R J Jr, Chi L, Rebello S S, Gagnon A. J Pharmacol Toxicol Methods; Contribution of in vivo models of thrombosis to the discovery and development of novel antithrombotic agents. 2000 March-April; 43(2):101-16; A review of potential tPA complications: Hemorrhagic complications associated with the use of intravenous tissue plasminogen activator in treatment of acute myocardial infarction, The American Journal of Medicine, Volume 85, Issue 3, Pages 353-359 R. Califf, E. Topol, B. George, J. Boswick, C. Abbottsmith, K. Sigmon, R. Candela, R. Masek, D. Kereiakes, W. O'Neill, et al., the disclosures of which are hereby expressly incorporated by reference herein). The aim of the present DVT model is to allow determination whether the magnetomotive stator system enhances the activity of tPA at the site of the thrombus such that a significantly lower dose of tPA can be used, greatly reducing the risk of hemorrhage. Further, current mechanical thrombolytics are known to damage endothelium. Following each experiment, the vessel segment is evaluated histologically for endothelial integrity.

Procedure: This is a non-survival procedure. New Zealand White rabbits (1.5-2.5 kg) are anesthetized using Ketamine 35 mg/kg, Xylazine 5 mg/kg IM and the ventral neck shaved and prepared for surgery. Mask induction using isoflurane gas may be used to deepen the anesthetic plane to allow for orotracheal intubation. In one embodiment, once intubated, the animal is moved to the operating room and administered isoflurane gas anesthesia (1-5%, to surgical effect) for the duration of the procedure. Heart rate, respiratory rate, body temperature and end-tidal $CO_2$ are monitored while the animal is under anesthesia. In an effort to reduce the number of animals and reduce the variability among studies, bilateral 10-12 cm incisions are made paramedian to the trachea and sharp/blunt dissection is used to isolate the jugular veins. If no significant complications arise, the total number of animals is reduced accordingly.

An ultrasonic flow probe is placed on the distal portion of the isolated vessel and baseline blood flow data is collected for 30 minutes. Following stabilization of venous flow, silk (or other braided, uncoated) suture (5 or 6-0, taper needle) is passed transversely through the center of the vessel lumen at the distal aspect of the area to be occluded, and secured with a loose knot. The function of this suture is to act as an anchor for the clot and prevent embolism. Then, a ligature is placed on the proximal and distal portion of the vessel (proximal in relation to the flow probe) to occlude flow. Ultimately a 2 or 3 cm segment of the vessel is isolated with ligatures. 100-200 U bovine thrombin is administered intravenously (27-30 g needle) into the space approximately 1 mm proximal the first ligature. The proximal ligature is placed immediately following withdrawal of the thrombin needle. The entry site of the needle is closed with a small drop of Vetbond® to prevent bleeding during the lysis procedure. The clot is allowed to mature and stabilize for 30 minutes at which time the ligatures are removed and tPA or a combination of tPA with magnetic nanoparticles (described above) are injected at the antegrade aspect of the vein (27-30 g needle, entry hole again sealed with Vetbond®). A dynamic magnetic field is applied to the location and dissolution of the clot is monitored continuously for up to 3 hours via ultrasonic flowmetry. Following re-establishment of flow the animals are euthanized while still under anesthesia with an i.v. overdose of pentobarbital (150 mpk). The experimental vessel segment and residual clot is then collected, weighed and fixed for further analysis. Dosages of tPA used in the endovascular obstruction model range from about 312.5 U to about 5000 U.

Groups: The study is accomplished in 2 phases, Pilot and Proof of Concept. Both phases include the procedures outlined here, but the Pilot Phase utilizes only the left jugular, leaving the other a naïve histological comparator.

Pilot Groups

1. Thrombin only, no tPA. This group will establish the baseline mass of our thrombus and allow assessment of thrombus stability. n=30.

2. tPA only, dose ranging to establish a fully efficacious dose (100% re-cannulation) n=6×3 doses=18

3. tPA only, dose ranging to establish a sub-optimal dose (either 100% effective in 25-50% of subjects, or re-cannulation in all subjects but only 25-50% of flow rate). tPA is notoriously variable, so the sub-optimal dose may be difficult to find. n=3×4 doses=12

Device alone to establish optimum particle concentration n=3×3 concentrations=9.

Proof of Concept Groups:

Note: "n" numbers may be combined with pilot data depending on initial data quality, further reducing animal requirements.

1. Optimal tPA. n=6
2. Sub-optimal tPA. n=6
3. Device alone. n=6
4. Device+Optimal tPA. n=6
5. Device+sub-optimal tPA. n=6

Two questions can be answered using the present endovascular obstruction model:

Small Vessels: Following the completion of the thrombosis procedure in the jugular veins, the surgical plane of anesthesia is continued and a laparotomy performed. A portion of the bowel is exteriorized and bathed in saline to prevent drying. One of the large veins in the mesentery is tied off and cannulated with PE10. A mixture of iron particles and fluoroscene (12.5 mg/ml in 100 ul) is injected and photographed under black light. This allows the determination whether the fluoroscene diffuses into the very small veins surrounding the bowel, and illustrate that the magnetomotive stator system directs magnetic nanoparticles to the small vasculature.

Safety: Is damage done to the endothelial lining using the magnetomotive stator system? Does it create hemolysis? The present endovascular obstruction model allows a determination via review of the vena cava. Following the completion of the thrombosis procedure in the jugular veins, the surgical plane of anesthesia is continued and a laparotomy performed.

A 5-6 cm segment of the vena cava is isolated and all branches tied off. The vessel is tied off and cannulated with PE10. Either iron nanoparticles (12.5 mg/ml in 100 μl) or saline (100 μl) is injected and the vessel and is magnetically controlled for 3 hours. At the end of 3 hours the blood is removed from the vessel segment via venapuncture and sent for assessment of hemolysis, following euthanasia the vessel segment is explanted for histological evaluation of the endothelium. Three experiments are performed with particles and three without.

Arterial Access

Figure 37A:
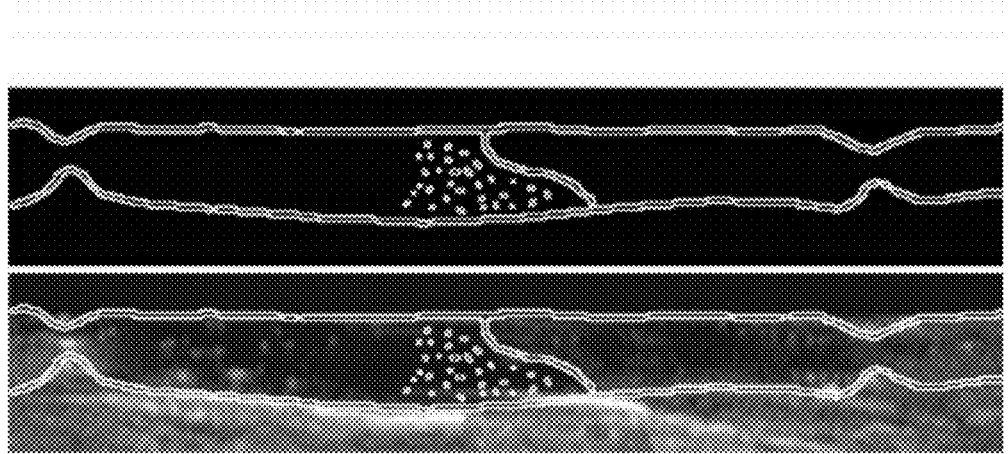
FIGS. 37A and 37B illustrate the clearance of a thrombosis in the vein of a rabbit using embodiments of the magnetomotive stator system and magnetic nanoparticles.
Figure 37B:
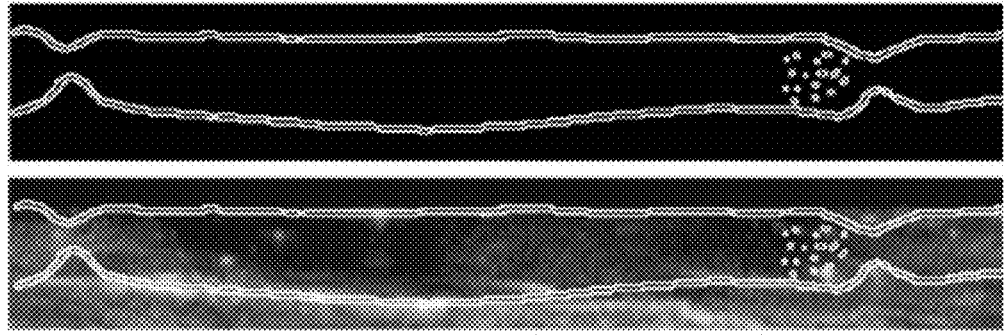

Using the DVT model described above, it has been demonstrated that the magnetomotive stator system significantly enhances tPA efficacy in this rabbit model. See FIGS. 37A and 37B. Tissues have been gathered that were evaluated histologically. There is no damage observed to tissue when examined histologically.

Example 2

IV-Administered Nanoparticles can be Collected in an In Vivo Ligated Rabbit Femoral Artery New Zealand White rabbits were used as in Example 1, except the femoral artery was used. Through a 3-4 cm incision in the lower abdomen, the left femoral artery was isolated from the iliac bifurcation to the abdominal wall, and all branches were tied off. Blood flow in the artery and the abdominal aorta were monitored continuously with a Transonics Doppler flow probe coupled to a Transonics T206 meter.

In this example, an acute, anesthetized rabbit model of arterial occlusion was used in which the right femoral artery was isolated and ligated to simulate an occlusive thrombus and create a static blood pool. Magnetic nanoparticles (200 mg/kg) were infused intravenously over 15 minutes and collected with the magnet system. The presence of a significant mass of nanoparticles at the ligation was confirmed for each animal.

Example 3

Figure 38:
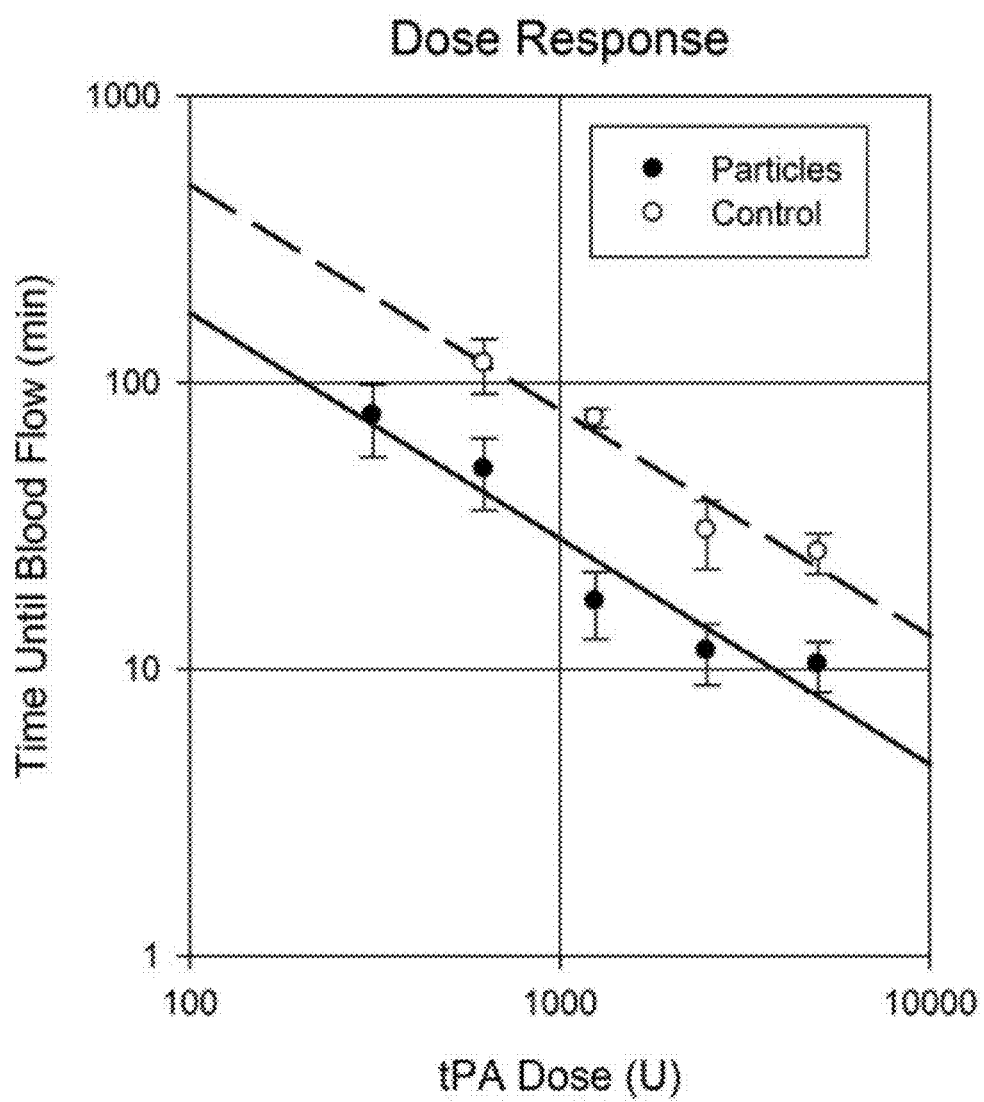
FIG. 38 illustrates the dosage response curve of tPA using embodiments of the magnetomotive stator system showing both reduced time to increase blood flow in a rabbit, and reduced amount of tPA required to produce the same result, in accordance with an embodiment of the invention.

The Action of Pulling IV-Administered Nanoparticles Out of the Stream can Concentrate a Drug Faster than Diffusion Alone Evans Blue dye (50 mg) was infused alone over 15 minutes and co-infused with magnetic nanoparticles in the presence of the magnet system, using the rabbit model of Example 2. The advancement of the dye in the occluded artery was captured and quantified by image analysis. The results demonstrated that diffusion alone quickly diminished, achieving 35% penetration of a ligated vessel an hour after administration. Full diffusion was accomplished in 25 minutes using magnetic nanoparticles, whereas full diffusion was not possible with the dye alone. The rate of diffusion remained strongly linear for the magnetic nanoparticles, with a volume penetration rate of 4% per minute, as shown in the graph in FIG. 38. FIG. 38 illustrates a graph of the exhausted diffusion of Evan's blue dye alone versus complete diffusion using magnetic nanoparticles.

Example 4

Figure 39:
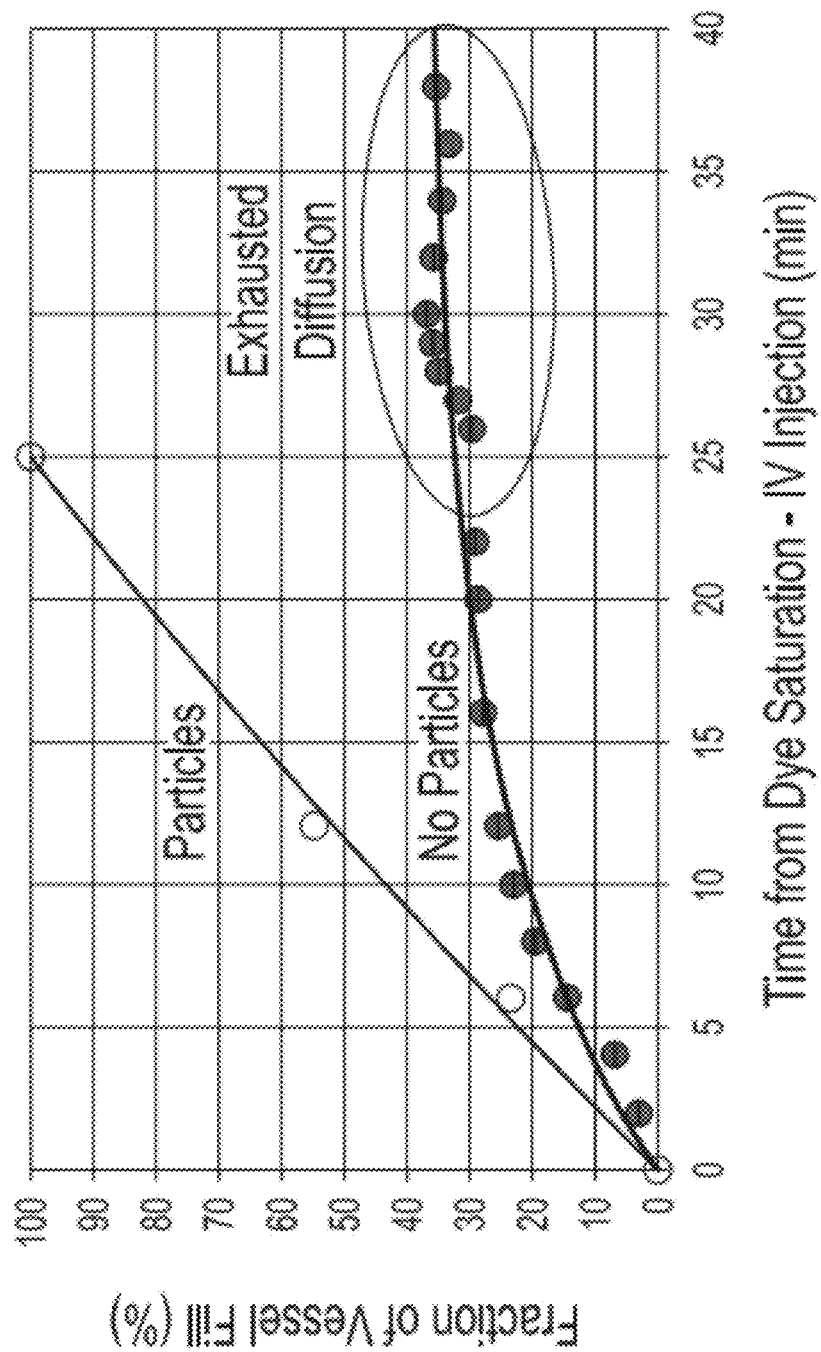
FIG. 39 illustrates results of testing showing that concentrating a drug using magnetic nanoparticles is faster than diffusion alone.

Magnetic Mixing of tPA and Magnetic Nanoparticles at a Clot's Surface Results in Faster Thrombolysis than tPA Alone This example used an acute anesthetized rabbit model with a thrombin-induced occlusive thrombus in the jugular vein. In the example, tPA alone and tPA co-administered with magnetic nanoparticles (1.2 mg) were injected locally and the time to re-canalize the vessel was measured and confirmed by a Doppler flow meter. The tPA dose was taken from a published source and ranged from 312 U to 5000 U, with 2500 U being the standard dose. The results demonstrated 3× faster time to re-canalize with the magnet system versus tPA alone, as shown in FIG. 39. Similar lysis rates were demonstrated for a 0.25×tPA dose.

Example 5

Faster Thrombolysis Results when Magnetic Nanoparticles are Intravenously Co-Administered with a Thrombolytic Versus the Thrombolytic Alone A common technique for forming clots in arteries was implemented. The clot was formed near the abdominal wall (approx. 3 cm from the iliac bifurcation) by first, crushing the area to be occluded with guarded hemostats to disrupt the intima (2-3 mm segment of artery) exposing collagen, tissue factor and other pro-thrombotics from the arterial wall, then applying critical stenosis to the crushed area using 5-0 silk suture tied with a castration knot, such that flow was reduced to approximately 25% of the baseline flow velocity (approximately 90% reduction in lumen area). Following 3-5 closure/re-open cycles, an occlusive clot formed in 30-60 minutes. The clot was considered occlusive by the absence of measurable blood flow for 30 minutes.

With the magnet placed above the clot and rotating at 300 rpm, magnetite nanoparticles (600 mg) were co-infused with streptokinase (30,000 U) in 20 ml saline over 15 minutes (2000 U/min, 80 ml/hr), followed by streptokinase alone at 575 U/min (7.3 ml/hr). Control animals received the same streptokinase infusion without the magnet placement or magnetic nanoparticles.

Figure 40:
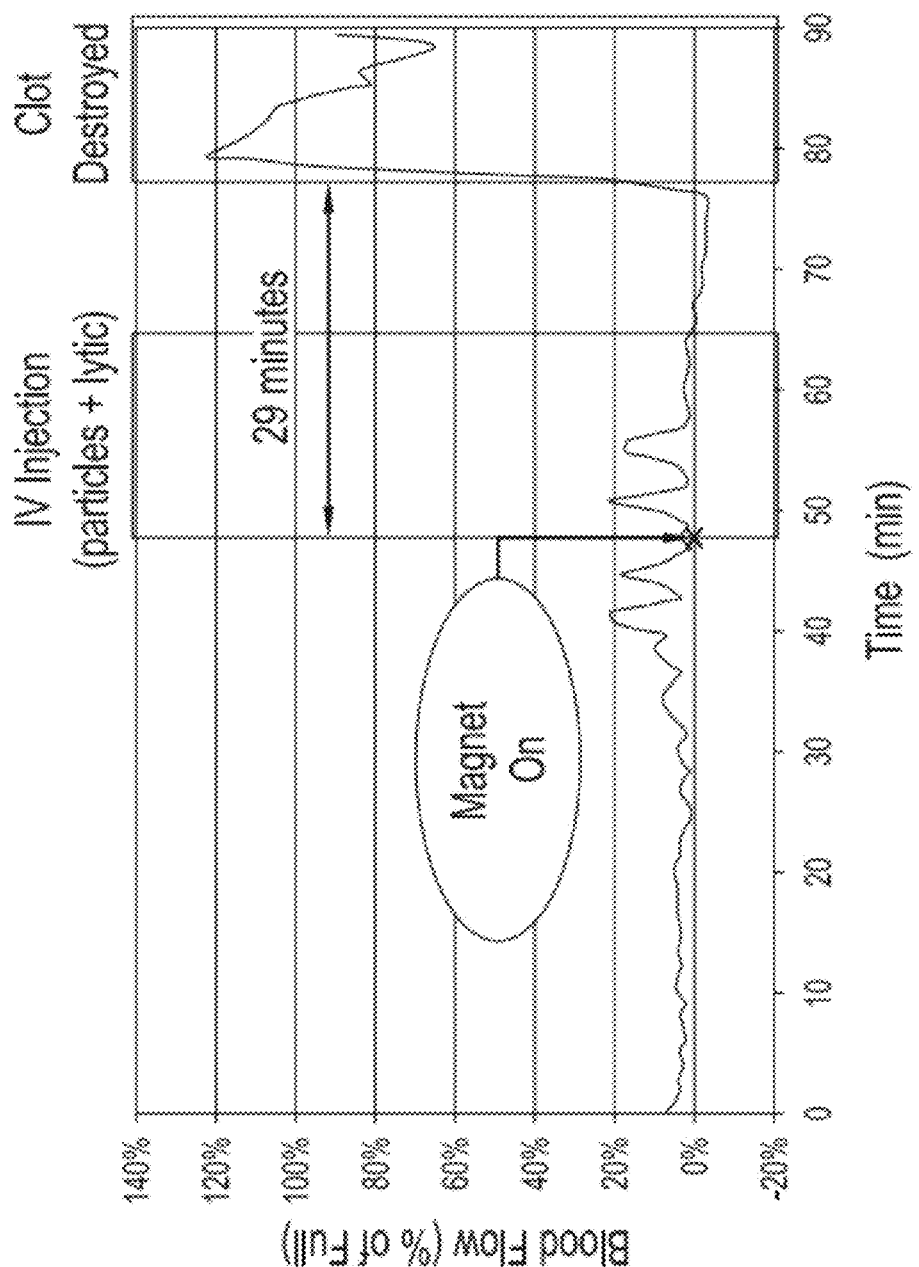
FIG. 40 illustrates a graph of blood flow as a function of time for an example of magnetic nanoparticle-accelerated clot lysis.

The vessel was considered open when flow reached 50% of the pre-occlusion stenosed value (2-2.5 ml/min) In many cases, small excursions in flow to 0.3-0.5 were seen during the nanoparticle treatment while the magnet was activated, but not during treatment with streptokinase alone. The 4 treated arteries opened at 29.5, 13.4, 32 and 28 minutes following the beginning of treatment. The controls were allowed 2 hours and 1 hour respectively with no measurable flow restoration. Interestingly, after the 1 hour streptokinase control study, nanoparticles and streptokinase were co-administered and the magnet activated, resulting in the vessel opening after 29 min. For the co-administration of streptokinase and nanoparticles, the mean time for clot lysis was 26.4 min with a standard deviation of 7.4 min, and a standard error of 3.3 min Example data from the Doppler flow-probe is shown in FIG. 40 illustrating magnetic nanoparticle-accelerated clot lysis.

Example 6

Confirmation of In Vivo Clot Lysis Ultrasound Visibility

The ability to visualize the nanoparticles under Doppler ultrasound imaging offers limited value for stroke therapies. However, for deep-vein thrombosis applications, such a feature would allow procedures to be performed in procedure rooms, thus not incurring the costs associated with an x-ray suite. Because the magnetic nanoparticles create flow patterns in the blood, it is possible to visualize blood flow using Doppler imaging, even if the nanoparticles themselves could not be observed. The study demonstrated that complete in vivo clot lysis was highly visible under Doppler ultrasound imaging.

Using a rabbit, a midline incision (15 cm) of the vena cava was isolated from the right renal vein to the iliac bifurcation and all branches ligated. A PE10 catheter with a flame-flared tip was introduced via the left femoral vein and advanced past the bifurcation. A ligature (4-0 silk) was placed around the vena cava at the bifurcation and the catheter retracted until the ligature trapped the flared tip. The proximal aspect of the vena cava was then ligated immediately distal from the right renal vein creating an isolated, blood-filled segment approximately 8-9 cm long. A thrombus was formed at the proximal end of the segment by clamping (atraumatic vascular clamp) 1.5 cm distal the proximal ligation and injecting 50 U of thrombin (30 µl) via venapuncture (30 g). The needle was slowly withdrawn and the puncture site sealed with a drop of tissue adhesive. The clot was allowed to mature for 30 minutes prior to clamp removal. 12 mg of nanoparticles and 5000 U of tPA were then injected (200 µl) via the femoral catheter and the magnet started. The thrombolysis was recorded with Doppler Ultrasound (Sonosite Turbo M). Complete clot lysis occurred in 11 minutes and was highly visible under Doppler ultrasound imaging.

Example 7

In Vitro Studies: Confirmation of 2D Magnetic Nanoparticle Control

As an extension to the previous examples, a bifurcated glass phantom was obtained to investigate the ability to control the direction of the nanoparticles in two dimensions. The parent vessel is 1 mm wide with 0.5 mm bifurcations. Control of the nanoparticles is depicted in FIG. 41. In (a)-(b), the nanoparticle collection is split between the bifurcations. In segment (c), the nanoparticles are retracted. In segment (d) the nanoparticles are directed down the lower branch before being again retracted in (e). The nanoparticles are directed along the upward branch in (f).

Investigations were carried out to quantify the relationship between the lytic-agent dose and the lysis rate. Two lytic agents were used in these studies: streptokinase and tPA. The clot recipes are summarized below.

Streptokinase Clot Recipe

The clot model used for the streptokinase dissolution test was a bovine fibrinogen/human plasminogen hybrid with clotting initiated with human thrombin. Bovine fibrinogen from Sigma (F8630) was dissolved into a 197 mM Borate buffer solution made with Sigma components (B0252, B9876, S9625). The ratio of this solution was 0.9 grams of fibrinogen to 10 ml of buffer solution. The lyophilized plasminogen and thrombin powders were dissolved using the buffer solution. The Human plasminogen from EMD Chemicals (528175-120 units) was dissolved in 600 µl of buffer to create a 0.2 units/µl solution. The Human thrombin from Sigma (T6884-1K units) was dissolved in 5 ml of buffer to create a 200 units/ml solution. Additionally, a gelatin solution was created using 100 ml of a 100 mM Potassium phosphate solution using Sigma (P5379) and de-ionized water. To this was added 0.5 grams of porcine gelatin (Sigma G2500), 0.1 grams Sodium chloride (Sigma S9625), and 0.01 grams Thimerosal (Sigma T5125). To create the clot samples, 608 µl of fibrinogen solution, 252 µl of borate buffer, 81 µl of gelatin solution and 10.2 µl of plasminogen solution were combined in a mixing vial and gently swirled for 15 seconds. The mixture was then separated into four 230 µl batches to which 5 µl of thrombin solution was added into each batch. The combination was again gently swirled to mix and 100 µl of solution and was decanted into culture tubes and incubated at 37° C. for 4 minutes to promote clotting. The dissolving solution contained the dosages in phosphate buffered saline that had been augmented with Red #40 dye in borate buffer. (0.02 g Red #40 from CK Products dissolved in 1 ml borate buffer.) A standard dose of plasminogen was 8 µl of solution, a standard dose of magnetic nanoparticles was 6 µl of $Fe_3O_4$ (Cathay Pigments 1106), and a standard dose of streptokinase was 12 µl of solution (Sigma S8026 of 10 units/µl of phosphate buffered saline). Volumetric balance of fractional doses was made up with borate buffer solution.

Example tPA Clot Recipe

The clot model used for the tPA dissolution test was composed of human fibrinogen and human plasminogen with clotting initiated with bovine thrombin. Human fibrinogen from EMD Chemicals (341576) was dissolved into a 197 mM Borate buffer solution made with Sigma components (B0252, B9876, S9625). The ratio of this solution was 1 gram of fibrinogen to 11.1 ml of buffer solution. The lyophilized plasminogen and thrombin powders were dissolved using the buffer solution. Human plasminogen from EMD Chemicals (528175-120 units) was dissolved in 120 µl of buffer to create a 1 unit/µl solution. Bovine thrombin from Sigma (T6200-1K units) was dissolved in 100 µl of buffer to create a 10 units/µl solution. A gelatin solution was created using 100 ml of a 100 mM Potassium phosphate solution using Sigma (P5379) and de-ionized water. To this was added 0.5 grams of porcine gelatin (Sigma G2500), 0.1 grams Sodium chloride (Sigma S9625), and 0.01 grams Thimerosal (Sigma T5125). A solution with tantalum nanoparticles was made to add visual contrast to the clot. This was composed of 0.0231 g of Ta powder (AP Materials 010111) in 1 ml of de-ionized water. To create the clot samples, 100 µl of fibrinogen solution, 125 µl of borate buffer, 32 µl of gelatin solution, 25 µl of tantalum nanoparticles solution and 3 µl of plasminogen solution were combined in a mixing vial and gently swirled for 15 seconds. To the mixture, 5 µl of thrombin solution was added and the combination gently swirled to mix. 100 µl of solution was decanted into each of two culture tubes and incubated at 37° C. for 4 minutes to promote clotting. The dissolving solution contained the dosages in phosphate buffered saline. A standard dose of plasminogen was 3 µl of solution, a standard dose of magnetic nanoparticles was 12 µl of $Fe_3O_4$ (Cathay Pigments 1106), and a standard dose of tPA was 32 µl of solution (EMD Chemicals 612200 of 78.125 units/µl of phosphate buffered saline). Volumetric balance of fractional doses was made up with borate buffer solution.

Figure 42:
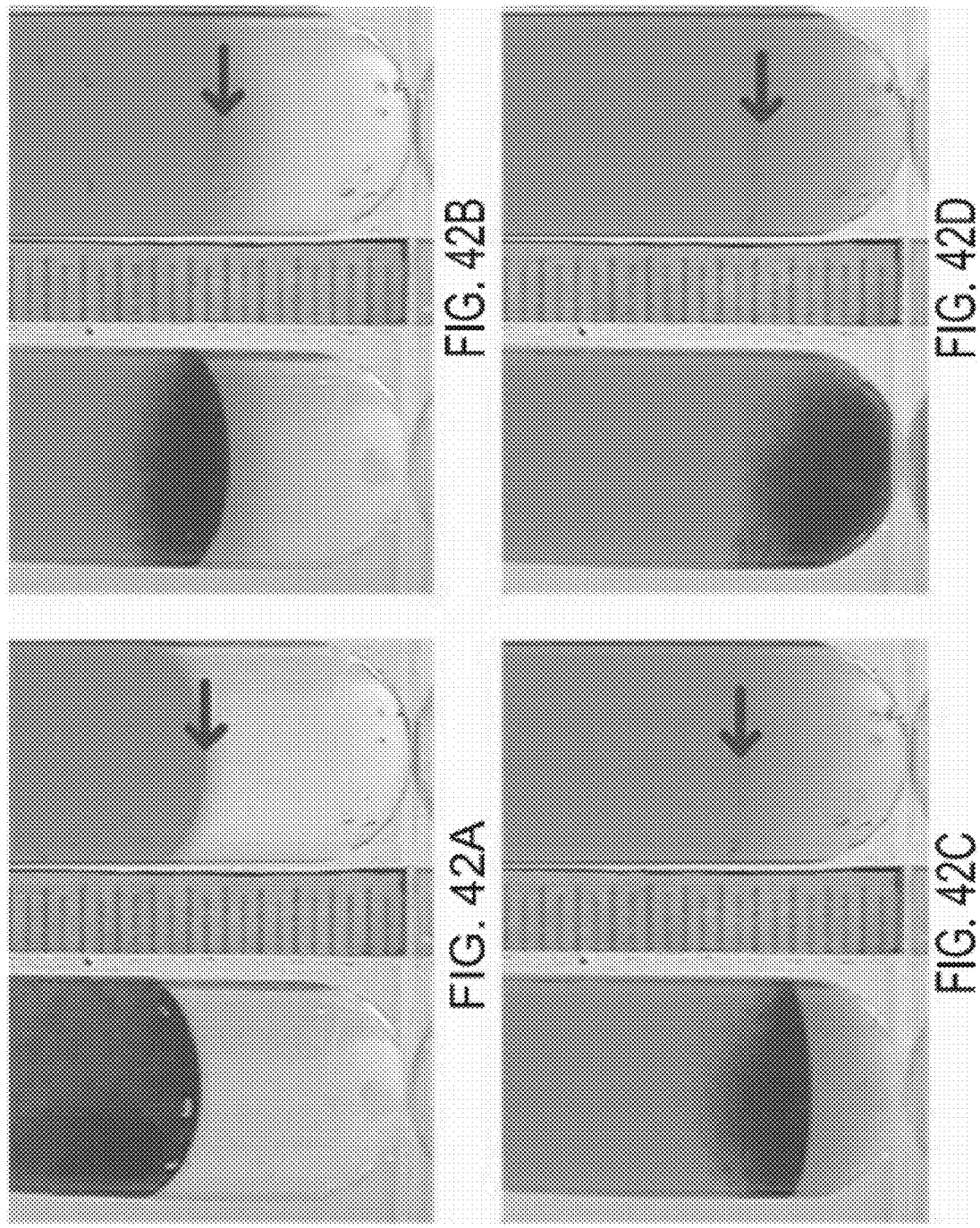
FIG. 42 illustrates an example of lysis of biological thrombus using streptokinase and magnetic nanoparticles.
Figure 43:
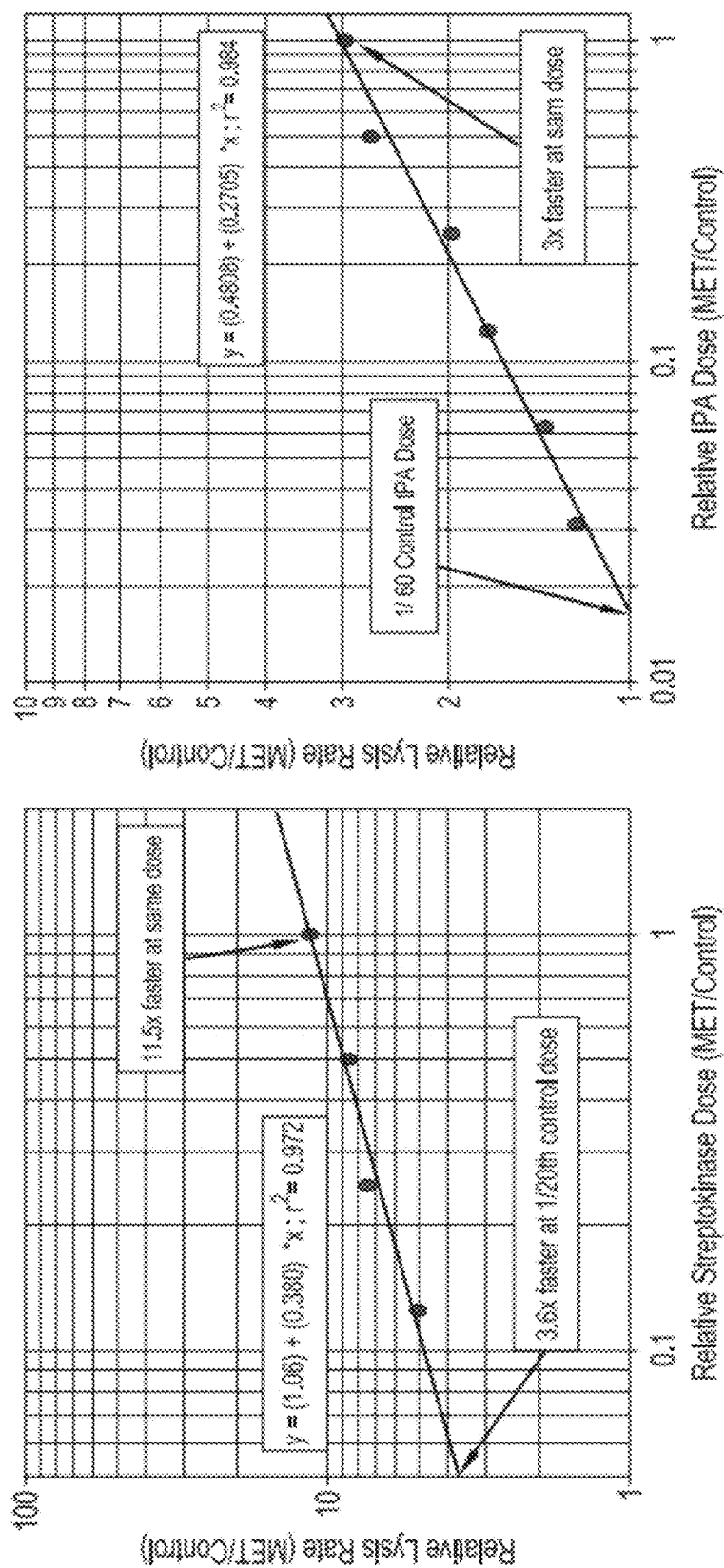
FIG. 43 illustrates graphs of streptokinase and tPA dose response improvements.

FIG. 42 depicts the test-tube model used to quantify the lysis rate using both streptokinase and tPA. In the figure, the MET sample is on the left with the magnetic nanoparticles indicated in black. The control sample is on the right with the arrow indicating the meniscus. Both samples use a full dose of streptokinase. The test tubes measure about 5 mm in width and the ruler is subdivided into 0.5 mm tick marks. The artificial thrombus was intentionally constructed to be dense in order to slow down the lysis rate. These relatively slow models made tracking the fall of the meniscus easier for both the MET and control samples and resulted in better wall adhesion. For streptokinase, typical total MET lysis times using streptokinase were under about 7 hrs. For tPA, MET lysis rates were under about 4 hrs. Models in which lysis occurred in less than 1 hr resulted in clot fragmentation that made quantification of the rate of lysis problematic. FIG. 43 depicts the relative dose response improvement possible with MET using streptokinase and tPA, respectively. For a relative lytic-agent dose=1, MET results in lysis about 11.5 times faster for streptokinase and about 3 times faster for tPA (versus the control). Not captured in these plots is the result that when no lytic agent is used with MET, no lysis occurs. This suggests that there is a rapid fall-off at relative lytic doses less than about ⅛th for streptokinase and about ¹⁄₃₂nd for tPA. The linear fits suggest equivalent lysis rates at about ¹⁄₈₀th dose for streptokinase and about ¹⁄₆₀th dose for tPA. The above work was performed using about a 0.01 T field at about a 5 Hz frequency, and exploratory work using fields from about 0.01-0.03 T and frequencies from about 1-10 Hz have shown little impact on these results.

Example 8

Comparing Lysis Rates and Nanoparticle Dose

Figure 44:
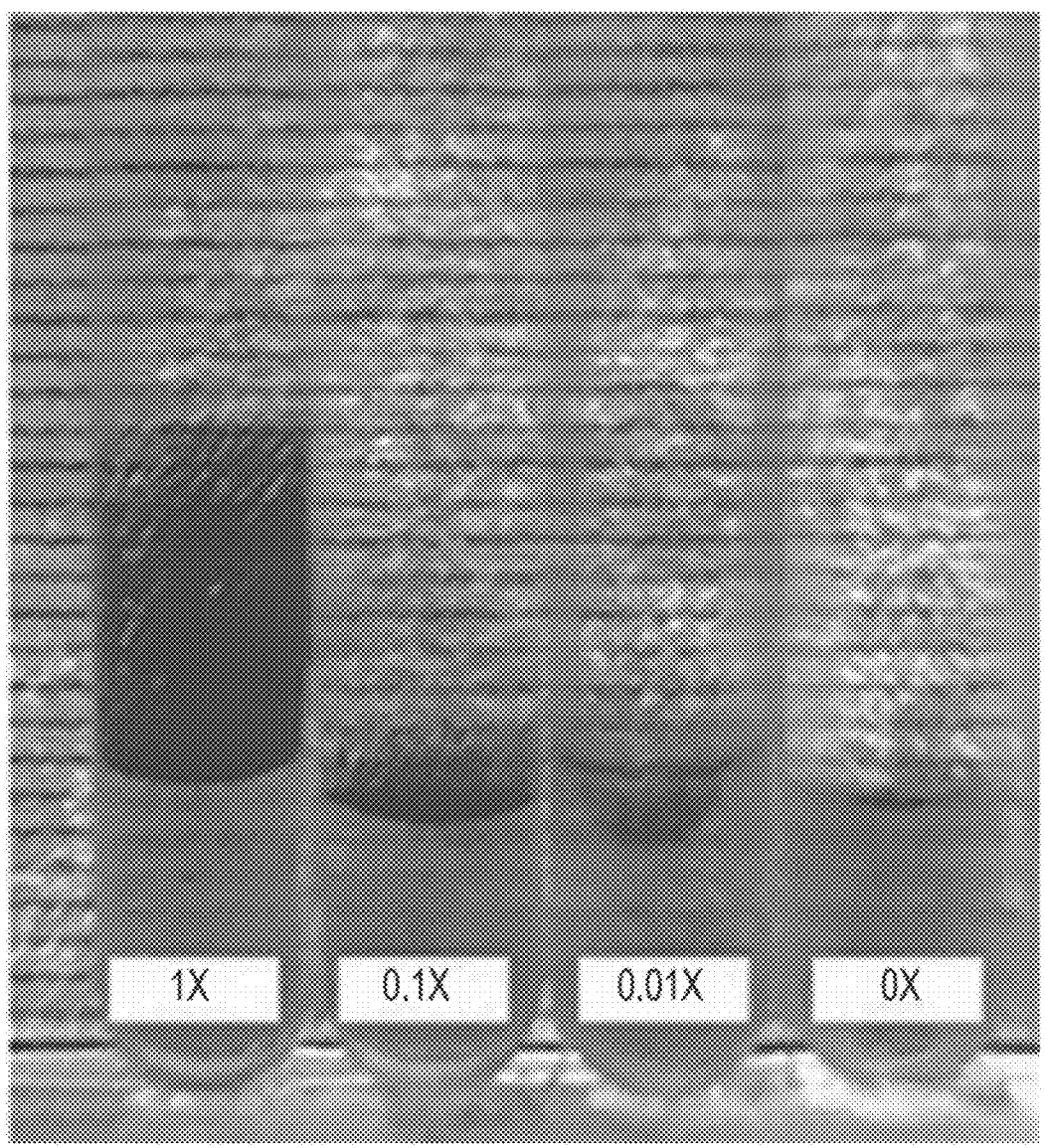
FIG. 44 illustrates an example test tube setup having defined tPA dose and relative magnetic nanoparticle dose.

An in vitro test tube study was performed to measure the effects of a magnetic nanoparticle dose with a common tPA dose. The clot recipe detailed in Example 7 was used in the model. FIG. 44 is a captured image of the test tube setup. In the figure, the tPA dose is common across all samples and the multipliers refer to the magnetic nanoparticle dose. In this study, the magnetic nanoparticle doses were exponentially reduced from the starting (1×) dose of 0.28 mg. Common to all samples is 625 U of tPA.

Not depicted are the effects of a 1× nanoparticle dose when no tPA is present, which resulted in no measurable lysis. This confirms that, in accordance with several embodiments, the technology described herein is pharmacomechanical in nature, and that the nanoparticles themselves may not generate measurable forces on the thrombus.

Figure 45:
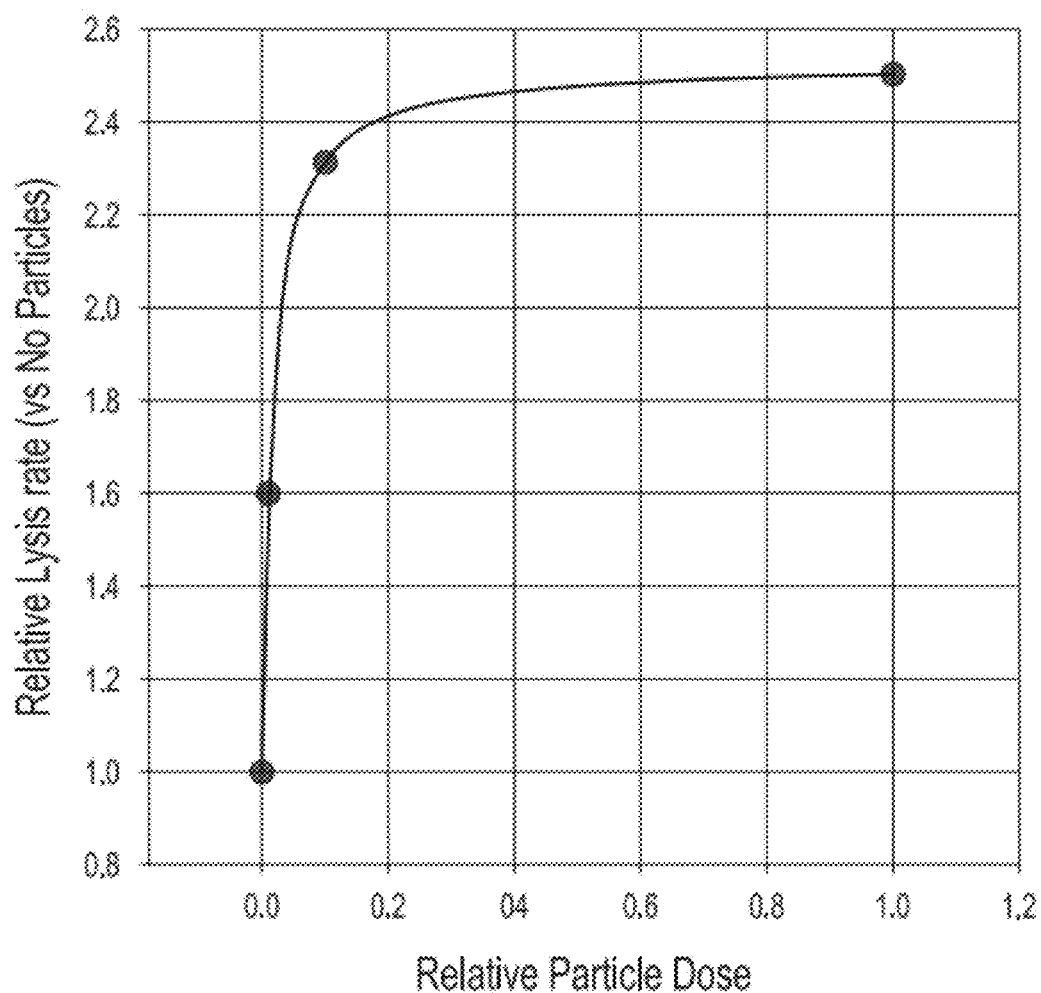
FIG. 45 illustrates a graph of lysis rate as a function of relative magnetic nanoparticle dose.

FIG. 45 depicts the change in the relative lysis rate for a change in the relative nanoparticle dose, where the 1× nanoparticle dose is the reference. Larger doses of nanoparticles can result in modest gains in the lysis rate (a 0.1× dose can reduce the rate by less than 8% as compared to the 1× dose). In some embodiments, the effectiveness of the nanoparticle dose is related to the clot's exposed surface area and/or a tPA dose. Once the surface is saturated, increasing the nanoparticle dose may offer little or no benefit. Once there are sufficient nanoparticles to create a macroscopic flow pattern, then more nanoparticles may not be as effective in building stronger fluidic currents.

Other Embodiments

The detailed description set-forth above is provided to aid those skilled in the art in practicing the systems and methods described herein. However, the systems and methods described and claimed herein are not to be limited in scope by the specific embodiments herein disclosed because these embodiments are intended as illustration of aspects of the systems and methods. Any equivalent embodiments are intended to be within the scope of this disclosure. Indeed, various modifications in addition to those shown and described herein will become apparent to those skilled in the art from the foregoing description which do not depart from the spirit or scope of the disclosure. Such modifications are also intended to fall within the scope of the appended claims.

What is claimed is:

1. A method of treating a thrombus within a blood vessel of the brain through external magnetomotive manipulation of magnetic nanoparticles, the method comprising:

introducing a thrombolytic drug within vasculature of a subject, the thrombolytic drug configured to have a therapeutic effect on a thrombus within a blood vessel of the brain;

introducing a plurality of coated magnetic nanoparticles within the vasculature of the subject, wherein the magnetic nanoparticles have a diameter between about 15 nm and 150 nm;

orienting a permanent magnet external to the blood vessel and having a magnetic field and a directed magnetic gradient to establish a magnetic rotation plane of the permanent magnet;

programming a controller to cause the permanent magnet to be positioned and to rotate in a manner sufficient to cause the magnetic nanoparticles to agglomerate to form a plurality of magnetic nanoparticle rods having a length between 0.1 and 2 millimeters within the vasculature to travel toward the thrombus in an end over end walking motion in response to torque exerted by the rotating magnetic field and to an attractive force of the directed magnetic gradient, wherein the rotational frequency of the rotating magnetic field is between 1 Hz and 30 Hz, wherein the rotating magnetic field has a magnitude of between 0.01 Tesla and 0.1 Tesla, wherein the directed magnetic gradient has a strength of between 0.01 Tesla/meter and 5 Tesla/meter, wherein the end over end walking motion of each of the magnetic nanoparticle rods generates a circulating fluid motion within the vasculature proximal to the thrombus, and wherein the circulating fluid motion facilitates contact of the thrombolytic drug with the thrombus by enhancing diffusion of the thrombolytic drug to the region of the blood vessel proximal to the thrombus and by refreshing contact of the thrombus with the thrombolytic drug, thereby providing more effective interaction of the thrombolytic drug with the thrombus.

2. The method of claim 1, wherein the thrombolytic drug is attached to the magnetic nanoparticles prior to introduction.

3. The method of claim 1, wherein the thrombolytic drug is introduced within the vasculature separate from the magnetic nanoparticles.

4. The method of claim 1, wherein the permanent magnet is rotatably coupled to a motor by a movable arm.

5. The method of claim 1, wherein said introducing a thrombolytic drug within vasculature of a subject comprises introducing a reduced dose of the thrombolytic drug than would be introduced if the magnetic nanoparticles were not introduced.

6. The method of claim 1, wherein said step of programming the controller comprises adjusting the rotational frequency of the rotating magnetic field, a plane of the rotating magnetic field with respect to the thrombus, and/or a distance of the rotating magnetic field with respect to the thrombus.

7. The method of claim 1, further comprising adjusting one or more of the position, the rotation plane and the rotation frequency of the magnetic field in response to at least one characteristic of the thrombus.

8. The method of claim 7, wherein the at least one characteristic is selected from the group consisting of: a location, a shape, a thickness, and a density of the thrombus.

9. The method of claim 7, wherein the at least one characteristic is determined from one or more images of the region of the blood vessel in which the thrombus is located.

10. The method of claim 1, wherein said orienting a permanent magnet having a magnetic field and a directed magnetic gradient to establish a magnetic rotation plane of the permanent magnet is performed based on preoperative images of the blood vessel.

11. A method of treating a thrombus within a blood vessel of a subject through external magnetomotive manipulation of magnetic nanoparticles, the method comprising:
introducing a thrombolytic agent within vasculature of a subject, the thrombolytic agent configured to facilitate lysis of a thrombus within a blood vessel;
administering a therapeutically effective amount of magnetic nanoparticles within the vasculature,
wherein the magnetic nanoparticles have a diameter between about 15 nm and 150 nm;
positioning a magnet external to the blood vessel and having a magnetic field and a directed magnetic gradient to establish a magnetic rotation plane of the magnet;
programming a controller to cause the magnet to be positioned and to rotate in a manner sufficient to cause the magnetic nanoparticles to agglomerate to form a plurality of magnetic nanoparticle rods having a length between 0.1 and 2 millimeters within the vasculature and to cause the magnetic nanoparticle rods to travel within the vasculature toward the thrombus within the blood vessel by individually walking end over end in response to the rotating magnetic field and the directed magnetic gradient of the magnet;
wherein the rotational frequency of the rotating magnetic field is between 1 Hz and 30 Hz,
wherein the rotating magnetic field has a magnitude of between 0.01 Tesla and 0.1 Tesla,
wherein the directed magnetic gradient has a strength of between 0.01 Tesla/meter and 5 Tesla/meter; and
adjusting a frequency of the rotating magnetic field, a plane of the rotating magnetic field with respect to the thrombus, and a distance of the rotating magnetic field with respect to the thrombus to cause the magnetic nanoparticle rods to generate a circulating fluid motion within the vasculature proximal to the thrombus,
wherein the circulating fluid motion facilitates contact of the thrombolytic agent with the thrombus by enhancing diffusion of the thrombolytic agent to the region of the blood vessel proximal to the thrombus and by refreshing contact of the thrombus with the thrombolytic agent, thereby providing more effective interaction of the thrombolytic agent with the thrombus.

12. The method of claim 11, wherein the thrombolytic agent is attached to the magnetic nanoparticles prior to introduction.

13. The method of claim 11, wherein the magnet is a permanent magnet rotatably coupled to a motor by a movable arm.

14. The method of claim 11, further comprising adjusting one or more of the position, the rotation plane and the rotation frequency of the magnetic field in response to one or more images of at least one of the region of the blood vessel in which the thrombus is located.

15. The method of claim 11, wherein said introducing a thrombolytic agent within vasculature of a subject is performed separately from administering the therapeutically effective amount of magnetic nanoparticles within the vasculature.

16. The method of claim 1 or 11, wherein the step of programming the controller is performed by a user via a touch screen display or a control button on a handheld device.

17. A method of treating a thrombus within a blood vessel of a subject through external magnetomotive manipulation of magnetic nanoparticles, the method comprising:
applying a magnetic field and a directed magnetic gradient of a magnet to a plurality of coated magnetic nanoparticles introduced within vasculature of a subject,
wherein the magnetic nanoparticles have a diameter between about 15 nm and 150 nm;
rotating the magnet at a first rotational frequency effective to agglomerate the magnetic nanoparticles into a plurality of magnetic nanoparticle rods having a length between 0.1 and 2 millimeters in response to the rotating magnetic field and the directed gradient; and
rotating the magnet at a second rotational frequency effective to move the magnetic nanoparticle rods along the vasculature in a walking end-over-end manner toward a thrombus in response to the rotating magnetic field and the directed gradient,
wherein the walking end-over-end manner of each of the rotating magnetic nanoparticle rods generates a circulating fluid motion within fluid proximal to the thrombus, thereby enhancing diffusion of a therapeutic agent to the thrombus and facilitating exposure of the therapeutic agent to the thrombus in response to the rotating magnetic field and the directed gradient.

18. The method of claim 17, further comprising causing the magnetic nanoparticle rods to travel through the vasculature by repeatedly:
a) walking end over end along the vasculature away from the magnetic field in response to the rotation of the magnetic nanoparticle rods and the directed magnetic gradient; and
b) flowing back through fluid in the vasculature towards the magnetic field in response to the rotation of the magnetic nanoparticle rods and the directed magnetic gradient.

19. The method of claim 17, wherein the first rotational frequency and the second rotational frequency are each between 1 Hz and 30 Hz, and wherein the first rotational frequency and the second rotational frequency are different.

20. The method of claim 17, wherein the first rotational frequency and the second rotational frequency are each between 1 Hz and 30 Hz, and wherein the first rotational frequency and the second rotational frequency are the same.

21. The method of claim 17, wherein the magnetic nanoparticles combine to form magnetic nanoparticle rods having a length between one and two millimeters when exposed to a rotating magnetic field having a magnitude of between 0.01 Tesla and 0.1 Tesla that is rotating at a rotational frequency between 3 and 10 Hz and to a magnetic gradient strength of between 0.01 Tesla/meter and 5 Tesla/meter.

* * * * *

UNITED STATES PATENT AND TRADEMARK OFFICE
CERTIFICATE OF CORRECTION

| | | |
|---|---|---|
| PATENT NO. | : 8,313,422 B2 | Page 1 of 1 |
| APPLICATION NO. | : 13/471908 | |
| DATED | : November 20, 2012 | |
| INVENTOR(S) | : Creighton, IV et al. | |

It is certified that error appears in the above-identified patent and that said Letters Patent is hereby corrected as shown below:

On the title page in Item (56), Under Other Publications, Change "Hypthesis," to --Hypothesis,--.

On page 2 in the second column at line 39, Change "Creighton, Iv et al." to --Creighton, IV et al.--.

In column 1 at line 8, Change "hag" to --having--.

In column 31 at line 49, Change "translate" to --translate)--.

In column 53 at line 3, Change "µl)" to --pl)--.

In column 53 at line 4, Change "µl)" to --pl)--.

In column 54 at line 39, Change "ml/min)" to --ml/min).--.

In column 54 at line 51, Change "min" to --min.--.

Signed and Sealed this
Fifteenth Day of January, 2013

David J. Kappos
*Director of the United States Patent and Trademark Office*